United States Patent
Rottlander et al.

(10) Patent No.: US 12,258,305 B2
(45) Date of Patent: *Mar. 25, 2025

(54) ALCOHOL DERIVATIVES AS KV7 POTASSIUM CHANNEL OPENERS

(71) Applicant: H. Lundbeck A/S, Valby (DK)

(72) Inventors: Mario Rottlander, Greve (DK); Anette Graven Sams, Vaerlose (DK); Xiaofang Wang, Shanghai (CN); Debasis Das, Shanghai (CN); Jian Hong, Shanghai (CN); Shu Hui Chen, Calabasas, CA (US)

(73) Assignee: H. Lundbeck A/S, Valby (DK)

( * ) Notice: Subject to any disclaimer, the term of this patent is extended or adjusted under 35 U.S.C. 154(b) by 0 days.

This patent is subject to a terminal disclaimer.

(21) Appl. No.: 17/869,116

(22) Filed: Jul. 20, 2022

(65) Prior Publication Data

US 2022/0380300 A1    Dec. 1, 2022

Related U.S. Application Data

(60) Continuation of application No. 16/781,106, filed on Feb. 4, 2020, now Pat. No. 11,434,199, which is a division of application No. 15/899,843, filed on Feb. 20, 2018, now Pat. No. 10,590,067.

(51) Int. Cl.
| | |
|---|---|
| *A61P 25/08* | (2006.01) |
| *A61P 25/04* | (2006.01) |
| *A61P 25/06* | (2006.01) |
| *A61P 25/18* | (2006.01) |
| *A61P 25/22* | (2006.01) |
| *A61P 25/24* | (2006.01) |
| *A61P 25/28* | (2006.01) |
| *C07C 235/06* | (2006.01) |
| *C07C 235/08* | (2006.01) |
| *C07C 235/26* | (2006.01) |

(52) U.S. Cl.
CPC .......... *C07C 235/06* (2013.01); *A61P 25/04* (2018.01); *A61P 25/06* (2018.01); *A61P 25/08* (2018.01); *A61P 25/18* (2018.01); *A61P 25/22* (2018.01); *A61P 25/24* (2018.01); *A61P 25/28* (2018.01); *C07C 235/08* (2013.01); *C07C 235/26* (2013.01); *C07B 2200/07* (2013.01); *C07C 2601/02* (2017.05); *C07C 2601/04* (2017.05)

(58) Field of Classification Search
CPC .......... A61P 25/04; A61P 25/06; A61P 25/08; A61P 25/18; A61P 25/22; A61P 25/24; A61P 25/28; C07C 235/06; C07C 235/08; C07C 235/26; C07C 2601/02; C07C 2601/04

See application file for complete search history.

(56) References Cited

U.S. PATENT DOCUMENTS

| | | | |
|---|---|---|---|
| 10,590,067 B2 | 3/2020 | Rottlander et al. | |
| 11,434,199 B2* | 9/2022 | Rottlander | C07C 235/08 |
| 11,548,849 B2* | 1/2023 | Rottlander | C07C 235/08 |
| 2016/0075663 A1 | 3/2016 | Resnick et al. | |
| 2019/0256456 A1 | 8/2019 | Rottlander et al. | |
| 2020/0172474 A1 | 6/2020 | Rottlander et al. | |
| 2021/0032196 A1 | 2/2021 | Rottlander et al. | |
| 2022/0280455 A1 | 9/2022 | Sams et al. | |

FOREIGN PATENT DOCUMENTS

| | | |
|---|---|---|
| CN | 105663136 A | 6/2016 |
| JP | 2017-95366 A | 6/2017 |
| TW | 200920350 A | 5/2009 |
| WO | WO 01/092526 A1 | 12/2001 |
| WO | WO 01/096540 A2 | 12/2001 |
| WO | WO 2006/033844 A2 | 3/2006 |
| WO | WO 2007/090409 A1 | 8/2007 |
| WO | WO 2007/104717 A1 | 9/2007 |
| WO | WO 2009/015667 A1 | 2/2009 |
| WO | WO 2010/060955 A1 | 6/2010 |
| WO | WO 2014/145852 A2 | 9/2014 |
| WO | WO 2019/161877 A1 | 8/2019 |

OTHER PUBLICATIONS

Humphries(J.BiomolecularScreening(2015)vol. 20(9)1055-1073).*
Wulff et al.(NatureReviews Drug Discovery8,982-1001(2009)).*
NIH Autism 2021.*
Gati et al.(J.Toxicol.2012;2012:756358).*
Cheung et al. Discovery of a Series of 2-phenyl-N-(2-(pyrrolidin-1-yl)phenyl)acetamides as Novel Molecular Switches that Modulate Modes of Kv7.2 (KCNQ2) Channel Pharmacology: Identification of (S)-2-phenyl-N-(2-(pyrrolidin-1-yl)phenyl)butanamide J Med Chem, Aug. 9, 2012; 55(15): 6975-6979. doi: 10.1021/jm300700v.*
International Search Report and Written Opinion for Application No. PCT/EP2018/054057 mailed Sep. 12, 2018.
International Preliminary Report on Patentability for Application No. PCT/EP2018/054057 mailed Sep. 3, 2020.
International Search Report and Written Opinion for International Application No. PCT/EP2020/071520 dated Sep. 14, 2020.

(Continued)

*Primary Examiner* — Valerie Rodriguez-Garcia
(74) *Attorney, Agent, or Firm* — Wolf, Greenfield & Sacks, P.C.

(57) ABSTRACT

The present invention provides novel compounds which activate the Kv7 potassium channels. Separate aspects of the invention are directed to pharmaceutical compositions comprising said compounds and uses of the compounds to treat disorders responsive to the activation of Kv7 potassium channels.

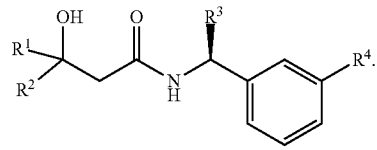

Formula I

20 Claims, No Drawings

(56) References Cited

OTHER PUBLICATIONS

International Search Report and Written Opinion for International Application No. PCT/EP2020/071514 mailed Oct. 12, 2020.
International Preliminary Report on Patentability for Application No. PCT/EP2020/071514, mailed Feb. 17, 2022.
International Preliminary Report on Patentability for Application No. PCT/EP2020/071520, mailed Feb. 17, 2022.
[No Author Listed] Medication treatment for autism. NICHD Eunice Kennedy Shriver National Institute of Child Health and Human Development. Apr. 19, 2021. http://www.nichd.nih.gov/health/topics/autism/conditioninfo/treatments/medication-treatment. Last accessed Sep. 2, 2021.
[No Author Listed] What causes autism? NICHD Eunice Kennedy Shriver National Institute of Child Health and Human Development. Jan. 31, 2017. http://www.nichd.nih.gov/health/topics/autism/conditioninfo/causes. Last accessed Sep. 2, 2021.
[No Author Listed], Chemical Catalog. Chemcats: Aurora Fine Chemicals. Butanamide, 3-hydroxy-3-methyl-N-(1(S)-1-(3-trifluoromethoxyphenyl] ethyl]. Apr. 2, 2018. Abstract. 1 page.
[No Author Listed], Chemical Catalog. Chemcats: Aurora Fine Chemicals. N-1-(3-difluoromethoxyphenyl) ethyl-1-cyclohexane acetamide. Feb. 13, 2017. Abstract. 1 page.
[No Author], CAS Registry File RN 2071998-86-0, STN Entry Date: Feb. 17, 2017.
Allen et al., Genetic potassium channel-associated epilepsies: Clinical review of the Kv family. Eur J Paediatr Neurol. Jan. 2020;24:105-116. Epub Dec. 14, 2019.
Bialer et al., Progress report on new antiepileptic drugs: a summary of the Sixth Eilat Conference (Eilat VI). Epilepsy Res. Sep. 2002;51(1-2):31-71.
Blom et al., From pan-reactive KV7 channel opener to subtype selective opener/inhibitor by addition of a methyl group. PLoS One. Jun. 23, 2014;9(6):e100209. doi: 10.1371/journal.pone.0100209.
CAS Registry File RN 2061854-53-1, STN Entry Date: Jan. 30, 2017.
CAS Registry File RN 2071323-29-8, STN Entry Date: Feb. 16, 2017.
Christie, Molecular and Functional Diversity of K+ Channels. Clin Exp Pharmacol Physiol. 1995; 22(12):944-951.
Cooper et al., Colocalization and coassembly of two human brain M-type potassium channel subunits that are mutated in epilepsy. Proc Natl Acad Sci U S A. Apr. 25, 2000;97(9):4914-9.
Dalby-Brown et al., Kv7 Channels: Function, Pharmacology and Channel Modulators. Curr Top Med Chem. 2006; 6:999-1023.
Delmas, Pathways Modulating Neural KCNQ/M (Kv7) Potassium Channels. Nat Rev Neurosci. Nov. 2005;6(11):850-62.
Dencker et al., Antimanic efficacy of retigabine in a proposed mouse model of bipolar disorder. Behav Brain Res. Feb. 11, 2010;207(1):78-83. doi: 10.1016/j.bbr.2009.09.040. Epub Oct. 6, 2009.
Durley et al., Chiral N,N-disubstituted trifluoro-3-amino-2-propanols are potent inhibitors of cholesteryl ester transfer protein. J Med Chem. 2002; 45(18):3891-3904.
Friedman et al., KCNQ channel openers reverse depressive symptoms via an active resilience mechanism. Nat Commun. May 24, 2016;7:11671.
Gati et al., Towards therapeutic applications of arthropod venom k(+)-channel blockers in CNS neurologic diseases involving memory acquisition and storage. J Toxicol. 2012;2012:756358. Epub Jun. 4, 2012.
Goldstein et al., Localization of KCNQ and KCNE channel subunits in the central and peripheral nervous system of the rat. Society for Neuroscience Abstracts 2003; Presentation No. 53.8.
Greene et al., Modulation of Kv7 channels and excitability in the brain. Cell Mol Life Sci. Feb. 2017;74(3):495-508.
Gunthorpe et al., The mechanism of action of retigabine (ezogabine), a first-in-class K+ channel opener for the treatment of epilepsy. Epilepsia. Mar. 2012;53(3):412-24. Epub Jan. 5, 2012.
Hansen et al., The KCNQ Channel Opener Retigabine Inhibits the Activity of Mesencephalic Dopaminergic Systems of the Rat. J Pharmacol Exp Ther. Sep. 2006;318(3):1006-19.
Humphries et al., Neuronal and cardiovascular potassium channels as therapeutic drug targets: promise and pitfalls. J Biomol Screen. Oct. 2015;20(9):1055-73. Epub Aug. 24, 2015.
Korsgaard et al., Anxiolytic Effects of Maxipost (BMS-204352) and Retigabine via Activation of Neuronal Kv7 Channels. J Pharmacol Exp Ther. Jul. 2005;314(1):282-92. Epub Apr. 6, 2005.
Koyama et al., Characterization of M-Current in Ventral Tegmental Area Dopamine Neurons. J Neurophysiol. Aug. 2006;96(2):535-43. Epub Jan. 4, 2006.
Li et al., Selective targeting of M-type potassium Kv7.4 channels demonstrates their role in the regulation of dopaminergic neuronal excitability and depression-like behaviour. Br J Pharmacol. Dec. 2017;174(23):4277-4294. Epub Oct. 19, 2017.
Marrion, Control of M-Current. Annual Review Physiology 1997; 59:483-504.
Meanwell N.A., Fluorine and fluorinated motifs in the design and application of bioisosteres for drug design. J Med Chem. Jul. 26, 2018;61(14):5822-5880. Epub Feb. 5, 2018.
Noda et al., KCN channels in glial cells. Society for Neuroscience Abstracts 2003; Presentation No. 53.9.
Rogawski, KCNQ2/KCNQ3 K+ channels and the molecular pathogenesis of epilepsy: implications for therapy. Trends Neurosci. Sep. 2000;23(9):393-8.
Rostock et al., D-23129: a new anticonvulsant with a broad spectrum activity in animal models of epileptic seizures. Epilepsy Res. Apr. 1996;23(3):211-23.
Saganich et al., Differential expression of genes encoding subthreshold-operating voltage-gated K+ channels in brain. J Neurosci. Jul. 1, 2001;21(13):4609-24.
Schroder et al., KCNQ4 channel activation by BMS-204352 and retigabine. Neuropharmacology. Jun. 2001;40(7):888-98.
Sotty et al., Antipsychotic-like effect of retigabine [N-(2-Amino-4-(fluorobenzylamino)-phenyl)carbamic acid ester], a KCNQ potassium channel opener, via modulation of mesolimbic dopaminergic neurotransmission. J Pharmacol Exp Ther. Mar. 2009;328(3):951-62. doi: 10.1124/jpet.108.146944. Epub Dec. 19, 2008.
Wang et al., KCNQ2 and KCNQ3 Potassium Channel Subunits: Molecular Correlates of the M-Channel. Science. Dec. 4, 1998;282(5395):1890-3.
Weaver et al., A thallium-sensitive, fluorescence-based assay for detecting and characterizing potassium channel modulators in mammalian cells. J Biomol Screen. Dec. 2004;9(8):671-7.
Wickenden et al., KCNQ channel expression in rat DRG following nerve ligation. Society for Neuroscience Abstracts 2002; Presentation No. 454.7.
Wickenden et al., Retigabine, A Novel Anti-Convulsant, Enhances Activation of KCNQ2/Q3 Potassium Channels. Molecular Pharmacology 2000; 58(3):591-600.
Wulff et al., Voltage-gated potassium channels as therapeutic targets. Nat Rev Drug Discov. Dec. 2009;8(12):982-1001.
Wuttke et al., The New Anticonvulsant Retigabine Favors Voltage-Dependent Opening of the Kv7.2 (KCNQ2) Channel by Binding to Its Activation Gate. Mol Pharmacol. Apr. 2005;67(4):1009-17.
U.S. Appl. No. 16/943,87, filed Jul. 30, 2020, Allowed, 2021-0032196.
U.S. Appl. No. 15/899,843, filed Feb. 20, 2018, Granted, U.S. Pat. No. 10,590,067.
U.S. Appl. No. 16/781,106, filed Feb. 4, 2020, Granted, U.S. Pat. No. 11,434,199.
U.S. Appl. No. 16/943,872, filed Jul. 30, 2020, Allowed, 2021-0032196.
U.S. Appl. No. 18/062,246, filed Dec. 6, 2022, Pending.
U.S. Appl. No. 17/631,762, filed Jan. 31, 2022, Published, 2022-0280455.
Barrese et al., KCNQ-Encoded Potassium Channels as Therapeutic Targets. Annu Rev Pharmacol Toxicol. Jan. 6, 2018;58:625-648. doi: 10.1146/annurev-pharmtox-010617-052912. Epub Oct. 6, 2017.
Borgini et al., Chemical modulation of Kv7 potassium channels. RSC Med Chem. Jan. 14, 2021;12(4):483-537. doi: 10.1039/d0md00328j.

(56) References Cited

OTHER PUBLICATIONS

Cao et al., Rescue of homeostatic regulation of striatal excitability and locomotor activity in a mouse model of Huntington's disease. Proc Natl Acad Sci U S A. Feb. 17, 2015;112(7):2239-44. doi: 10.1073/pnas.1405748112. Epub Feb. 2, 2015.

Cheung et al., Structures of human acetylcholinesterase in complex with pharmacologically important ligands. J Med Chem. Nov. 26, 2012;55(22):10282-6. doi: 10.1021/jm300871x. Epub Nov. 12, 2012.

Gilling et al., Dysfunction of the Heteromeric KV7.3/KV7.5 Potassium Channel is Associated with Autism Spectrum Disorders. Front Genet. Apr. 16, 2013;4:54. doi: 10.3389/fgene.2013.00054.

Roza et al., Retigabine, the specific KCNQ channel opener, blocks ectopic discharges in axotomized sensory fibres. Pain. Sep. 15, 2008;138(3):537-545. doi: 10.1016/j.pain.2008.01.031. Epub Mar. 10, 2008.

Wainger et al., Intrinsic membrane hyperexcitability of amyotrophic lateral sclerosis patient-derived motor neurons. Cell Rep. Apr. 10, 2014;7(1):1-11. doi: 10.1016/j.celrep.2014.03.019. Epub Apr. 3, 2014.

\* cited by examiner

ALCOHOL DERIVATIVES AS KV7 POTASSIUM CHANNEL OPENERS

CROSS REFERENCE TO RELATED APPLICATION(S)

This application is a Continuation application of U.S. application Ser. No. 16/781,106, filed Feb. 4, 2020, now U.S. Pat. No. 11,434,199, which is a Divisional application of U.S. application Ser. No. 15/899,843, filed Feb. 20, 2018, now U.S. Pat. No. 10,590,067, which applications are incorporated herein by reference.

FIELD OF THE INVENTION

The present invention relates to novel compounds which activate the Kv7 potassium channels. Separate aspects of the invention are directed to pharmaceutical compositions comprising said compounds and uses of the compounds to treat disorders responsive to the activation of Kv7 potassium channels

BACKGROUND OF THE INVENTION

Voltage-dependent potassium (Kv) channels conduct potassium ions (K+) across cell membranes in response to changes in the membrane potential and can thereby regulate cellular excitability by modulating (increasing or decreasing) the electrical activity of the cell. Functional Kv channels exist as multimeric structures formed by the association of four alpha and four beta subunits. The alpha subunits comprise six transmembrane domains, a pore-forming loop and a voltage-sensor and are arranged symmetrically around a central pore. The beta or auxiliary subunits interact with the alpha subunits and can modify the properties of the channel complex to include, but not be limited to, alterations in the channel's electrophysiological or biophysical properties, expression levels or expression patterns.

Nine Kv channel alpha subunit families have been identified and are termed Kv1-Kv9. As such, there is an enormous diversity in Kv channel function that arises as a consequence of the multiplicity of sub-families, the formation of both homomeric and heteromeric subunits within sub-families and the additional effects of association with beta subunits (Christie, 25 Clinical and Experimental Pharmacology and Physiology, 1995, 22, 944-951).

The Kv7 channel family consists of at least five members which include one or more of the following mammalian channels: Kv7.1, Kv7.2, Kv7.3, Kv7.4, Kv7.5 and any mammalian or non-mammalian equivalent or variant (including splice variants) thereof. Alternatively, the members of this family are termed by the gene name KCNQ1, KCNQ2, KCNQ3, KCNQ4 and KCNQ5 respectively (Dalby-Brown, et al., Current Topics in Medicinal Chemistry, 2006, 6, 9991023).

As mentioned above, the neuronal Kv7 potassium channels play roles in controlling neuronal excitation. Kv7 channels, in particular Kv7.2/Kv7.3 heterodimers, underlie the M-current (Wang et al Science. 1998 Dec. 4; 282(5395): 1890-3). The M-current has a characteristic time- and voltage-dependence that results in stabilisation of the membrane potential in response to multiple excitatory stimuli.

In this way, the M-current is involved in controlling neuronal excitability (Delmas & Brown, Nature, 2005, 6, 850-862). The M-current is a non-inactivating potassium current found in many neuronal cell types. In each cell type, it is dominant in controlling membrane excitability by being the only sustained current in the range of action potential initiation (Marrion, Annual Review Physiology 1997, 59, 483-504).

Retigabine (N-(2-amino-4-(4-fluorobenzylamino)-phenyl) carbamic acid ethyl ester) is a compound which binds to the Kv7 potassium channels (Wuttke, et al., Molecular Pharmacology, 2005, 67, 1009-1017). Retigabine activates $K^+$ current in neuronal cells and the pharmacology of this induced current displays concordance with the published pharmacology of the M-channel that has been correlated to the Kv7.2/3 $K^+$ channel heteromultimer which suggests that activation of Kv7.2/3 channels is responsible for at least some of the anticonvulsant activity of this agent (Wickenden, et al., Molecular Pharmacology 2000, 58, 591-600). Retigabine is effective in reducing the incidence of seizures in epileptic patients (Bialer, et al., Epilepsy Research 2002, 51, 31-71). Retigabine has a broad spectrum and potent anticonvulsant properties. It is active after oral and intraperitoneal administration in rats and mice in a range of anticonvulsant tests (Rostock, et al., Epilepsy Research 1996, 23, 211-223).

The five members of this family differ in their expression patterns. The expression of Kv7.1 is restricted to the heart, peripheral epithelial and smooth muscle, whereas the expression of Kv7.2, Kv7.3, Kv7.4 and Kv7.5 appear to be dominant in the nervous system which includes the hippocampus, cortex, ventral tegmental area, and dorsal root ganglion neurons (for a review see Greene & Hoshi, Cellular and Molecular Life Sciences, 2017, 74(3), 495-508).

The KCNQ2 and KCNQ3 genes appear to be mutated in an inherited form of epilepsy known as benign familial neonatal convulsions (Rogawski, Trends in Neurosciences 2000, 23, 393-398). The proteins encoded by the KCNQ2 and KCNQ3 genes are localised in the pyramidal neurons of the human cortex and hippocampus, regions of the brain associated with seizure generation and propagation (Cooper et al., Proceedings National Academy of Science USA 2000, 97, 4914-4919).

Furthermore, mRNA for Kv7.3 and 5, in addition to that for Kv7.2, are expressed in astrocytes and glial cells. Thus Kv7.2, Kv7.3 and Kv7.5 channels may help modulate synaptic activity in the CNS and contribute to the neuroprotective effects of KCNQ channel openers (Noda, et al., Society for Neuroscience Abstracts 2003, 53.9), which would be relevant for the treatment of neurodegenerative disorders such as but not limited to Alzheimer's disease, Parkinson's disease and Huntington's chorea.

mRNA for Kv7.2 and Kv7.3 subunits are found in brain regions associated with anxiety and emotional behaviours such as depression and bipolar disorder e.g. hippocampus, ventral tegmental area and amygdala (Saganich, et al. Journal of Neuroscience 2001, 21, 4609-4624; Friedman et al., Nat Commun. 2016; 7: 11671.), and retigabine is reportedly active in animal models of anxiety-like behaviour (Korsgaard et al J Pharmacol Exp Ther. 2005 July; 314(1): 282-92. Epub 2005 Apr. 6.). As such Kv7 channels are relevant for the treatment of emotional related disorders such as but not limited to bipolar depression, major depression, anxiety, suicide, panic attacks, social phobia.

Kv7.2/3 channels have also been reported to be upregulated in models of neuropathic pain (Wickenden, et al., Society for Neuroscience Abstracts 2002, 454.7), and potassium channel modulators have been hypothesised to be active in both neuropathic pain and epilepsy (Schroder, et al., Neuropharmacology 2001, 40, 888-898). In addition to a role in neuropathic pain, the expression of mRNA for Kv7.2-5 in the trigeminal and dorsal root ganglia and in the trigeminal nucleus caudalis implies that openers of these channels may also affect the sensory processing of migraine pain (Goldstein, et al. Society for Neuroscience Abstracts 2003, 53.8). Taken together, this evidence points to the relevance of KCNQ channel openers for the treatment of chronic pain and neuropathy related disorders.

WO 07/90409 relates to the use of Kv7 channel openers for the treatment of schizophrenia. Kv7 channel openers modulate the function of the dopaminergic system (Friedman et al., Nat Commun. 2016; Scotty et al J Pharmacol Exp Ther. 2009 March; 328(3):951-62. doi: 10.1124/jpet.108.146944. Epub 2008 Dec. 19; Koyama et al., J Neurophysiol. 2006 August; 96 (2):535-43. Epub 2006 Jan. 4; Li et al Br J Pharmacol. 2017 December; 174(23):4277-4294. doi: 10.1111/bph.14026. Epub 2017 Oct. 19; Hansen et al J Pharmacol Exp Ther. 2006 September; 318(3):1006-19. Epub 2006 Jun. 14) which would be relevant for the treatment of psychiatric disorders such as but not limited to psychosis, mania, stress-related disorders, acute stress reactions, attention deficit/hyperactivity disorder, posttraumatic stress disorder, obsessive compulsive disorder, impulsivity disorders, personality disorders, schizotypical disorder, aggression, autism spectrum disorders. WO 01/96540 discloses the use of modulators of the M-current formed by expression of KCNQ2 and KCNQ3 genes for insomnia, while WO 01/092526 discloses that modulators of Kv7.5 can be utilized for the treatment of sleep disorders. WO 09/015667 discloses the use of Kv7 openers in the treatment of sexual dysfunction.

Although patients suffering from the above mentioned disorders may have available treatment options, many of these options lack the desired efficacy and are accompanied by undesired side effects. Therefore, an unmet need exists for novel therapies for the treatment of said disorders.

In an attempt to identify new therapies, the inventors have identified a series of novel compounds as represented by Formula I which act as Kv7.2, Kv7.3, Kv7.4 and Kv7.5 channel openers. Accordingly, the present invention provides novel compounds as medicaments for the treatment of disorders which are modulated by the KCNQ potassium channels.

SUMMARY OF THE INVENTION

The present invention relates to a compound of Formula I

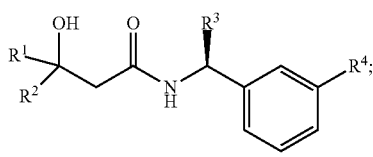

Formula I wherein
R1 is selected from the group consisting of $C_1$-$C_6$ alkyl, $CF_3$, $CH_2CF_3$, $CF_2CHF_2$, $C_3$-$C_8$ cycloalkyl, wherein said $C_3$-$C_8$ cycloalkyl may be substituted with 1 or 2 F, $CHF_2$ or $CF_3$, and R2 is H, $C_1$-$C_6$ alkyl or $CF_3$;
or
R1 and R2 combine to form $C_3$-$C_5$ cycloalkyl optionally substituted with F, $CHF_2$ or $CF_3$;
R3 is $C_1$-$C_3$ alkyl or $CH_2O$—$C_{1-3}$ alkyl, optionally substituted with F;

R4 is selected from the group consisting of $OCF_3$, $OCH_2CF_3$ or $OCHF_2$;

The invention also concerns a pharmaceutical composition comprising a compound according to the invention and a pharmaceutically acceptable carrier or excipient.

Furthermore, the invention concerns a method of treating a patient as described in the claims and embodiments and includes treatments of patients suffering from epilepsy, a bipolar disorder, migraine and schizophrenia comprising administering to the subject a therapeutically effective amount of the compound according to the invention.

DETAILED DESCRIPTION OF THE INVENTION

R4 is according to an embodiment of the invention $OCF_3$ or $OCHF_2$ and
R2 is according to another embodiment H or $CH_3$.
In one embodiment R1 is $C_3$-$C_4$ cycloalkyl optionally substituted with 1 or 2 F, $CHF_2$ or $CF_3$.
According to a specific embodiment R1 is t-butyl and R2 is H and R4 is one of $OCF_3$, $OCH_2CF_3$ or $OCHF_2$.
According to another specific embodiment R1 and R2 combine to form cyclobutyl optionally substituted with 1 or 2 F and R4 is one of $OCF_3$, $OCH_2CF_3$ or $OCHF_2$.
According to a specific embodiment of the invention the compound according to the invention is selected from the group consisting of:
(S)-3-hydroxy-4,4-dimethyl-N-[(1S)-1-[3-(trifluoromethoxy)phenyl]ethyl]pentanamide,
(R)-3-hydroxy-4,4-dimethyl-N-[(1S)-1-[3-(trifluoromethoxy)phenyl]ethyl]pentanamide,
(S)-3-hydroxy-4,4-dimethyl-N—((S)-1-(3-(2,2,2-trifluoroethoxy)phenyl)ethyl)pentanamide,
(R)-3-hydroxy-4,4-dimethyl-N—((S)-1-(3-(2,2,2-trifluoroethoxy)phenyl)ethyl)pentanamide,
(S)—N—((S)-1-(3-(difluoromethoxy)phenyl)ethyl)-3-hydroxy-4,4-dimethylpentanamide,
(R)—N—((S)-1-(3-(difluoromethoxy)phenyl)ethyl)-3-hydroxy-4,4-dimethylpentanamide,
(S)-3-hydroxy-4,4-dimethyl-N—((S)-1-(3-(trifluoromethyl)phenyl)ethyl)pentanamide,
(R)-3-hydroxy-4,4-dimethyl-N—((S)-1-(3-(trifluoromethyl)phenyl)ethyl)pentanamide,
(S)-3-hydroxy-4,4-dimethyl-N—((S)-1-(3-(trifluoromethoxy)phenyl)propyl)pentanamide,
(R)-3-hydroxy-4,4-dimethyl-N—((S)-1-(3-(trifluoromethoxy)phenyl)propyl)pentanamide,
(S)-3-(3,3-difluorocyclobutyl)-3-hydroxy-N—((S)-1-(3-(trifluoromethoxy)phenyl)ethyl)propanamide,
(R)-3-(3,3-difluorocyclobutyl)-3-hydroxy-N—((S)-1-(3-(trifluoro methoxy)phenyl)ethyl)propanamide,
(S)-3-hydroxy-4-methyl-N—((S)-1-(3-(2,2,2-trifluoroethoxy)phenyl)ethyl)pentanamide,
(R)-3-hydroxy-4-methyl-N—((S)-1-(3-(2,2,2-trifluoroethoxy)phenyl)ethyl)pentanamide,
(S)-3-(1-(difluoromethyl)cyclopropyl)-3-hydroxy-N—((S)-1-(3-(trifluoro-methoxy)phenyl)ethyl)propanamide,
(R)-3-(1-(difluoromethyl)cyclopropyl)-3-hydroxy-N—((S)-1-(3-(trifluoromethoxy)phenyl)ethyl)propanamide,
(R)-3-hydroxy-N—((S)-1-(3-(trifluoromethoxy)phenyl)ethyl)-3-(1-(trifluoromethyl)cyclopropyl)propanamide,
(S)-3-hydroxy-N—((S)-1-(3-(trifluoromethoxy)phenyl)ethyl)-3-(1-(trifluoromethyl)cyclopropyl)propanamide,
(S)-3-hydroxy-4-methyl-N—((S)-1-(3-(trifluoromethoxy)phenyl)ethyl)pentanamide, (R)-3-hydroxy-4-methyl-N—((S)-1-(3-(trifluoromethoxy) phenyl)ethyl)pentan amide,
N—((R)-2-(difluoromethoxy)-1-(3-(trifluoromethoxy)phenyl)ethyl)-3-(R)-hydroxy-4,4-dimethylpentanamide,
N—((R)-2-(difluoromethoxy)-1-(3-(trifluoromethoxy)phenyl)ethyl)-3-(S)-hydroxy-4,4-dimethylpentanamide,
(S)-3-hydroxy-N—((R)-2-methoxy-1-(3-(trifluoromethoxy)phenyl)ethyl)-4,4-dimethylpentanamide,
(R)-3-hydroxy-N—((R)-2-methoxy-1-(3-(trifluoromethoxy)phenyl)ethyl)-4,4-dimethylpentanamide,
(S)-2-(3,3-difluoro-1-hydroxycyclobutyl)-N-(1-(3-(trifluoromethoxy)phenyl)ethyl)acetamide,
(S)-2-(1-hydroxycyclobutyl)-N-(1-(3-(2,2,2-trifluoroethoxy)phenyl)ethyl)acetamide,
(3R)-3-hydroxy-4-methyl-N-[(1S)-1-[3-(2,2,2-trifluoroethoxy)phenyl]ethyl]-3-(trifluoromethyl)pentanamide,
(3S)-3-hydroxy-4-methyl-N-[(1S)-1-[3-(2,2,2-trifluoroethoxy)phenyl]ethyl]-3-(trifluoromethyl)pentanamide,
4,4,4-Trifluoro-3-hydroxy-N-[(1S)-1-[3-(trifluoromethoxy)phenyl]ethyl]-3-(trifluoromethyl)butanamide,
(R)-4,4,5,5-tetrafluoro-3-hydroxy-3-methyl-N—((S)-1-(3-(trifluoromethoxy)phenyl)ethyl)pentanamide,
(S)-4,4,5,5-tetrafluoro-3-hydroxy-3-methyl-N—((S)-1-(3-(trifluoromethoxy)phenyl)ethyl)pentanamide,
(R)-5,5,5-trifluoro-3-hydroxy-3-methyl-N—((S)-1-(3-(trifluoromethoxy)phenyl)ethyl)pentanamide,
(S)-5,5,5-trifluoro-3-hydroxy-3-methyl-N—((S)-1-(3-(trifluoro methoxy)phenyl)ethyl)pentanamide,
(R)-3-(1-fluorocyclopropyl)-3-hydroxy-N—((S)-1-(3-(trifluoromethoxy)phenyl)ethyl)butanamide,
(S)-3-(1-fluorocyclopropyl)-3-hydroxy-N—((S)-1-(3-(trifluoro-methoxy)phenyl)ethyl)butanamide,
(R)-2-(1-hydroxycyclopentyl)-N-(2-methoxy-1-(3-(trifluoromethoxy)phenyl)ethyl)acetamide,
(R)-3-cyclopropyl-3-hydroxy-N—((S)-1-(3-(2,2,2-trifluoroethoxy)phenyl)ethyl)butanamide,
(S)-3-cyclopropyl-3-hydroxy-N—((S)-1-(3-(2,2,2-trifluoroethoxy)phenyl)ethyl)butanamide,
(S)-4,4,4-trifluoro-3-hydroxy-3-methyl-N—((S)-1-(3-(2,2,2-trifluoroethoxyphenyl)ethyl)butanamide, AND
(R)-4,4,4-trifluoro-3-hydroxy-3-methyl-N—((S)-1-(3-(2,2,2-trifluoroethoxy)phenyl)ethyl)butanamide Reference to compounds encompassed by the present invention includes racemic mixtures of the compounds, optical isomer of the compounds for which this is relevant, and polymorphic and amorphic forms of compounds of the present invention, as well as tautomeric forms the compounds for which this is relevant. Furthermore, the compounds of the present invention may potentially exist in unsolvated as well as in solvated forms with pharmaceutically acceptable solvents such as water, ethanol and the like. Both solvated and unsolvated forms of the compounds are encompassed by the present invention.

The compound according to the invention may be in a pharmaceutical composition comprising the compound and a pharmaceutically acceptable excipient or carrier.

In one embodiment, the invention relates to a compound according to the invention for use in therapy.

In another embodiment the invention relates to a method of treating a patient in the need thereof suffering from epilepsy, bipolar disorder, migraine or schizophrenia comprising administering to the subject a therapeutically effective amount of a compound according to the invention In yet another embodiment the invention relates to a method of treating a patient in the need thereof suffering from psychosis, mania, stress-related disorders, acute stress reactions, bipolar depression, major depression, anxiety, panic attacks, social phobia, sleep disturbances, ADHD, PTSD, OCD, impulsivity disorders, personality disorders, schizotypical disorder, aggression, chronic pain, neuropathy, autism spectrum disorders, Huntingtons chorea, sclerosis, multiple sclerosis, alzhiemers disease comprising administering to the subject a therapeutically effective amount of a compound according to the invention According to an embodiment the compounds of the invention is used in therapy.

The use of a compound according to the invention is for the treatment of epilepsy, bipolar disorder, migraine or schizophrenia or in another embodiment for the treatment of psychosis, mania, stress-related disorders, acute stress reactions, bipolar depression, major depression, anxiety, panic attacks, social phobia, sleep disturbances, ADHD, PTSD, OCD, impulsivity disorders, personality disorders, schizotypical disorder, aggression, chronic pain, neuropathy, autism spectrum disorders, Huntingtons chorea, sclerosis, multiple sclerosis, alzhiemers disease.

In another embodiment, the compound of the invention is for the manufacture of a medicament for treating epilepsy, bipolar disorder, migraine or schizophrenia or in another embodiment for the manufacture of a medicament for treating psychosis, mania, stress-related disorders, acute stress reactions, bipolar depression, major depression, anxiety, panic attacks, social phobia, sleep disturbances, ADHD, PTSD, OCD, impulsivity disorders, personality disorders, schizotypical disorder, aggression, chronic pain, neuropathy, autism spectrum disorders, Huntingtons chorea, sclerosis, multiple sclerosis, alzhiemers disease.

In the present context, "optionally substituted" means that the indicated moiety may or may not be substituted, and when substituted is mono- or di-substituted. It is understood that where no substituents are indicated for an "optionally substituted" moiety, then the position is held by a hydrogen atom.

A given range may interchangeably be indicated with "-" (dash) or "to", e.g. the term "$C_{1-3}$ alkyl" is equivalent to "$C_1$ to $C_3$ alkyl".

The terms "$C_1$-$C_3$ alkyl" and "$C_1$-$C_6$ alkyl" refer to an unbranched or branched saturated hydrocarbon having from one up to six carbon atoms, inclusive. Examples of such groups include, but are not limited to, methyl, ethyl, 1-propyl, 2-propyl, 1-butyl, 2-butyl and t-butyl.

The term "$C_1$-$C_3$ alkoxy" refers to a moiety of the formula —OR, wherein R indicates $C_1$-$C_3$ alkyl as defined above.

The terms "$C_3$-$C_6$ cycloalkyl", "$C_3$-$C_5$ cycloalkyl" or "$C_3$-$C_8$ cycloalkyl" refers to a saturated monocylic ring. Examples of such groups includes cyclopropyl, cyclobutyl, cyclopentyl, cyclohexyl, cycloheptyl and cyclooctyl.

Administration Routes:

Pharmaceutical compositions comprising a compound of the present invention defined above, may be specifically formulated for administration by any suitable route such as the oral, rectal, nasal, buccal, sublingual, transdermal and parenteral (e.g. subcutaneous, intramuscular, and intravenous) route; the oral route being preferred.

It will be appreciated that the route will depend on the general condition and age of the subject to be treated, the nature of the condition to be treated and the active ingredient.

Pharmaceutical Formulations and Excipients:

In the following, the term, "excipient" or "pharmaceutically acceptable excipient" refers to pharmaceutical excipients including, but not limited to, fillers, antiadherents, binders, coatings, colours, disintegrants, flavours, glidants, lubricants, preservatives, sorbents, sweeteners, solvents, vehicles and adjuvants.

The present invention also provides a pharmaceutical composition comprising a compound according to the invention, such as one of the compounds disclosed in the Experimental Section herein. The present invention also provides a process for making a pharmaceutical composition comprising a compound according to the invention. The pharmaceutical compositions according to the invention may be formulated with pharmaceutically acceptable excipients in accordance with conventional techniques such as those disclosed in Remington, "The Science and Practice of Pharmacy", 22$^{th}$ edition (2012), Edited by Allen, Loyd V., Jr.

Pharmaceutical compositions for oral administration include solid oral dosage forms such as tablets, capsules, powders and granules; and liquid oral dosage forms such as solutions, emulsions, suspensions and syrups as well as powders and granules to be dissolved or suspended in an appropriate liquid.

Solid oral dosage forms may be presented as discrete units (e.g. tablets or hard or soft capsules), each containing a predetermined amount of the active ingredient, and preferably one or more suitable excipients. Where appropriate, the solid dosage forms may be prepared with coatings such as enteric coatings or they may be formulated so as to provide modified release of the active ingredient such as delayed or extended release according to methods well known in the art. Where appropriate, the solid dosage form may be a dosage form disintegrating in the saliva, such as for example an orodispersible tablet.

Examples of excipients suitable for solid oral formulation include, but are not limited to, microcrystalline cellulose, corn starch, lactose, mannitol, povidone, croscarmellose sodium, sucrose, cyclodextrin, talcum, gelatin, pectin, magnesium stearate, stearic acid and lower alkyl ethers of cellulose. Similarly, the solid formulation may include excipients for delayed or extended release formulations known in the art, such as glyceryl monostearate or hypromellose. If solid material is used for oral administration, the formulation may for example be prepared by mixing the active ingredient with solid excipients and subsequently compressing the mixture in a conventional tabletting machine; or the formulation may for example be placed in a hard capsule e.g. in powder, pellet or mini tablet form. The amount of solid excipient will vary widely but will typically range from about 25 mg to about 1 g per dosage unit.

Liquid oral dosage forms may be presented as for example elixirs, syrups, oral drops or a liquid filled capsule. Liquid oral dosage forms may also be presented as powders for a solution or suspension in an aqueous or non-aqueous liquid. Examples of excipients suitable for liquid oral formulation include, but are not limited to, ethanol, propylene glycol, glycerol, polyethylenglycols, poloxamers, sorbitol, poly-sorbate, mono and di-glycerides, cyclodextrins, coconut oil, palm oil, and water. Liquid oral dosage forms may for example be prepared by dissolving or suspending the active ingredient in an aqueous or non-aqueous liquid, or by incorporating the active ingredient into an oil-in-water or water-in-oil liquid emulsion.

Further excipients may be used in solid and liquid oral formulations, such as colourings, flavourings and preservatives etc.

Pharmaceutical compositions for parenteral administration include sterile aqueous and nonaqueous solutions, dispersions, suspensions or emulsions for injection or infusion, concentrates for injection or infusion as well as sterile powders to be reconstituted in sterile solutions or dispersions for injection or infusion prior to use. Examples of excipients suitable for parenteral formulation include, but are not limited to water, coconut oil, palm oil and solutions of cyclodextrins. Aqueous formulations should be suitably buffered if necessary and rendered isotonic with sufficient saline or glucose.

Other types of pharmaceutical compositions include suppositories, inhalants, creams, gels, dermal patches, implants and formulations for buccal or sublingual administration.

It is requisite that the excipients used for any pharmaceutical formulation comply with the intended route of administration and are compatible with the active ingredients.

Doses:

In one embodiment, the compound of the present invention is administered in an amount from about 0.001 mg/kg body weight to about 100 mg/kg body weight per day. In particular, daily dosages may be in the range of 0.01 mg/kg body weight to about 50 mg/kg body weight per day. The exact dosages will depend upon the frequency and mode of administration, the gender, the age, the weight, and the general condition of the subject to be treated, the nature and the severity of the condition to be treated, any concomitant diseases to be treated, the desired effect of the treatment and other factors known to those skilled in the art.

A typical oral dosage for adults will be in the range of 0.1-1000 mg/day of a compound of the present invention, such as 1-500 mg/day, such as 1-100 mg/day or 1-50 mg/day. Conveniently, the compounds of the invention are administered in a unit dosage form containing said compounds in an amount of about 0.1 to 500 mg, such as 10 mg, 50 mg 100 mg, 150 mg, 200 mg or 250 mg of a compound of the present invention.

Isomeric and Tautomeric Forms:

When compounds of the present invention contain one or more chiral centers reference to any of the compounds will, unless otherwise specified, cover the enantiomerically or diastereomerically pure compound as well as mixtures of the enantiomers or diastereomers in any ratio.

MDL Enhanced Stereo representation is used to describe unknown stereochemistry of the compounds of the invention. Hence, the label "or1" on a chiral carbon atom is used to indicate that the absolute stereoconformation at this atom is not known; e.g. the stereoconformation at this carbon atom is either (S) or (R).

Furthermore, the chiral bond from a carbon atom labelled "or1", using upward wedge or downward wedge, are equal representations; e.g. the two drawings have the same meaning, the meaning being that the absolute stereoconformation at the "or1" labelled carbon atom is not known and can be (S) or (R).

Thus, the use of upward wedge bonds and downward wedge bonds from atoms labelled "or1", are merely intended to provide a visual cue that the drawings represent different stereoisomers, in which the conformation at the "or1" labelled carbon atom is not known.

Furthermore, some of the compounds of the present invention may exist in different tautomeric forms and it is intended that any tautomeric forms that the compounds are able to form are included within the scope of the present invention.

Therapeutically Effective Amount:

In the present context, the term "therapeutically effective amount" of a compound means an amount sufficient to alleviate, arrest, partly arrest, remove or delay the clinical manifestations of a given disease and its complications in a therapeutic intervention comprising the administration of said compound. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician.

Treatment and Treating:

In the present context, "treatment" or "treating" is intended to indicate the management and care of a patient for the purpose of alleviating, arresting, partly arresting, removing or delaying progress of the clinical manifestation of the disease. The patient to be treated is preferably a mammal, in particular a human being.

All references, including publications, patent applications and patents, cited herein are hereby incorporated by reference in their entirety and to the same extent as if each reference were individually and specifically indicated to be incorporated by reference and were set forth in its entirety (to the maximum extent permitted by law).

Headings and sub-headings are used herein for convenience only, and should not be construed as limiting the invention in any way.

The use of any and all examples, or exemplary language (including "for instance", "for example", "e.g.", and "as such") in the present specification is intended merely to better illuminate the invention, and does not pose a limitation on the scope of invention unless otherwise indicated.

The citation and incorporation of patent documents herein is done for convenience only, and does not reflect any view of the validity, patentability and/or enforceability of such patent documents.

The present invention includes all modifications and equivalents of the subject-matter recited in the claims appended hereto, as permitted by applicable law.

FURTHER EMBODIMENTS OF THE INVENTION

1. A compound of formula Formula I

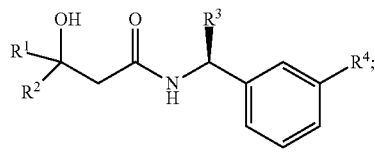

Formula I wherein
R1 is selected from the group consisting of $C_1$-$C_6$ alkyl, $CF_3$, $CH_2CF_3$, $CF_2CHF_2$, $C_3$-$C_8$ cycloalkyl, wherein said $C_3$-$C_8$ cycloalkyl may be substituted with 1 or 2 F, $CHF_2$ or $CF_3$, and R2 is H, $C_1$-$C_6$ alkyl or $CF_3$;
or
R1 and R2 combine to form $C_3$-$C_8$ cycloalkyl optionally substituted with 1 or 2 F, $CHF_2$ or $CF_3$;
R3 is $C_1$-$C_3$ alkyl or $CH_2O$—$C_{1-3}$ alkyl, said $C_1$-$C_3$ alkyl or $CH_2O$—$C_{1-3}$ alkyl may optionally be substituted with 1 or 2 F;
R4 is selected from the group consisting of $C_1$-$C_6$ alkoxy, $OCF_3$, $OCH_2CF_3$, $OCHF_2$, $CF_3$.

2. The compound according to embodiment 1, wherein R4 is $OCF_3$ or $OCHF_2$.
3. The compound according to any of the previous embodiments, wherein R2 is H or $CH_3$.
4. The compound according to any of the previous embodiments, wherein R3 is $CH_2O$—$C_{1-3}$ alkyl.
5. The compound according to any of the previous embodiments, wherein R1 is $C_3$-$C_4$ cycloalkyl optionally substituted with 1 or 2 F, $CHF_2$ or $CF_3$.
6. The compound according to any of the previous embodiments, wherein R1 is t-butyl and R2 is H and R4 is $OCF_3$, $OCH_2CF_3$, $OCHF_2$ or $CF_3$.
7. The compound according to any of the previous embodiments, wherein R1 and R2 combine to form a cyclobutyl optionally substituted with 1 or 2 F and R4 is $OCF_3$, $OCH_2CF_3$, $OCHF_2$ or $CF_3$.
8. The compound according to embodiment 1, wherein the compound is selected from the group consisting of:
(S)-3-hydroxy-4,4-dimethyl-N-[(1S)-1-[3-(trifluoromethoxy)phenyl]ethyl]pentanamide,
R)-3-hydroxy-4,4-dimethyl-N-[(1S)-1-[3-(trifluoromethoxy)phenyl]ethyl]pentanamide,
(S)-3-hydroxy-4,4-dimethyl-N—((S)-1-(3-(2,2,2-trifluoroethoxy)phenyl)ethyl)pentanamide,
(R)-3-hydroxy-4,4-dimethyl-N—((S)-1-(3-(2,2,2-trifluoroethoxy)phenyl)ethyl)pentanamide,
(S)—N—((S)-1-(3-(difluoromethoxy)phenyl)ethyl)-3-hydroxy-4,4-dimethylpentanamide,
(R)—N—((S)-1-(3-(difluoromethoxy)phenyl)ethyl)-3-hydroxy-4,4-dimethylpentanamide,
(S)-3-hydroxy-4,4-dimethyl-N—((S)-1-(3-(trifluoromethyl)phenyl)ethyl)pentanamide
(R)-3-hydroxy-4,4-dimethyl-N—((S)-1-(3-(trifluoromethyl)phenyl)ethyl)pentanamide,
(S)-3-hydroxy-4,4-dimethyl-N—((S)-1-(3-(trifluoromethoxy)phenyl)propyl)pentanamide,
(R)-3-hydroxy-4,4-dimethyl-N—((S)-1-(3-(trifluoromethoxy)phenyl)propyl)pentanamide,
(S)-3-(3,3-difluorocyclobutyl)-3-hydroxy-N—((S)-1-(3-(trifluoromethoxy)phenyl)ethyl)propanamide,
(R)-3-(3,3-difluorocyclobutyl)-3-hydroxy-N—((S)-1-(3-(trifluoromethoxy)phenyl)ethyl)propanamide,
(S)-3-hydroxy-4-methyl-N—((S)-1-(3-(2,2,2-trifluoroethoxy)phenyl)ethyl)pentanamide,
(R)-3-hydroxy-4-methyl-N—((S)-1-(3-(2,2,2-trifluoroethoxy)phenyl)ethyl)pentanamide,
(S)-3-(1-(difluoromethyl)cyclopropyl)-3-hydroxy-N—((S)-1-(3-(trifluoro-methoxy)phenyl)ethyl)propanamide,
(R)-3-(1-(difluoromethyl)cyclopropyl)-3-hydroxy-N—((S)-1-(3-(trifluoromethoxy)phenyl)ethyl)propanamide,
(R)-3-hydroxy-N—((S)-1-(3-(trifluoromethoxy)phenyl)ethyl)-3-(1-(trifluoromethyl)cyclopropyl)propanamide,
(S)-3-hydroxy-N—((S)-1-(3-(trifluoromethoxy)phenyl)ethyl)-3-(1-(trifluoromethyl)cyclopropyl)propanamide,
(S)-3-hydroxy-4-methyl-N—((S)-1-(3-(trifluoromethoxy)phenyl)ethyl)pentanamide,
(R)-3-hydroxy-4-methyl-N—((S)-1-(3-(trifluoromethoxy)phenyl)ethyl)pentanamide,
N—((R)-2-(difluoromethoxy)-1-(3-(trifluoromethoxy)phenyl)ethyl)-3-(R)-hydroxy-4,4-dimethylpentanamide,
N—((R)-2-(difluoromethoxy)-1-(3-(trifluoromethoxy)phenyl)ethyl)-3-(S)-hydroxy-4,4-dimethylpentanamide,
(S)-3-hydroxy-N—((R)-2-methoxy-1-(3-(trifluoromethoxy)phenyl)ethyl)-4,4-dimethylpentanamide,
(R)-3-hydroxy-N—((R)-2-methoxy-1-(3-(trifluoromethoxy)phenyl)ethyl)-4,4-dimethylpentanamide, (S)-2-(3,3-difluoro-1-hydroxycyclobutyl)-N-(1-(3-(trifluoromethoxy)phenyl)ethyl)acetamide,
(S)-2-(1-hydroxycyclobutyl)-N-(1-(3-(2,2,2-trifluoroethoxy)phenyl)ethyl)acetamide,
(3R)-3-hydroxy-4-methyl-N-[(1S)-1-[3-(2,2,2-trifluoroethoxy)phenyl]ethyl]-3-(trifluoromethyl)pentanamide,
(3S)-3-hydroxy-4-methyl-N-[(1S)-1-[3-(2,2,2-trifluoroethoxy)phenyl]ethyl]-3-(trifluoromethyl)pentanamide,
4,4,4-Trifluoro-3-hydroxy-N-[(1S)-1-[3-(trifluoromethoxy)phenyl]ethyl]-3-(trifluoromethyl)butanamide,
(R)-4,4,5,5-tetrafluoro-3-hydroxy-3-methyl-N—((S)-1-(3-(trifluoromethoxy)phenyl)ethyl)pentanamide,
(S)-4,4,5,5-tetrafluoro-3-hydroxy-3-methyl-N—((S)-1-(3-(trifluoromethoxy)phenyl)ethyl)pentanamide,
(R)-5,5,5-trifluoro-3-hydroxy-3-methyl-N—((S)-1-(3-(trifluoromethoxy)phenyl)ethyl)pentanamide,
(S)-5,5,5-trifluoro-3-hydroxy-3-methyl-N—((S)-1-(3-(trifluoro methoxy)phenyl)ethyl)pentanamide,
(R)-3-(1-fluorocyclopropyl)-3-hydroxy-N—((S)-1-(3-(trifluoromethoxy)phenyl)ethyl)butanamide,
(S)-3-(1-fluorocyclopropyl)-3-hydroxy-N—((S)-1-(3-(trifluoro-methoxy)phenyl)ethyl)butanamide,
(R)-2-(1-hydroxycyclopentyl)-N-(2-methoxy-1-(3-(trifluoromethoxy)phenyl)acetamide,
(R)-3-cyclopropyl-3-hydroxy-N—((S)-1-(3-(2,2,2-trifluoroethoxy)phenyl)ethyl)butanamide,
(S)-3-cyclopropyl-3-hydroxy-N—((S)-1-(3-(2,2,2-trifluoroethoxy)phenyl)ethyl)butanamide,
(R)-4,4,4-trifluoro-3-hydroxy-3-methyl-N—((S)-1-(3-(2,2,2-trifluoroethoxy)phenyl)ethyl)butanamide, AND
(R)-4,4,4-trifluoro-3-hydroxy-3-methyl-N—((S)-1-(3-(2,2,2-trifluoroethoxy)phenyl)ethyl)butanamide 9. A method of treating a subject suffering from a disease or disorder selected from the group consisting of epilepsy, a bipolar disorder, migraine and schizophrenia, psychosis, mania, stress-related disorders, acute stress reactions, bipolar depression, major depression, anxiety, panic attacks, social phobia, sleep disturbances, ADHD, PTSD, OCD, impulsivity disorders, personality disorders, schizotypical disorder, aggression, chronic pain, neuropathy, autism spectrum disorders, Huntingtons chorea, sclerosis, multiple sclerosis, Alzhiemers Disease comprising administering to the subject a therapeutically effective amount of the compound of embodiments 1-8

10. Use of a compound disclosed in embodiments 1 to 8 in therapy.

11. Use of a compound disclosed in embodiments 1 to 8 for the treatment of epilepsy, bipolar disorder, migraine or schizophrenia.

12. Use of a compound disclosed in embodiments 1 to 8 for the treatment of psychosis, mania, stress-related disorders, acute stress reactions, bipolar depression, major depression, anxiety, panic attacks, social phobia, sleep disturbances, ADHD, PTSD, OCD, impulsivity disorders, personality disorders, schizotypical disorder, aggression, chronic pain, neuropathy, autism spectrum disorders, Huntingtons chorea, sclerosis, multiple sclerosis, alzhiemers disease.

13. A compound disclosed in embodiments 1 to 8 for the manufacture of a medicament for treating epilepsy, bipolar disorder, migraine or schizophrenia.

14. A compound disclosed in embodiments 1 to 8 for the manufacture of a medicament for treating psychosis, mania, stress-related disorders, acute stress reactions, bipolar depression, major depression, anxiety, panic attacks, social phobia, sleep disturbances, ADHD, PTSD, OCD, impulsivity disorders, personality disorders, schizotypical disorder, aggression, chronic pain, neuropathy, autism spectrum disorders, Huntingtons chorea, sclerosis, multiple sclerosis, alzhiemers disease

EXPERIMENTAL SECTION

Biological Evaluation:
Cell Culture

A synthesized cDNA fragment encoding human Kv7.3 and human Kv7.2 separated by a P2A sequence was inserted into the pcDNA5/FRT/TO vector using the BamHI and XhoI restriction sites. The construct was then transfected into HEK Flp-In 293 cells using Lipofectamine2000. The transfected cells were grown for 48 hours in DMEM containing 10% (v/v) FBS and 1% PenStrep and subsequently maintained under selection in DMEM containing 10% (v/v) FBS, 1% PenStrep and 200 ug/mL Hygromycin B at 37° C. in a humidified atmosphere of 5% $CO_2$. The resultant stable hKv7.2/hKv7.3 cell line (HEK-hKv7.2/hKv7.3) was functionally tested with automated whole cell patch-clamp and displayed a typical Kv7-current which was sensitive to XE991 and potentiated by Retigabine.

Thallium Influx Assay

The thallium influx assay for potassium channel activation was performed analogously to a published procedure (C. D. Weaver, et al., J Biomol Screen 2004, 9, 671-677) using the FLIPR Potassium Assay kit (Molecular Devices). HEK-hKv7.2/hKv7.3 cells were plated onto 96-well, black-walled, clear-bottomed culture plates (Corning, Acton, MA, USA) at a density of 80,000 cells/well (100 μl/well) if the cells were assayed the following day, or 40,000 cells/well (100 μl/well) if the cells were assayed two days after seeding.

On the assay day, the medium was removed after which 50 μL/well of test compound diluted to 2× final concentration in HBSS containing 20 mM HEPES, and 50 uL/well of 2× dye load buffer were added. The cells were then incubated for 60 min at room temperature in the dark. Chloride-free stimulation buffer containing $Tl^+$ and $K^+$ at 5× final concentration (5× concentration: 5 mM in both cases) and test compound at 1× final concentration, were prepared during the incubation. The cells were then assayed in a FDSS7000EX Functional Drug Screening System (Hamamatsu). Following 60 sec of baseline fluorescence signal reading at 0.1 Hz, and 10 sec at 1 Hz, 25 uL/well of stimulation buffer were added and the fluorescence continuously measured for 50 sec at 1 Hz followed, by 4 min at 0.1 Hz. Compound effect was quantified using AUC as readout and normalized to a reference compound, which was included on each plate.

Compound Effects

In the assay described above, the compounds of the invention had the following biological activity:

| Example | $EC_{50}$, nM |
| --- | --- |
| 1a | 680 |
| 1b | 3300 |
| 2a | 460 |
| 2b | 1800 |
| 3a | 11000 |
| 3b | 1500 |
| 4a | 11000 |
| 4b | 1200 |
| 5 | 1800 |
| 6 | 3000 |
| 7a | 220 |

-continued

| Example | EC$_{50}$, nM |
|---|---|
| 7b | 1500 |
| 8a | 430 |
| 8b | 3000 |
| 9 | 560 |
| 10a | 650 |
| 10b | 1300 |
| 11a | 1500 |
| 11b | 4500 |
| 12a | 1600 |
| 12b | 5900 |
| 13a | 1900 |
| 13b | 2900 |
| 14a | 2000 |
| 14b | 6600 |
| 15a | 2100 |
| 15b | 11000 |
| 16a | 3000 |
| 16b | 10000 |
| 17 | 2500 |
| 18a | 1300 |
| 18b | 7100 |
| 19a | 1700 |
| 19b | 3400 |
| 20a | 3100 |
| 20b | 14000 |
| 21a | 3500 |
| 21b | 250 |

Synthesis of the Compounds of the Invention

General Methods:

$^1$H NMR spectra were recorded at 400.13 MHz on a Bruker Avance III 400 instrument or at 300.13 MHz on a Bruker Avance 300 instrument. Deuterated dimethyl sulfoxide or deuterated chloroform was used as solvent. Tetramethylsilane was used as internal reference standard. Chemical shift values are expressed in ppm-values relative to tetramethylsilane. The following abbreviations are used for multiplicity of NMR signals: s=singlet, d=doublet, t=triplet, q=quartet, qui=quintet, h=heptet, dd=double doublet, ddd=double double doublet, dt=double triplet, dq=double quartet, tt=triplet of triplets, m=multiplet and brs=broad singlet.

Chromatographic systems and methods to evaluate chemical purity (LCMS methods) and chiral purity (SFC and HPLC methods) are described below.

LCMS Method 1: Apparatus: Agilent 1200 LCMS System with ELS Detector.

| Column | Waters Xbridge-C18, 50 × 2 mm, 5 μm |
|---|---|
| Flow rate | 0.8 mL/min |
| Run time | 4.5 min. |
| Wavelength | 254 nm |
| Column temp | 50° C. |
| Ion source | ESI |
| Solvent A | Water + 0.04% TEA |
| Solvent B | MeCN + 0.02% TEA |

| Gradient | Time (min) | A % | B % |
|---|---|---|---|
| | 0 | 99 | 1 |
| | 3.4 | 0 | 100 |
| | 4 | 99 | 1 |
| | 4.5 | 99 | 1 |

LCMS Method 2: Apparatus: Agilent 1200 LCMS System with ELS Detector

| Column | Phenomenex Luna-C18, 50 × 2 mm, 5 μm |
|---|---|
| Flow rate | 0.8 mL/min |
| Run time | 4.5 min. |
| Wavelength | 254 nm |
| Column temp | 50° C. |
| Ion source | ESI |
| Solvent A | Water + 0.1% TEA |
| Solvent B | MeCN + 0.05% TEA |

| Gradient | Time (min) | A % | B % |
|---|---|---|---|
| | 0 | 99 | 1 |
| | 3.4 | 0 | 100 |
| | 4 | 99 | 1 |
| | 4.5 | 99 | 1 |

LCMS Method 3: Apparatus Agilent 1200 LCMS System with ELS Detector

| Column | Waters XBridge ShieldRP18, 50 × 2.1 mm, 5 μm |
|---|---|
| Flow rate | 0.8 mL/min |
| Run time | 4.5 min. |
| Wavelength | 254 nm |
| Column temp | 40° C. |
| Ion source | ESI |
| Solvent A | Water + 0.05% NH$_3$·H$_2$O |
| Solvent B | MeCN |

| Gradient | Time (min) | A % | B % |
|---|---|---|---|
| | 0 | 95 | 5 |
| | 3.4 | 0 | 100 |
| | 4 | 0 | 100 |
| | 4.5 | 95 | 5 |

LCMS Method 4 Apparatus Agilent 1200 LCMS System with ELS Detector

| Column | Phenomenex Luna-C18, 50 × 2 mm, 5 μm |
|---|---|
| Flow rate | 0.8 mL/min |
| Run time | 4.5 min. |
| Wavelength | 254 nm |
| Column temp | 50° C. |
| Ion source | ESI |
| Solvent A | Water + 0.1% TEA |
| Solvent B | MeCN + 0.05% TEA |

| Gradient | Time | A % | B % |
|---|---|---|---|
| | 0 | 90 | 10 |
| | 3.4 | 0 | 100 |
| | 4 | 0 | 100 |
| | 4.01 | 90 | 10 |
| | 4.5 | 90 | 10 |

LCMS Method 5: Apparatus Agilent 1200 LCMS System with ELS Detector

| Column | Waters Xbridge-C18, 50 × 2 mm, 5 μm |
|---|---|
| Flow rate | 0.8 mL/min |
| Run time | 4.5 min. |
| Wavelength | 254 nm |
| Column temp | 50° C. |
| Ion source | ESI |

| Solvent A | Water + 0.04% TEA | | |
|---|---|---|---|
| Solvent B | MeCN + 0.02% TEA | | |
| Gradient | Time | A % | B % |
| | 0 | 90 | 10 |
| | 3.4 | 0 | 100 |
| | 4 | 0 | 100 |
| | 4.01 | 90 | 10 |
| | 4.5 | 90 | 10 |

LCMS Method 6: Apparatus Agilent 1200 LCMS System with ELS Detector

| Column | Waters XBridge ShieldRP18, 2.1*50 mm, 5 μm | | |
|---|---|---|---|
| Flow rate | 0.8 mL/min | | |
| Run time | 4.5 min. | | |
| Wavelength | 254 nm | | |
| Column temp | 40° C. | | |
| Ion source | ESI | | |
| Solvent A | Water + 0.05% $NH_3 \cdot H_2O$ | | |
| Solvent B | MeCN | | |
| Gradient | Time | A% | B% |
| | 0 | 85 | 15 |
| | 3.4 | 0 | 100 |
| | 4 | 0 | 100 |
| | 4.01 | 85 | 15 |
| | 4.5 | 85 | 15 |

SFC Method 1: Apparatus: Agilent 1260 with DAD Detector

| Column | Chiralpak AS-3 150 × 4.6 mm I.D., 3 um | |
|---|---|---|
| Flow rate | 2.5 mL/min | |
| Run time | 10 min. | |
| Wavelength | 220 nm | |
| Column temp | 40° C. | |
| Solvent A | EtOH + 0.05% diethylamine | |
| Gradient | Time (min) | A% |
| | 0 | 5 |
| | 5.5 | 40 |
| | 8.5 | 40 |
| | 8.51 | 5 |
| | 10 | 5 |

SFC Method 2: Apparatus: Waters UPC2

| Column | Chiralpak AD-3 150 × 4.6 mm I.D., 3 um | |
|---|---|---|
| Flow rate | 2.5 mL/min | |
| Run time | 10 min. | |
| Wavelength | 210 nm | |
| Column temp | 35° C. | |
| Solvent A | EtOH + 0.05% diethylamine | |
| Gradient | Time (min) | A% |
| | 0 | 5 |
| | 5 | 40 |
| | 7.5 | 40 |
| | 7.51 | 5 |
| | 10 | 5 |

SFC Method 3: Apparatus: Waters UPC2

| Column | Chiralpak AD-3 150 × 4.6 mm I.D., 3 um |
|---|---|
| Flow rate | 2.5 mL/min |
| Run time | 10 min. |
| Wavelength | 220 nm |
| Column temp | 35° C. |
| Solvent A | EtOH + 0.05% diethylamine |
| Gradient | Time (min) | A% |
| | 0 | 5 |
| | 5 | 5 |
| | 5.01 | 40 |
| | 7.5 | 40 |
| | 7.01 | 5 |
| | 10 | 5 |

SFC Method 4: Apparatus: Agilent 1260

| Column | Lux Cellulose-2 150 × 4.6 mm I.D., 3μm | |
|---|---|---|
| Flow rate | 2.5 mL/min | |
| Run time | 10 min. | |
| Wavelength | 220 nm | |
| Column temp | 40° C. | |
| Solvent A | MeOH + 0.05% diethylamine | |
| Gradient | Time (min) | A % |
| | 0 | 5 |
| | 5.5 | 40 |
| | 8.5 | 40 |
| | 8.51 | 5 |
| | 10 | 5 |

SFC Method 5: Apparatus: Agilent 1260

| Column | (R, R)Whelk-01 100 × 4.6 mm I.D., 3 um | |
|---|---|---|
| Flow rate | 2.5 mL/min | |
| Run time | 10 min. | |
| Wavelength | 254 nm | |
| Column temp | 40° C. | |
| Solvent A | EtOH + 0.05% diethylamine | |
| Gradient | Time (min) | A % |
| | 0 | 5 |
| | 5.5 | 40 |
| | 8.5 | 40 |
| | 8.51 | 5 |
| | 10 | 5 |

SFC Method 6: Apparatus: Waters UPC2

| Column | Chiralcel OD-3 150 × 4.6 mm I.D., 3 um | |
|---|---|---|
| Flow rate | 2.5 mL/min | |
| Run time | 10 min. | |
| Wavelength | 220 nm | |
| Column temp | 35° C. | |
| Solvent A | iPrOH + 0.05% diethylamine | |
| Gradient | Time | A % |
| | 0 | 5 |
| | 5 | 40 |
| | 7.5 | 40 |
| | 7.51 | 5 |
| | 10 | 5 |

SFC method 7: Apparatus: Waters UPC2

| Column | Chiralcel OD-3 150 × 4.6 mm I.D., 3 um |
|---|---|
| Flow rate | 2.5 mL/min |
| Run time | 10 min. |

-continued

| Wavelength | 270 nm |
| --- | --- |
| Column temp | 35° C. |
| Solvent A | iPrOH + 0.05% diethylamine |

| Gradient | Time | A % |
| --- | --- | --- |
| | 0 | 5 |
| | 5 | 40 |
| | 7.5 | 40 |
| | 7.51 | 5 |
| | 10 | 5 |

SFC Method 8: Apparatus: Agilent 1260

| Column | Chiralpak IC-3 150 × 4.6 mm I.D., 3 um |
| --- | --- |
| Flow rate | 2.5 mL/min |
| Run time | 10 min. |
| Wavelength | 220 nm |
| Column temp | 40° C. |
| Solvent A | EtOH + 0.05% diethylamine |

| Gradient | Time | A % |
| --- | --- | --- |
| | 0 | 5 |
| | 5.5 | 40 |
| | 8.5 | 40 |
| | 8.51 | 5 |
| | 10 | 5 |

SFC Method 9: Apparatus: Agilent 1260

| Column | Lux Cellulose-2 150 × 4.6 mm I.D., 3 μm |
| --- | --- |
| Flow rate | 2.5 mL/min |
| Run time | 10 min. |
| Wavelength | 20 nm |
| Column temp | 40° C. |
| Solvent A | iPrOH + 0.05% diethylamine |

| Gradient | Time | A % |
| --- | --- | --- |
| | 0 | 5 |
| | 5.5 | 40 |
| | 8.5 | 40 |
| | 8.51 | 5 |
| | 10 | 5 |

SFC Method 10: Apparatus: Agilent 1260

| Column | Chiralpak AD-3 150 × 4.6 mm I.D., 3 um |
| --- | --- |
| Flow rate | 2.5 mL/min |
| Run time | 10 min. |
| Wavelength | 220 nm |
| Column temp | 40° C. |
| Solvent A | EtOH + 0.05% diethylamine |

| Gradient | Time | A % |
| --- | --- | --- |
| | 0 | 5 |
| | 5.5 | 40 |
| | 8.5 | 40 |
| | 8.51 | 5 |
| | 10 | 5 |

SFC Method 11: Apparatus: Waters UPC2

| Column | Chiralpak AS-3 150 × 4.6 mm I.D., 3 um |
| --- | --- |
| Flow rate | 2.5 mL/min |
| Run time | 10 min. |
| Wavelength | 220 nm |

-continued

| Column temp | 35° C. |
| --- | --- |
| Solvent A | iPrOH + 0.05% diethylamine |

| Gradient | Time | A % |
| --- | --- | --- |
| | 0 | 5 |
| | 5 | 40 |
| | 7.5 | 40 |
| | 7.51 | 5 |
| | 10 | 5 |

SFC Method 12: Apparatus: Agilent 1260

| Column | ChiralCel OJ-H 150 × 4.6 mm I.D., 5 um |
| --- | --- |
| Flow rate | 2.5 mL/min |
| Run time | 10 min. |
| Wavelength | 220 nm |
| Column temp | 40° C. |
| Solvent A | iPrOH + 0.05% diethylamine |

| Gradient | Time | A % |
| --- | --- | --- |
| | 0 | 5 |
| | 5.5 | 40 |
| | 8.5 | 40 |
| | 8.51 | 5 |
| | 10 | 5 |

SFC Method 13: Apparatus: Agilent 1260

| Column | ChiralPak AY-3 150 × 4.6 mm I.D., 3 um |
| --- | --- |
| Flow rate | 2.5 mL/min |
| Run time | 10 min. |
| Wavelength | 220 nm |
| Column temp | 40° C. |
| Solvent A | EtOH + 0.05% diethylamine |

| Gradient | Time | A % |
| --- | --- | --- |
| | 0 | 5 |
| | 5.5 | 40 |
| | 8.5 | 40 |
| | 8.51 | 5 |
| | 10 | 5 |

SFC Method 14: Apparatus: Agilient 1260

| Column | Lux Cellulose-2 150 × 4.6 mm I.D., 3 μm |
| --- | --- |
| Flow rate | 2.5 mL/min |
| Run time | 4 min. |
| Wavelength | 220 nm |
| Column temp | 40° C. |
| Solvent A | EtOH + 0.05% diethylamine |

| Gradient | Time | A % |
| --- | --- | --- |
| | 0 | 5 |
| | 4 | 5 |

SFC Method 15: Apparatus: Agilent 1260

| Column | Lux Cellulose-2 150 × 4.6 mm I.D., 3 μm |
| --- | --- |
| Flow rate | 2.5 mL/min |
| Run time | 10 min. |
| Wavelength | 220 nm |
| Column temp | 40° C. |
| Solvent A | MeOH + 0.05% diethylamine |

| Gradient | Time | A % |
| --- | --- | --- |
| | 0 | 5 |
| | 10 | 5 |

SFC Method 16: Apparatus: Agilent 1260

| Column | Lux Cellulose-2 150 × 4.6 mm I.D., 3 μm |
|---|---|
| Flow rate | 2.5 mL/min |
| Run time | 10 min. |
| Wavelength | 220 nm |
| Column temp | 40° C. |
| Solvent A | EtOH + 0.05% diethylamine |

| Gradient | Time | A % |
|---|---|---|
| | 0 | 5 |
| | 5.5 | 40 |
| | 8.5 | 40 |
| | 8.51 | 5 |
| | 10 | 5 |

Chiral HPLC Method 1: Apparatus: SHIMADZU LC-20AB

| Column | CD-PH 250 × 4.6 mm I.D., 5 um |
|---|---|
| Flow rate | 0.8 mL/min |
| Run time | 30 min. |
| Wavelength | 280 nm |
| Column temp | 30° C. |
| Solvent A | Water + 0.069% TEA |
| Solvent B | MeCN |

| Gradient | Time (min) | A % | B % |
|---|---|---|---|
| | 0 | 90 | 10 |
| | 15 | 20 | 80 |
| | 17 | 90 | 10 |
| | 30 | 90 | 10 |

Chiral HPLC Method 2: Apparatus: SHIMADZU LC-20AB

| Column | OD-RH 150 × 4.6 mm I.D., 5 um |
|---|---|
| Flow rate | 0.8 mL/min |
| Run time | 25 min. |
| Wavelength | 220 nm |
| Column temp | 30° C. |
| Solvent A | Water + 0.07% TEA |
| Solvent B | MeCN |

| Gradient | Time | A % | B % |
|---|---|---|---|
| | 0 | 90 | 10 |
| | 14 | 20 | 80 |
| | 15 | 90 | 10 |
| | 25 | 90 | 10 |

General procedures for synthesis of intermediates and the compounds of general Formula I are described in reaction Scheme 1, and are specifically illustrated in the preparations and Examples. Within the scope of the present invention are variations of the described procedures, which are known to a person skilled in the art.

The compounds of the invention are prepared as described in Scheme 1. Several of the compounds of general Formula I contain two chiral carbon atoms, and are formed as a mixture of diastereomers. When this is the case, the diastereomers may be separated, to yield the single stereoisomers Ia and Ib.

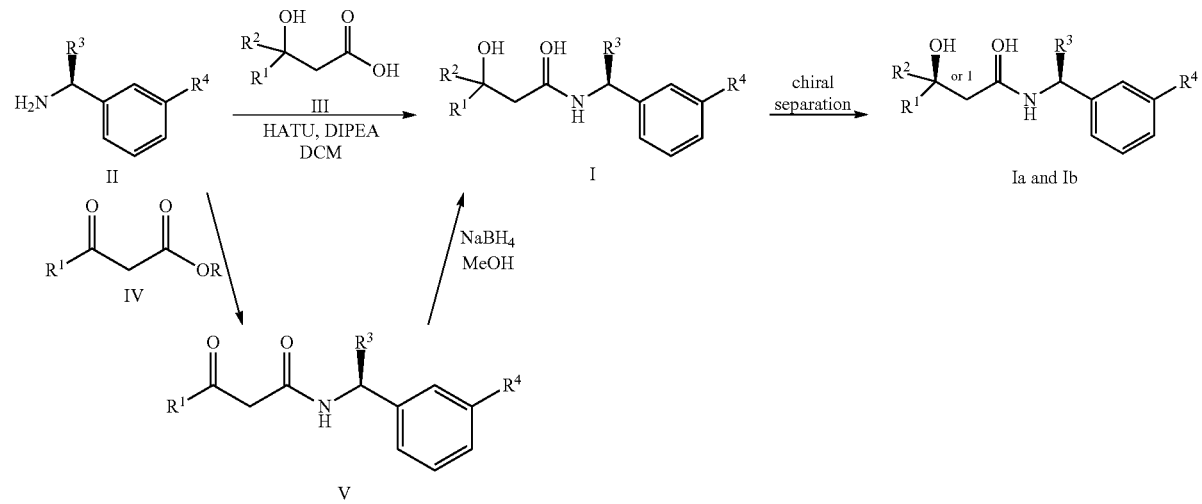

Scheme 1

Scheme I depicts the preparation of the compounds of general Formula I by two general routes. The first route is the synthesis of compounds of Formula I by reaction of an enantiomerically pure amine of general Formula II, and an acid of general Formula III, through methodology well known in the art for the conversion of an acid and an amine into an amide. This methodology includes the formation of reactive derivatives of the acid of Formula III, including, but not limited to, activated esters and reactive mixed anhydrides, followed by condensation with amines of general Formula II. One such methodology is performing the condensation in the presence of HATU ((1-[bis(dimethylamino)methylene]-1H-1,2,3-triazolo[4,5-b]pyridinium 3-oxid hexafluorophosphate) and a suitable base such as DIPEA (diisopropylethylamine), in a solvent such as dichloromethane.

Alternatively, when $R^2$ is H, the compounds of general Formula I can be prepared via a second general route, in which intermediates of general formula V, are treated with a suitable reducing agent such as $NaBH_4$, in a suitable solvent such as methanol. The intermediates of formula V can be obtained from enantiomerically pure amines of general Formula II, and a carboxylic acid of general Formula IV (R═H). This transformation can be effected using similar reaction conditions as described above for the condensation of II and III to form I.

A variation of this procedure is the direct coupling reaction between a chiral amine of general Formula II and a carboxylic acid ester of general Formula IV (R=Me, Et). This reaction can be performed by heating the reactants to reflux in a suitable solvent such as toluene, in the presence of a suitable base such as DIPEA, and in the presence of a catalytic amount of a suitable catalyst such as DMAP (4-dimethylamino pyridine).

The optically active amines of general Formula II can be prepared as outlined in Scheme 2:

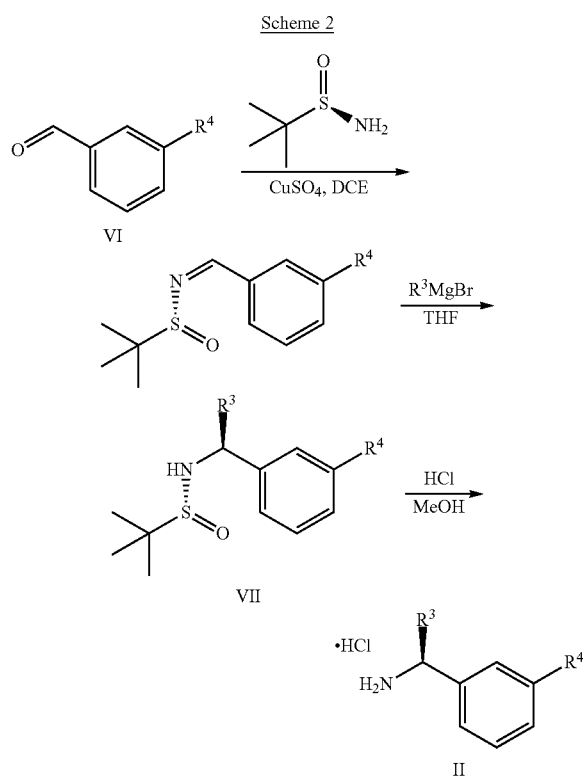

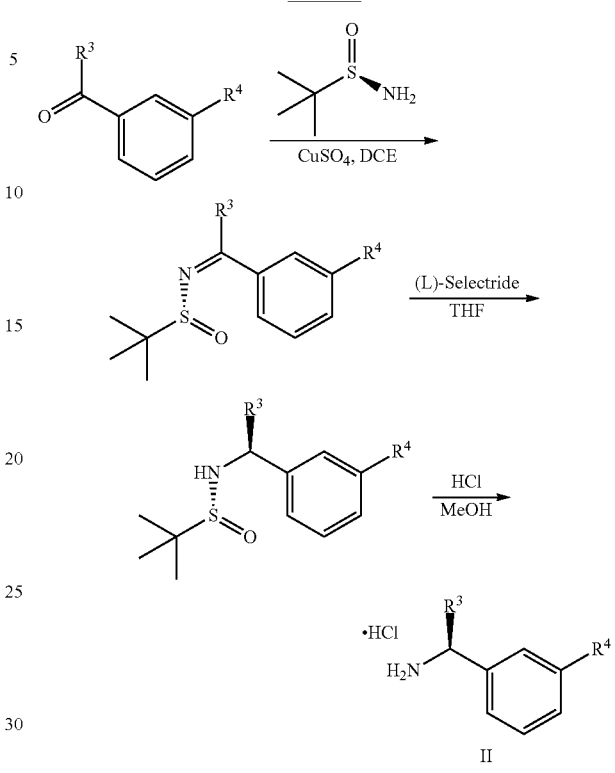

Aldehydes of general formula VI can be condensed with (R)-2-methylpropane-2-sulfinamide in a suitable solvent such as dichloroethane, in the presence of a drying agent, such as titanium(IV)isopropoxide, or cupric sulfate. The formed sulfinyl imine is treated with $R^3$MgBr in a suitable inert solvent such as THF, to yield the corresponding substituted (R)-2-methyl-N—((S)-1-aryl-alkyl)propane-2-sulfinamides VII, which are converted to the compounds of general Formula II by treatment with an appropriate acid in an appropriate solvent, such as HCl in MeOH.

The aldehydes of formula VI, used to prepare the compounds of the invention, are commercially available, or may be prepared as described in the literature, see fx. Journal of Medicinal Chemistry, 45(18), 3891-3904; 2002.

In a variation of this procedure, the chiral amines of Formula II can be obtained from an aryl ketone, through hydride reduction of the intermediate sulfinyl imine with a reagent such as L-Selectride; as shown in Scheme 3.

The ketones used to prepare the compounds of the invention, are commercially available, or may be prepared by methods known to the person skilled in the art.

Another variation of this procedure, particularly suited for accessing chiral amines of general Formula II, in which $R^3$ is a hydroxymethylene derivative, is outlined in Scheme 4.

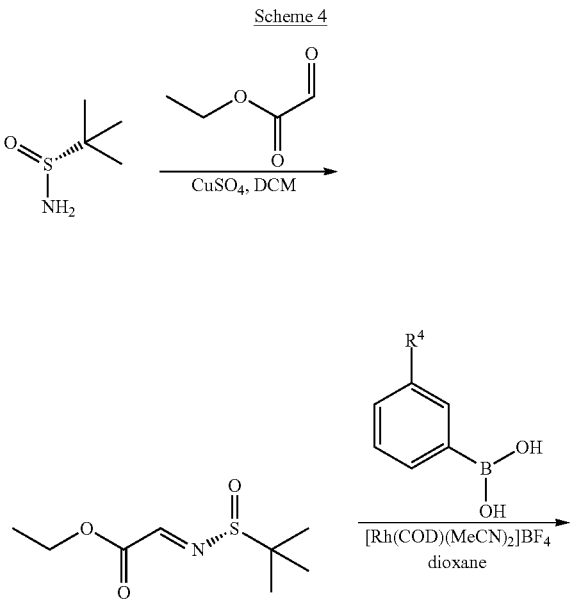

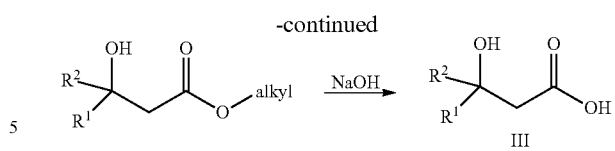

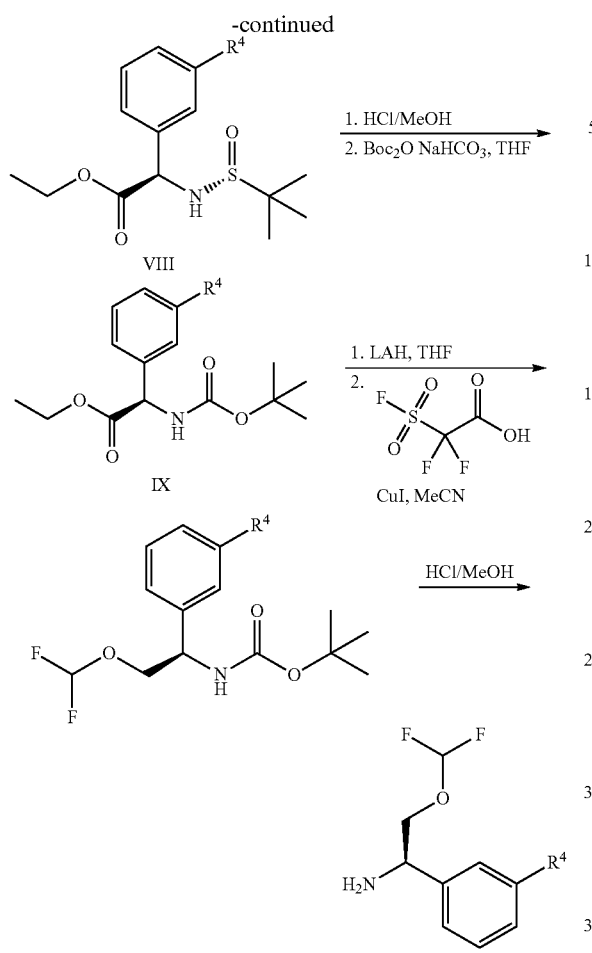

In this procedure, glyoxylate sulfinyl imine, formed in a condensation reaction between a glyoxylic ester and (R)-2-methylpropane-2-sulfinamide, can be reacted with a suitably substituted boronic acid using a suitable catalyst such as bis(acetonitrile) (1,5-cyclooctadiene)rhodium(I) tetra-fluoroborate, in a suitable solvent such as dioxane, as described in JP 2017/095366A. The resulting intermediates VIII can be hydrolysed and re-protected to yield intermediates of general Formula IX, which may be further derivatised to access the desired R³ substituent. In the compounds of the invention, the carboxylic ester group of IX can be reduced to hydroxymethylene using LAH (lithium aluminium hydride), and difluoromethylated using a suitable reagent such as 2,2-difluoro-2-(fluorosulfonyl) acetic acid under conditions such as CuI catalysis, in a suitable solvent such as acetonitrile. The skilled artisan will recognise that other transformations are possible from intermediates of general Formula IX; the present invention is intended to include such alternative transformations.

The carboxylic acids of general Formula III can be prepared as outlined in Scheme 5:

Scheme 5

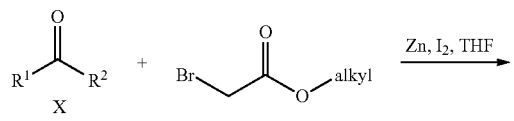

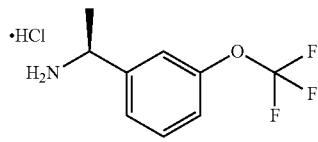

Ketones of general formula X are reacted with an alkyl ester of bromoacetic acid activated with for example Zn and iodine, to yield the corresponding aldol adduct. In an alternative procedure, the bromoacetic acid ester can be activated using Zn and TMSCl (trimethylsilylchloride). In a final step, hydrolysis of the alkyl ester is accomplished by treatment with an appropriate base such as NaOH or LiOH in an appropriate solvent, such as water, or an alcohol in water, and followed by acidification with an appropriate acid to yield the compounds of Formula III.

Preparation of Intermediates

IIa: (S)-1-(3-(Trifluoromethoxy)phenyl) ethanamine hydrochloride

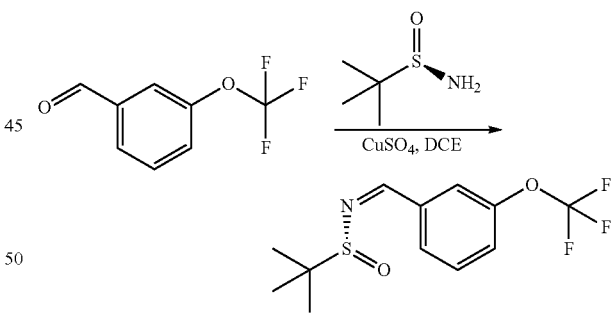

Step 1: Preparation of (R)-2-methyl-N-(3-(trifluoromethoxy) benzylidene)propane-2-sulfinamide A mixture of 3-(trifluoromethoxy)benzaldehyde (24.8 g, 130.4 mmol), (R)-2-methylpropane-2-sulfinamide (19 g, 156.5 mmol) and CuSO₄ (31.2 g, 195.7 mmol) in DCE (1,2-dichloroethane) (500 mL) was stirred at 55° C. for 24 hours. The mixture was filtered and the filter cake was washed with DCM (dichloromethane) (200 mL). The organic phases were combined and concentrated. The residue was purified by flash silica gel chromatography with an eluent of 0~15% ethyl acetate/petroleum ether (gradient) to yield the product (33 g, 86% yield).

¹H NMR (CDCl₃ 400 MHz): δ 8.59 (s, 1H), 7.79-7.71 (m, 2H), 7.53 (t, J=8.0 Hz, 1H), 7.38 (d, J=8.0 Hz, 1H), 1.28 (s, 9H).

Step 2: Preparation of (R)-2-methyl-N—((S)-1-(3-(trifluoromethoxy)phenyl)ethyl)propane-2-sulfinamide

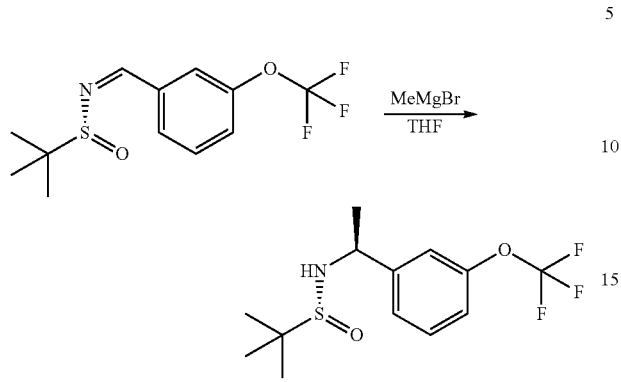

To a solution of (R)-2-methyl-N-[[3-(trifluoromethoxy)phenyl]methylene]propane-2-sulfinamide (17.6 g, 59.8 mmol) in DCM (250 mL) was added MeMgBr (3M in Et$_2$O, 40 mL) dropwise at 0° C. The resulting mixture was stirred at 0° C. for 1 hour and 15° C. for 16 hours. The mixture was cooled to 0° C., and sat. NH$_4$Cl solution was added. The resulting mixture was extracted with DCM (100 mL×2). The organic phases were washed with brine (200 mL), dried over Na$_2$SO$_4$ and concentrated. The residue was purified by flash silica gel chromatography with an eluent of 0~50% ethyl acetate/petroleum ether (gradient) to give the product (10.3 g, 56% yield).

$^1$H NMR (CDCl$_3$ 400 MHz): δ 7.37 (t, J=8.0 Hz, 1H), 7.27-7.24 (m, 1H), 7.21 (s, 1H), 7.13 (br d, J=8.0 Hz, 1H), 4.65-7.59 (m, 1H), 3.32 (br d, J=2.4 Hz, 1H), 1.54 (d, J=6.4 Hz, 3H), 1.22 (s, 9H).

Step 3: Preparation of (S)-1-(3-(trifluoromethoxy)phenyl)ethan amine hydrochloride

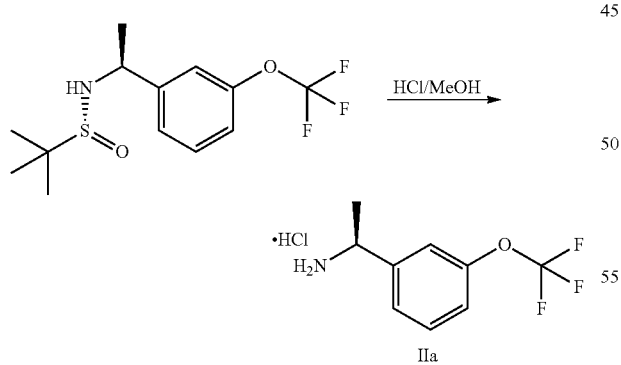

(R)-2-methyl-N-[(1S)-1-[3-(trifluoromethoxy)phenyl] ethyl]propane-2-sulfinamide (10 g, 32.3 mmol) in MeOH (75 mL) was treated with HCl/MeOH (75 mL) and stirred at 15° C. for 16 hours. The mixture was concentrated to give (S)-1-(3-(trifluoromethoxy)phenyl)ethanamine hydrochloride (9 g, crude) which was used directly without further purification.

IIb: (1S)-1-[3-(2,2,2-Trifluoroethoxy)phenyl] ethanamine hydrochloride

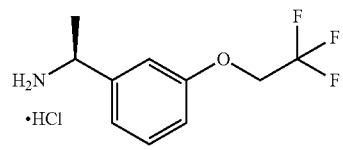

Step 1: Preparation of 3-(2,2,2-trifluoroethoxy)benzaldehyde

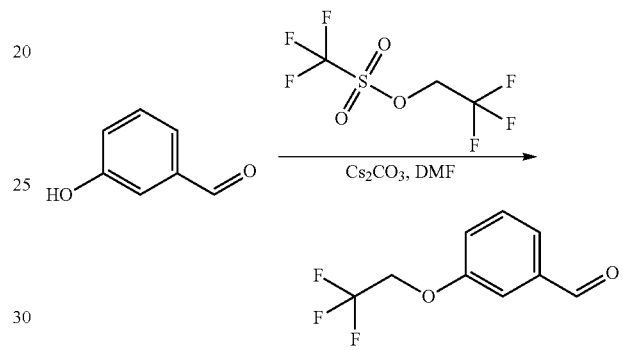

A mixture of 3-hydroxybenzaldehyde (5 g, 40.9 mmol), 2,2,2-trifluoroethyl trifluoromethanesulfonate (10.5 g, 45 mmol) and Cs$_2$CO$_3$ (26.7 g, 81.9 mmol) in DMF (60 mL) was stirred at 20° C. for 2 hours. The mixture was filtered and the filter cake was washed with ethyl acetate (200 ml). The filtrate was washed with water (100 mL×2) and brine (100 mL×2), dried over Na$_2$SO$_4$ and concentrated. The crude was purified by column chromatograph on silica gel (20% ethyl acetate in petroleum ether) to give the product (8.0 g, 95% yield).

$^1$H NMR (CDCl$_3$ 400 MHz): δ 7.58-7.51 (m, 2H), 7.42 (s, 1H), 7.27-7.25 (m, 1H), 4.42 (q, J=12.0 Hz, J=8.0 Hz, 2H).

Step 2: Preparation of (R)-2-methyl-N-[[3-(2,2,2-trifluoro-ethoxy)phenyl]methylene]propane-2-sulfinamide

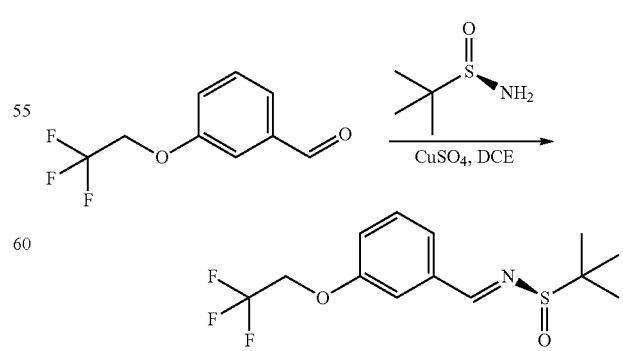

A mixture of 3-(2,2,2-trifluoroethoxy)benzaldehyde (8.0 g, 39.2 mmol), (R)-2-methylpropane-2-sulfinamide (5.2 g, 43.1 mmol) and CuSO₄ (9.4 g, 58.8 mmol) in DCE (70 mL) was stirred at 55° C. for 20 hours. The mixture was filtered and the filter cake was washed with DCM (100 mL). The organic phases were concentrated and purified by column chromatograph on silica gel (11% ethyl acetate in petroleum ether) to yield the product (10.0 g, 83% yield).

¹H NMR (CDCl₃ 400 MHz): δ 8.55 (s, 1H), 7.50-7.42 (m, 3H), 7.13 (d, J=5.2 Hz, 1H), 4.41 (q, J=12.0 Hz, J=8.0 Hz, 2H), 1.27 (s, 9H).

Step 3: Preparation of (R)-2-methyl-N—((S)-1-(3-(2,2,2-trifluor oethoxy)phenyl)ethyl)propane-2-sulfinamide

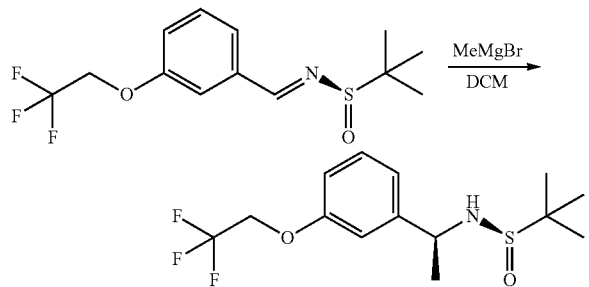

To a solution of (R)-2-methyl-N-[[3-(2,2,2-trifluoroethoxy)phenyl]methylene]propane-2-sulfinamide (10 g, 32.5 mmol) in DCM (100 mL) at 0° C. was added MeMgBr (3M, 43 mL) dropwise. The resulting mixture was stirred at 0° C. for 1 hour and 20° C. for 3 hours. The mixture was cooled to 0° C., and sat. NH₄Cl solution was added. The resulting mixture was extracted with DCM (100 mL×2). The organic phases were washed with brine (200 mL), dried over Na₂SO₄ and concentrated. The crude was purified by column chromatograph on silica gel (petroleum ether:ethyl acetate=1:1) to give the product (9 g, 79% yield).

¹H NMR (CDCl₃ 400 MHz): δ 7.27 (d, J=8.4 Hz, 1H), 7.01 (d, J=8.4 Hz, 1H), 6.93 (d, J=2.4 Hz, 1H), 6.83 (dd, J=8.4 Hz, J=2.4 Hz, 1H), 4.56-4.54 (m, 1H), 4.34 (dd, J=16.4 Hz, J=8.4 Hz, 1H), 3.30 (br s, 1H), 1.51 (d, J=8.4 Hz, 3H), 1.20 (s, 9H). NH is not observed.

Step 4: Preparation of (1S)-1-[3-(2,2,2-trifluoroethoxy)phenyl]ethanamine hydrochloride

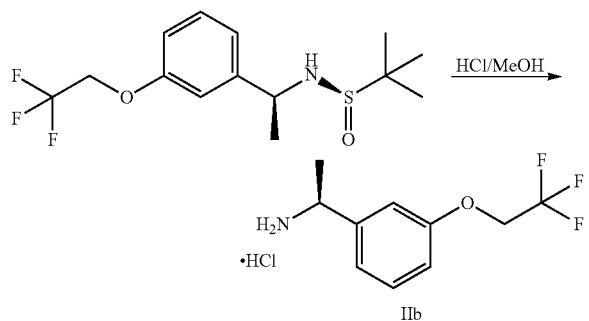

To a solution of (R)-2-methyl-N-[(1S)-1-[3-(2,2,2-trifluoroethoxy)phenyl]ethyl]propane-2-sulfinamide (9 g, 27.8 mmol) in MeOH (100 mL) was added HCl/MeOH (80 mL, 4M). The resulting mixture was stirred at 20° C. for 4 hours, and was concentrated to give the crude product (8 g), which was used directly without further purification.

IIc: (S)-1-(3-(Difluoromethoxy)phenyl) ethan-1-amine hydrochloride

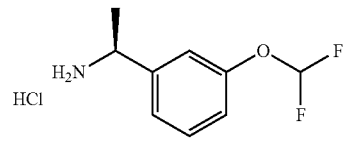

Step 1: Preparation of (R)—N-(3-(difluoromethoxy) benzylidene)-2-methylpropane-2-sulfinamide

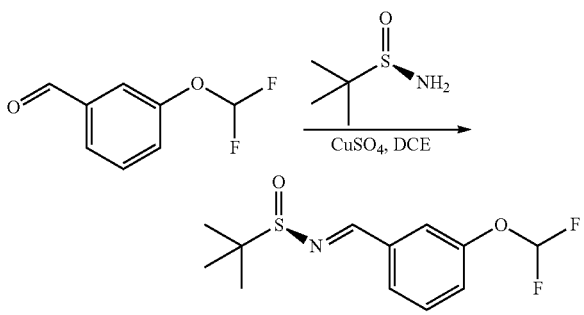

To a mixture of 3-(difluoromethoxy)benzaldehyde (2 g, 11.6 mmol) and 2-methylpropane-2-sulfinamide (1.7 g, 13.9 mmol) in DCE (60 mL) was added CuSO₄ (9.3 g, 58.1 mmol) at 55° C. under N2. The mixture was stirred at 55° C. for 12 hours, filtered and the filtrated was concentrated. The crude product was purified by silica gel column eluted with petroleum ether/Ethyl acetate=20:1-10:1 to give (R)—N-(3-(difluoromethoxy)benzylidene)-2-methylpropane-2-sulfinamide (2.5 g, 70% yield).

Step 2: Preparation of (R)—N—((S)-1-(3-(difluoromethoxy) phenyl)ethyl)-2-methylpropane-2-sulfinamide

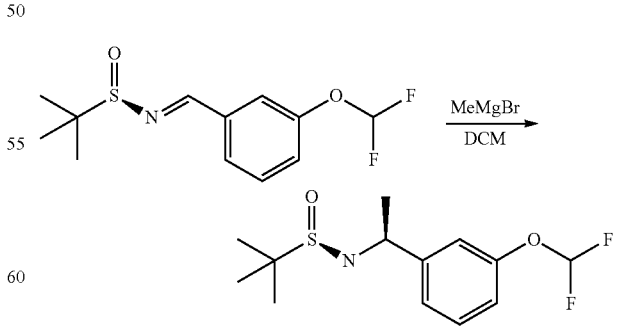

To a solution of (R)—N-(3-(difluoromethoxy)benzylidene)-2-methylpropane-2-sulfinamide (2 g, 7.3 mmol) in DCM (30 mL) was added bromo(methyl)magnesium (3M in Et₂O, 4.8 mL) dropwise at 0° C. The resulting mixture was stirred at 0° C. for 1 hour and 20° C. for 16 hours. The reaction was quenched with NH₄Cl (sat. aq, 10 mL), and aqueous phase was extracted with ethyl acetate (30 mL×3). The combined organic phase was washed with brine (40 mL×2), dried with anhydrous Na₂SO₄, filtered, concentrated and purified by silica gel chromatography (petroleum ether/Ethyl acetate=5:1-1:1) to afford (R)—N—((S)-1-(3-(difluoromethoxy) phenyl))-2-methylpropane-2-sulfinamide (960 mg, 45.4% yield).

Step 3: Preparation of (S)-1-(3-(difluoromethoxy)phenyl)ethan amine hydrochloride

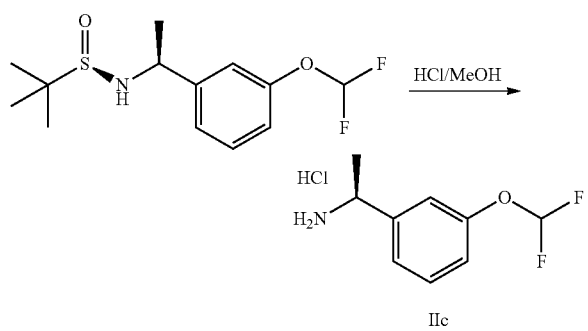

To a solution of (R)—N—((S)-1-(3-(difluoromethoxy) phenyl)ethyl)-2-methylpropane-2-sulfinamide (0.8 g, 2.8 mmol) in MeOH (4 mL) was added HCl/MeOH (4M, 2 mL). The resulting mixture was stirred at 25° C. for 3 hours, and the reaction was concentrated to afford (S)-1-(3-(difluoromethoxy)phenyl)ethan amine in 1.6 g crude yield, which was used directly without further purification.

IId: (S)-1-(3-(Trifluoromethyl)phenyl) ethan-1-amine hydrochloride

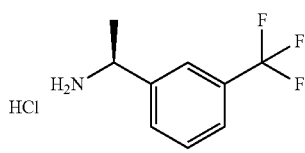

Step 1: Preparation of (R)-2-methyl-N-(3-(trifluoromethyl) benzylidene)propane-2-sulfinamide

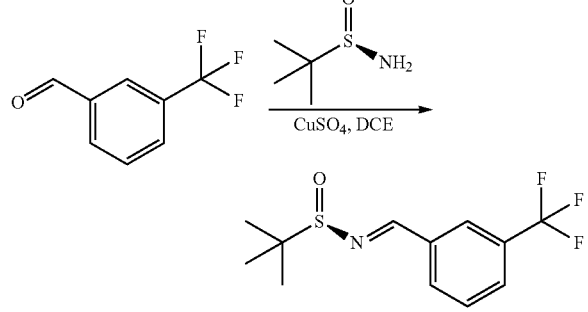

A mixture of 3-(trifluoromethyl)benzaldehyde (4.5 g, 25.8 mmol), (R)-2-methylpropane-2-sulfinamide (3.8 g, 31 mmol) and CuSO₄ (6.2 g, 38.8 mmol) in DCE (20 mL) was stirred at 55° C. for 24 hours. The mixture was filtered and filter was washed with DCM (100 mL). The filtrate was concentrated, and the residue was purified by column chromatography (SiO₂, petroleum ether/Ethyl acetate) to afford the product in 4.6 g yield (58%).

¹H NMR (CDCl₃, 400 MHz): δ 8.60 (s, 1H), 8.09 (s, 1H), 7.98 (d, J=7.6 Hz, 1H), 7.73 (d, J=7.6 Hz, 1H), 7.59 (t, J=7.6 Hz, 1H), 1.25 (s, 9H).

Step 2: Preparation of (R)-2-methyl-N—((S)-1-(3-trifluoro-methyl)phenyl)ethyl)propane-2-sulfinamide

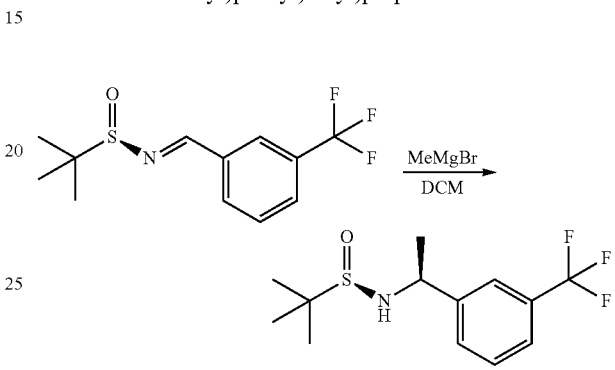

To a solution of (R)-2-methyl-N-(3-(trifluoromethyl)benzyli-dene)propane-2-sulfinamide (2 g, 7.2 mmol) in DCM (50 mL) at 0° C. MeMgBr (3M in Et₂O, 9.6 mL) was added dropwise. The resulting mixture was stirred at 0° C. for 1 hour and 25° C. for 3 hours. The reaction mixture was cooled to 0° C., and sat. aa. NH₄Cl solution was added. The mixture was extracted with DCM (50 mL×3). The combined organic phases were washed with brine (50 mL×2), dried over Na₂SO₄ and concentrated. The residue was purified by column chromatography (SiO₂, petroleum ether/Ethyl acetate) to afford the desired product (1.3 g, 61% yield).

¹H NMR (CDCl₃, 400 MHz): δ 7.40-7.65 (4H), 4.11-4.06 (m, 1H), 1.51 (d, J=6.8 Hz, 3H), 1.17 (s, 9H). NH not observed.

Step 3: Preparation of (S)-1-[3-(trifluoromethyl)phenyl]ethan amine hydrochloride

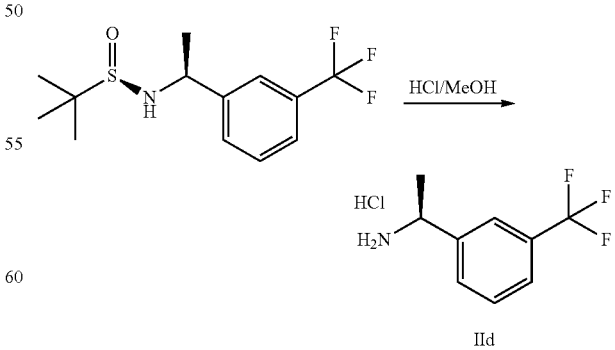

To a solution of (R)-2-methyl-N—((S)-1-(3-(trifluoromethyl) phenyl)ethyl)propane-2-sulfonamide (1.3 g, 4.4 mmol) in MeOH (20 mL) was added HCl/MeOH (4M, 20 mL). The resulting mixture was stirred at 25° C. for 20 hours, and then concentrated to afford the product in 850 mg yield. The crude was used directly without further purification.

IIe: (S)-1-(3-(trifluoromethoxy)phenyl) propan-1-amine hydrochloride

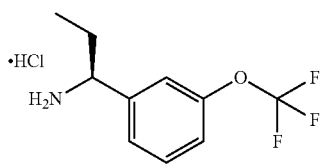

Step 1: Preparation of (R)-2-methyl-N-(3-(trifluoromethoxy) benzylidene)propane-2-sulfinamide

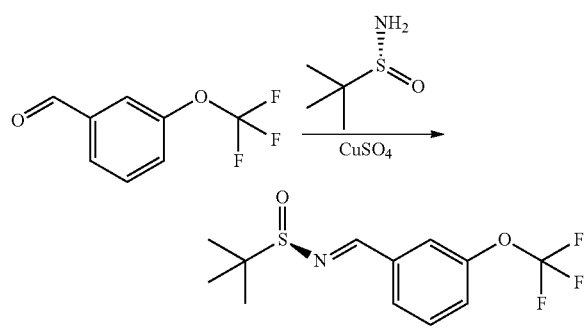

A mixture of 3-(trifluoromethoxy)benzaldehyde (10.0 g, 52.60 mmol), (R)-2-methylpropane-2-sulfinamide (7.7 g, 63.1 mmol) and CuSO4 (12.6 g, 78.9 mmol) in DCE (200 mL) was stirred at 55° C. for 16 hours. The mixture was filtered and the filter cake was washed with DCM (200 mL). The filtrate was concentrated. The residue was purified by flash chromatography on silica gel (Eluent of 0~10% Ethylacetate/petroleum ether gradient) to give (R)-2-methyl-N-[[3-(trifluoromethoxy)phenyl]methylene]propane-2-sulfinamide in a yield of 12.6 g, (81.7%).

Step 2: Preparation of (R)-2-methyl-N—((S)-1-(3-(trifluoro-methoxy)phenyl)propyl)propane-2-sulfinamide

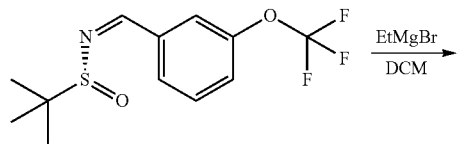

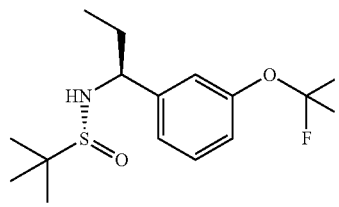

To a solution of (R)-2-methyl-N-(3-(trifluoromethoxy) benzylidene)propane-2-sulfinamide (2.0 g, 6.8 mmol) in DCM (40 mL) at 0° C. EtMgBr (3M in Et₂O, 9.1 mL) was added drop-wise. The resulting mixture was stirred at 0° C. for 1 hour and 20° C. for 3 hours. The mixture was cooled to 0° C. and sat. aq NH₄Cl (100 mL) was added. The mixture was extracted with DCM (100 mL×2), the phases were separated, and the organic layer was washed with brine (200 mL), dried over Na₂SO₄ and concentrated. The residue was purified by flash silica gel chromatography (Eluent of 0~50% Ethyl acetate/petroleum ether gradient) to yield the product (1.4 g, 62% yield).

Step 3: Preparation of (S)-1-[3-(trifluoromethoxy) phenyl]propan-1-amine hydrochloride

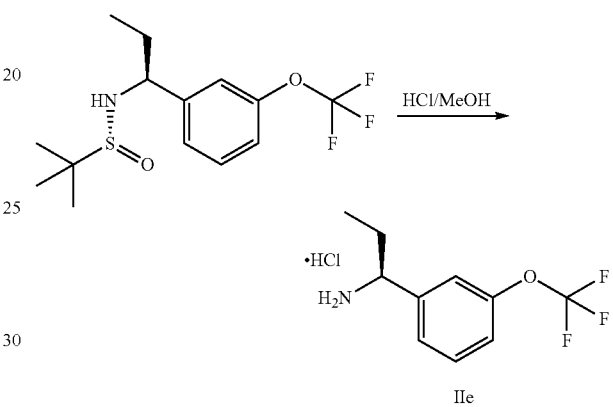

To a solution of (R)-2-methyl-N—((S)-1-(3-(trifluoromethoxy)phenyl)propyl)propane-2-sulfin amide (1.4 g, 4.2 mmol) in MeOH (40 mL) was added HCl/MeOH (4M, 20 mL). The resulting mixture was stirred at 30° C. for 12 hours and then concentrated to yield the crude (S)-1-[3-(trifluoromethoxy)phenyl]propan-1-amine hydrochloride, which was used without further purification (1 g)

IIf: (R)-2-Methoxy-1-(3-(trifluoromethoxy)phenyl) ethan-1-amine

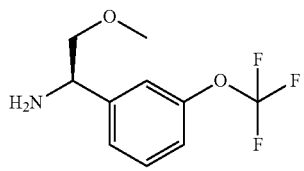 [SMILES: COC[C@H](N)c1cccc(OC(F)(F)F)c1]

Step 1: Preparation of 2-methoxy-1-(3-(trifluoromethoxy)phenyl) ethanone

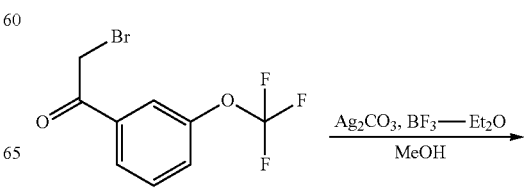

-continued

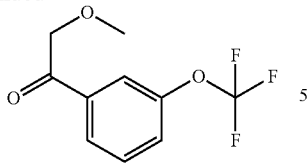

To a solution of 2-bromo-1-(3-(trifluoromethoxy)phenyl) ethanone (3.5 g, 12.4 mmol) in MeOH (60 mL) was added Ag₂CO₃ (3.8 g, 13.6 mmol) and BF₃·Et₂O (2.1 g, 14.8 mmol). The mixture was stirred at 50° C. for 16 hours under N₂. The reaction mixture was filtered and concentrated. The residue was purified by column chromatography (SiO₂, eluent of 0~5% Ethyl acetate/petroleum ether) to give 2-methoxy-1-(3-(trifluoro-methoxy)phenyl)ethanone (2.1 g, 64% yield).

¹H NMR (400 MHz, CDCl₃) δ 7.87 (d, J=8.0 Hz, 1H), 7.80 (s, 1H), 7.52 (t, J=8.4 Hz, 1H), 7.46-7.42 (m, 1H), 4.68 (s, 2H), 3.51 (s, 3H).

Step 2: Preparation of (R)—N-(2-methoxy-1-(3-(trifluoro-methoxy)phenyl)ethylidene)-2-methyl propane-2-sulfinamide

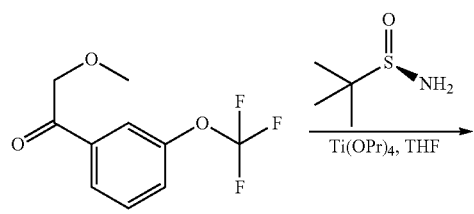

To a solution of 2-methoxy-1-(3-(trifluoromethoxy)phenyl) ethanone (500 mg, 2.1 mmol) in THF (15 mL) was added titanium(IV)isopropoxide (910 mg, 3.2 mmol) and (R)-2-methylpropane-2-sulfinamide (336 mg, 2.8 mmol). The mixture was stirred at 50° C. for 1 hour under N₂. The reaction mixture was quenched with brine (40 mL) and extracted with ethyl acetate (30 mL×2). The combined organic phases were dried over MgSO₄, filtered and concentrated. The residue was purified by column chromatography (SiO₂, eluent of 0~10% Ethyl acetate/petroleum ether) to give (R)—N-(2-methoxy-1-(3-(trifluoromethoxy)phenyl) ethylidene)-2-methylpropane-2-sulfin amide (160 mg, 20% yield).

Step 3: Preparation of (R)—N—((R)-2-methoxy-1-(3-(trifluoro-methoxy)phenyl)ethyl)-2-methyl propane-2-sulfinamide

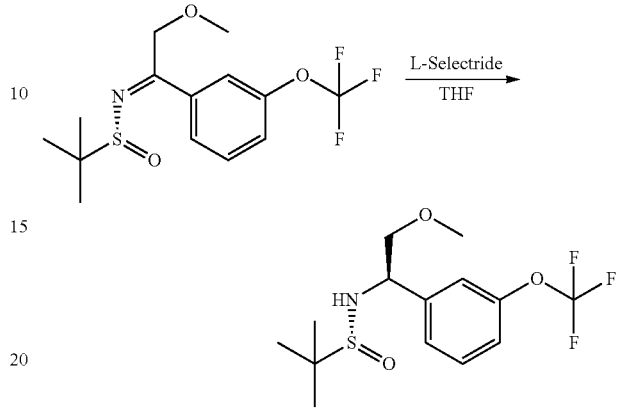

To a solution of (R)—N-(2-methoxy-1-(3-(trifluoromethoxy)phenyl)ethylidene)-2-methylpropane-2-sulfinamide (160 mg, 0.5 mmol) in THF (5 mL) was added L-selectride (1M in THF, 1.42 mmol, 1.42 mL) at 0° C. The mixture was stirred at 20° C. for 16 hours. The reaction mixture was diluted with methanol (20 mL), and then filtered and concentrated. The residue was purified by column chromatography (SiO₂, eluent of 0~10% Ethyl acetate/petroleum ether) to give the desired product (100 mg, 59% yield).

¹H NMR (400 MHz, DMSO-d⁶) δ 7.46-7.40 (m, 3H), 7.27-7.25 (m, 1H), 5.86 (d, J=8.8 Hz, 1H), 5.25 (d, J=5.6 Hz, 2H), 4.84-4.72 (m, 1H), 3.25 (s, 3H), 1.09 (s, 9H).

Step 4: Preparation of (R)-2-methoxy-1-(3-(trifluoromethoxy)phenyl) ethanamine

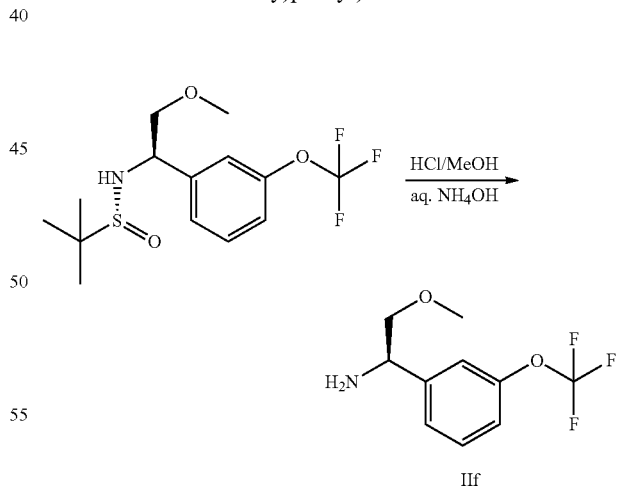

IIf (R)—N—((R)-2-methoxy-1-(3-(trifluoromethoxy)phenyl)ethyl)-2-methylpropane-2-sulfinamide (280 mg, 0.8 mmol) in HCl/MeOH (10 mL, 4M) was stirred at 20° C. for 14 hours. The reaction mixture was concentrated, and the residue diluted with water (30 mL), added ammonium hydroxide to pH=8~9 and extracted with ethyl acetate (30 mL×2). The combined organic extracts were dried over MgSO₄, filtered and concentrated to give the product as a IIg: (1R)-2-(Difluoromethoxy)-1-[3-(trifluoromethoxy)phenyl]ethanamine

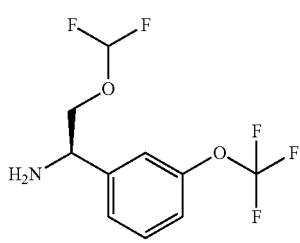 [SMILES: N[C@@H](COC(F)F)c1cccc(OC(F)(F)F)c1]

Step 1: Preparation of ethyl 2-[(R)-tert-butylsulfinyl]imino acetate

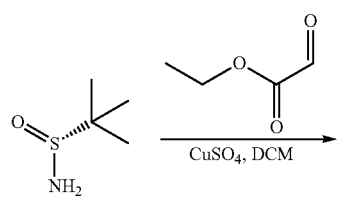

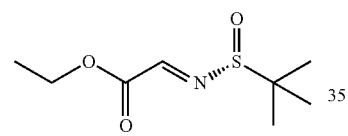

To a solution of ethyl 2-oxoacetate (7.5 g, 36.7 mmol) and (R)-2-methylpropane-2-sulfinamide (4.9 g, 40.4 mmol) in DCM (150 mL) was added CuSO$_4$ (12.9 g, 80.8 mmol), and the reaction mixture was stirred at 25° C. for 24 hours. The solid was filtered off, washed with ethyl acetate (50 mL) and the organic phases were combined and concentrated. The resulting residue was purified by column chromatography (silica gel, petroleum ether/ethyl acetate, 5/1) to yield the desired product (5.1 g, 67.6% yield).

Step 2: Preparation of ethyl (2R)-2-[[(R)-tert-butylsulfinyl]amino]-2-[3-(trifluoromethoxy)phenyl] acetate

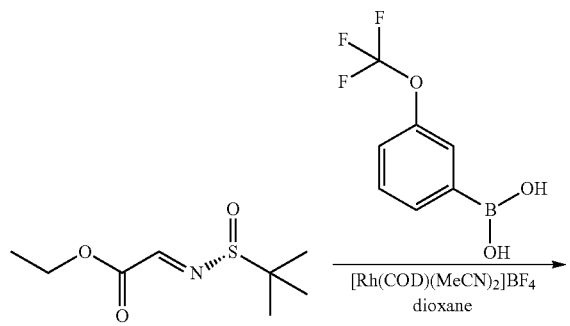

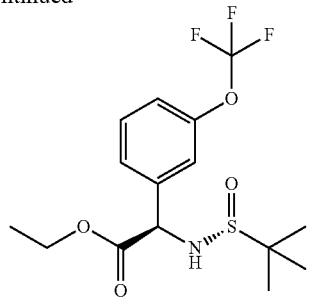

To a solution of ethyl-2-[(R)-tert-butylsulfinyl]iminoacetate (7 g, 34.1 mmol) and [3-(trifluoromethoxy)phenyl] boronic acid (8.4 g, 40.9 mmol) in dioxane (100 mL) was added [Rh(COD) (MeCN)$_2$]BF$_4$ (1.3 g, 3.4 mmol) and this mixture was stirred at 80° C. for 16 hours. The product was purified by silica gel chromatography (petroleum ether:ethyl acetate=5:1) to yield 9.8 g (78%).

Step 3: Preparation of ethyl (2R)-2-amino-2-[3-(trifluoro-methoxy)phenyl]acetate hydrochloride To a solution of ethyl (2R)-2-[[(R)-tert-butylsulfinyl] amino]-2-[3-(trifluoromethoxy)phenyl] acetate (9.8 g, 26.7 mmol) in MeOH (100 mL), was added HCl/MeOH (4 M, 100 mL) and this mixture was stirred at 25° C. for 2 hours, and then concentrated to afford ethyl (2R)-2-amino-2-[3-(trifluoromethoxy)phenyl]acetate (7.8 g, crude).

Step 4: Preparation of ethyl (2R)-2-(tert-butoxycarbonylamino)-2-[3-(trifluoromethoxy)phenyl] acetate

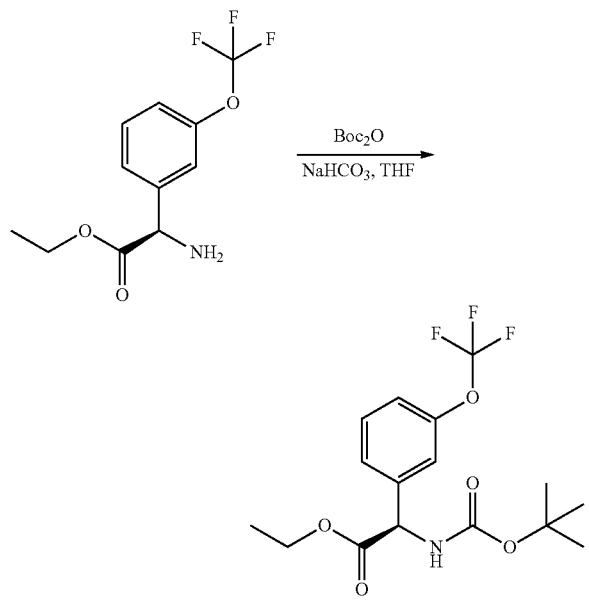

To a mixture of ethyl (2R)-2-amino-2-[3-(trifluoromethoxy)phenyl]acetate hydrochloride (6 g, 20 mmol) in THF (150 mL), was added Boc₂O (8.7 g, 40 mmol). Then NaHCO₃ (1.7 g, 20 mmol) was added to this solution and stirred at 25° C. for 16 hours. This mixture was concentrated and purified by chromatography on silica (petroleum ether: ethyl acetate=10:1) to afford the product (7.2 g, 99% yield).

Step 5: Preparation of tert-butyl N-[(1R)-2-hydroxy-1-[3-(trifluoromethoxy)phenyl]ethyl]carbamate

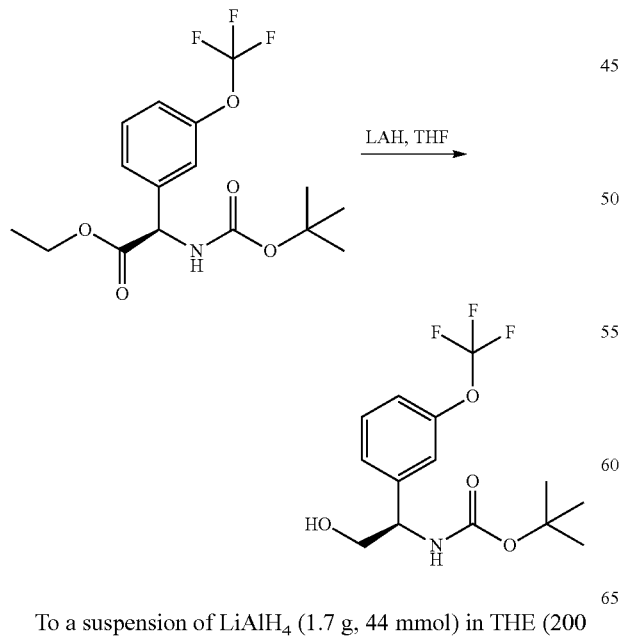

To a suspension of LiAlH₄ (1.7 g, 44 mmol) in THF (200 mL) was added ethyl (2R)-2-(tert-butoxycarbonylamino)-2-[3-(trifluoro-methoxy)phenyl]acetate (4 g, 11 mmol) in THF (25 mL), with ice-cooling. Following addition, the reaction was allowed to warm to 25° C. and was stirred for 2 hours. Anhydrous magnesium sulfate was added and then one drop of water and ethyl acetate were successively added. Insoluble substances were filtered off through a pad of celite. The filtrate was concentrated and purified by chromatography on silica (SiO₂; petroleum ether:ethyl acetate=5:1) (2.1 g, 59% yield).

Step 6: Preparation of tert-butyl N-[(1R)-2-(difluoromethoxy)-1-[3-(trifluoromethoxy)phenyl]ethyl] carbamate

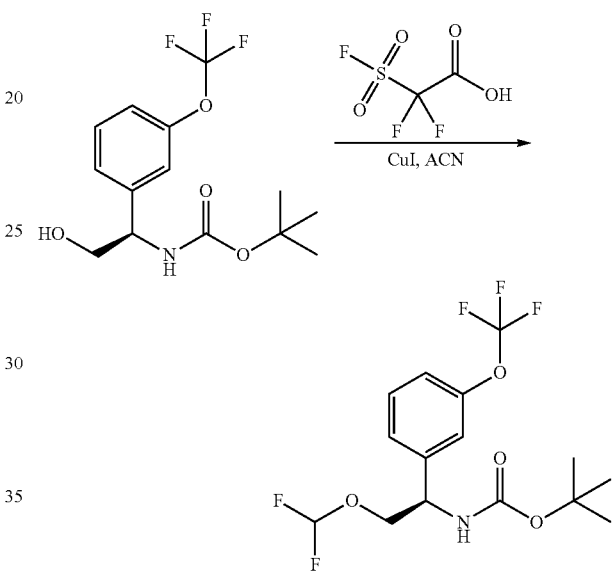

To a solution of tert-butyl N-[(1R)-2-hydroxy-1-[3-(trifluoro-methoxy)phenyl]ethyl] carbamate (1.5 g, 4.7 mmol) in MeCN (20 mL), CuI (360 mg, 1.9 mmol) was added and stirred at 25° C. under N₂ atmosphere for 30 minutes. Subsequently, a solution of 2,2-difluoro-2-fluorosulfonyl-acetic acid (1.7 g, 9.3 mmol) in MeCN (5 mL) was added at 45° C. over 30 minutes, and the reaction was stirred at 45° C. for 1 hour. This mixture was concentrated and then diluted by ethyl acetate (100 mL), filtered and concentrated to afford the desired product (1.5 g, crude).

Step 7: Preparation of (1R)-2-(difluoromethoxy)-1-[3-(trifluoromethoxy)phenyl]ethanamine

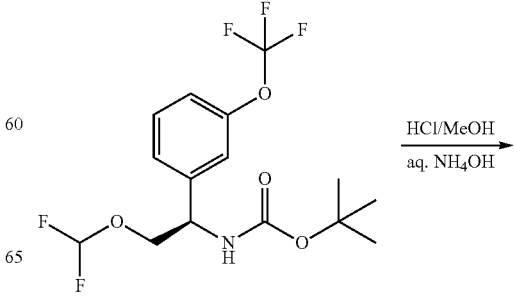

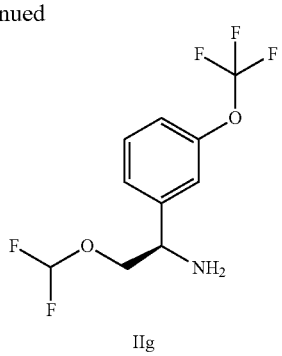

IIg

To a solution of tert-butyl N-[(1R)-2-(difluoromethoxy)-1-[3-(trifluoromethoxy)phenyl]ethyl]carbamate (1.5 g, 4 mmol) in MeOH (15 mL), was added HCl/MeOH (4M in MeOH, 30 mL) at 25° C., and the reaction was stirred at 25° C. for 30 minutes. Ammonium hydroxide (30%) was added to pH-9, and this solution was concentrated and purified by chromatography on silica (SiO₂; petroleum ether:ethyl acetate=2:1) to afford (1R)-2-(difluoromethoxy)-1-[3-(trifluoromethoxy)phenyl]ethanamine (700 mg, 64% yield).

IIIa: 2-(1-Hydroxycyclobutyl)acetic acid

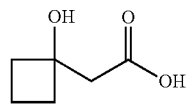

Step 1: Preparation of ethyl 2-(1-hydroxycyclobutyl)acetate

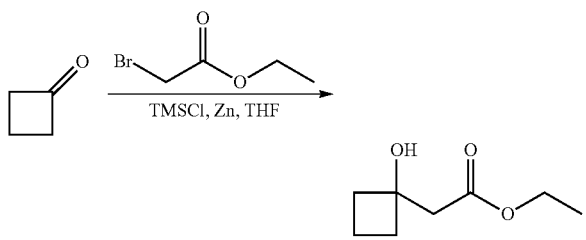

Zn (14.9 g, 228.3 mmol) in THF (20 mL) was added TMSCl (1.9 g, 17.1 mmol) in portions. The resulting mixture was stirred at 20° C. for 15 min and then refluxed. The reaction mixture was cooled to room temperature, and ethyl 2-bromoacetate (28.6 g, 171.2 mmol) was added dropwise at such a rate that the reaction boiled gently. The resulting mixture was stirred at 70° C. for 1 hour and then at 20° C. for 1 hour, then a solution of cyclobutanone (10 g, 142.7 mmol) in THF (5 mL) was added. The mixture was stirred at 20° C. for another 2 hours. The mixture was poured into NH₃·H₂O (150 mL, 25%) on ice and extracted with ethyl acetate (100 mL×2). The organic layer was washed with water (200 mL×2) and brine (100 ml×2), dried over Na₂SO₄ and concentrated to give the product (12 g, crude).

¹H NMR (CDCl₃ 400 MHz): δ 4.20-4.14 (m, 2H), 3.69 (s, 1H), 2.65 (s, 2H), 2.17-2.12 (m, 2H), 2.03-2.00 (m, 2H), 1.78 (m, 1H), 1.58 (m, 1H), 1.27 (t, J=7.6 Hz, 3H).

Step 2: Preparations of 2-(1-hydroxycyclobutyl)acetic acid

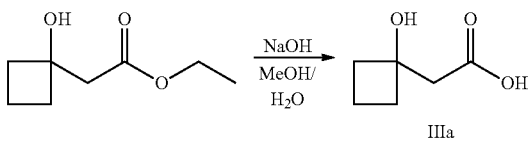

NaOH (6.3 g, 158.05 mmol) was dissolved in MeOH (150 mL) and H₂O (50 mL), and ethyl 2-(1-hydroxycyclobutyl)acetate (10 g, 63.2 mmol) was added. The mixture was stirred at 20° C. for 16 hours and then concentrated, and the residue was acidified by 2N HCl solution to pH=2-3 and extracted with ethyl acetate (200 ml×2). The organic extract was washed with water (100 mL×2) and brine (100 mL×2), dried over Na₂SO₄ and concentrated to give the crude product (6 g, crude).

¹H NMR (CDCl₃ 400 MHz): δ 2.74 (s, 2H), 2.23-2.05 (m, 4H), 1.81 (m, 1H), 1.63-1.58 (m, 1H).

IIIb: 2-(3,3-Difluoro-1-hydroxycyclobutyl)acetic acid

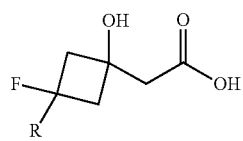

Step 1: Preparation of ethyl 2-(3,3-difluoro-1-hydroxy-cyclobutyl)acetate

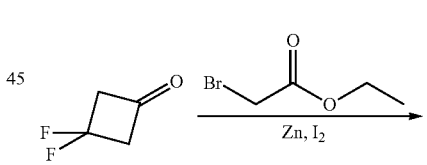

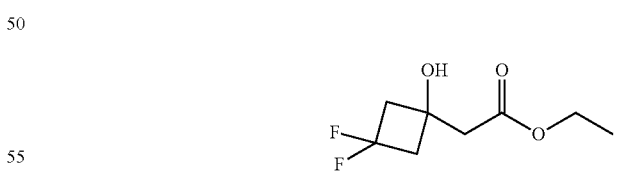

To a solution of 3,3-difluorocyclobutanone (0.2 g, 1.9 mmol), Zn (198 mg, 3 mmol) and I₂ (10 mg, 0.04 mmol) in THF (13 mL) under N₂, ethyl 2-bromoacetate (378 mg, 2.3 mmol) was added dropwise. The mixture was stirred at 55° C. for 6 hours. H₂SO₄ (10%, 10 mL) was carefully added to the reaction mixture at 0° C., and the mixture was extracted with ethyl acetate (20 mL×3). The organic extract was washed with NaHCO₃ (sat. aq, 10 mL), dried over Na₂SO₄ and concentrated. The crude product (0.26 g) was used directly without further purification.

Step 2: Preparation of 2-(3,3-difluoro-1-hydroxy-cyclobutyl) acetic acid

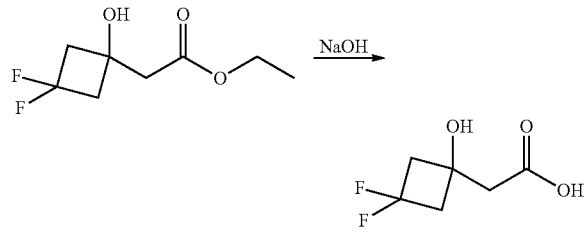

IIIb

To a solution of ethyl 2-(3,3-difluoro-1-hydroxy-cyclobutyl) acetate (0.26 g, 1.3 mmol) in MeOH (10 mL) and H$_2$O (2 mL), NaOH (107 mg, 2.7 mmol) was added at 0° C. The mixture was stirred at 20° C. for 8 hours. The reaction solution was cooled to 0° C. and 1N HCl was added to the solution until pH reached 1-2. The residue was diluted with brine (10 mL) and extracted with methyl-tert-butyl ether (30 mL×5). The combined organic extracts were dried over Na$_2$SO$_4$, filtered and concentrated. The crude product (0.24 g) was used without further purification.

IIIc: 3-Hydroxy-4-methyl-3-(trifluoromethyl)pentanoic acid

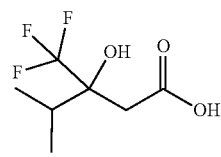

Step 1: Preparation of ethyl 3-hydroxy-4-methyl-3-(trifluoro-methyl)pentanoate

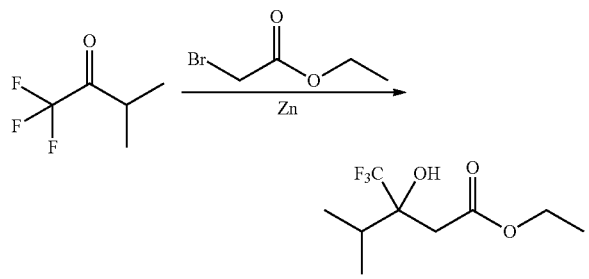

To a mixture of Zn (560 mg, 8.6 mmol), I$_2$ (7 mg, 0.03 mmol) in THF (5 mL) was added ethyl 2-bromoacetate (524 mg, 3.1 mmol) and 1,1,1-trifluoro-3-methyl-butan-2-one (0.4 g, 2.9 mmol) at 15° C. The mixture was stirred at 60° C. for 6 hours. H$_2$SO$_4$ (10% aq, 4 mL) was added, and the mixture was extracted with ethyl acetate (10 mL×4). The combined organic phases were washed with brine (30 mL), dried over Na$_2$SO$_4$, filtered and concentrated to give ethyl 3-hydroxy-4-methyl-3-(trifluoromethyl)pentanoate (1 g, crude)

Step 2: Preparation of 3-hydroxy-4-methyl-3-(trifluoromethyl) pentanoic acid

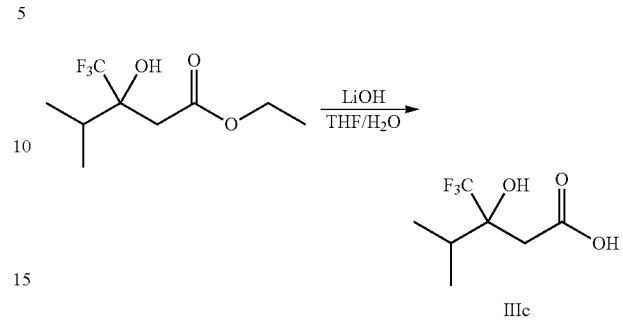

IIIc

A mixture of ethyl 3-hydroxy-4-methyl-3-(trifluoromethyl)pentanoate (1.5 g, crude) and LiOH·H$_2$O (552 mg, 13.2 mmol) in THF (20 mL) and H$_2$O (10 mL) was stirred at 15° C. for 16 hours. The pH was adjusted to ~3 with 2M HCl, and the mixture extracted with ethyl acetate (5 mL×4). The combined organic extract was washed with brine (15 mL), dried over Na$_2$SO$_4$, filtered and concentrated to give 3-hydroxy-4-methyl-3-(trifluoromethyl)pentanoic acid (1.1 g, crude) as a yellow solid, which was used directly in the next step without further purification.

IIId: 4,4,5,5-Tetrafluoro-3-hydroxy-3-methylpentanoic acid

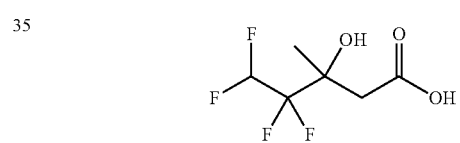

Step 1: Preparation of ethyl 4,4,5,5-tetrafluoro-3-hydroxy-3-methylpentanoate

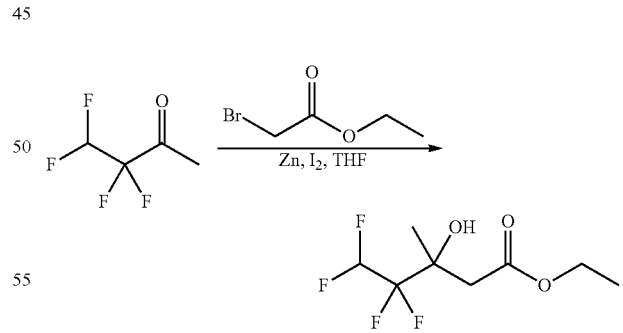

To a solution 3,3,4,4-tetrafluorobutan-2-one (2.00 g, 13.88 mmol), Zn (1.0 g, 15.7 mmol) and I$_2$ (35.2 mg, 0.14 mmol) in THF (20 mL), ethyl 2-bromoacetate (2.4 g, 14.3 mmol) was added dropwise under N$_2$ at 20° C. The mixture was stirred at 60° C. for 6 hours. The reaction mixture was cooled to 0° C., and H$_2$SO$_4$ (15 ml, 10% aq.) was carefully added. The mixture was extracted with ethyl acetate (80 mL×3), and the combined organic extract was washed with sat. aq NaHCO$_3$ (30 mL), dried over Na$_2$SO$_4$ and concentrated. The title compound (2.5 g, crude) was obtained and used in the next step without further purification.

Step 2: Preparation of 4,4,5,5-tetrafluoro-3-hydroxy-3-methylpentanoic acid

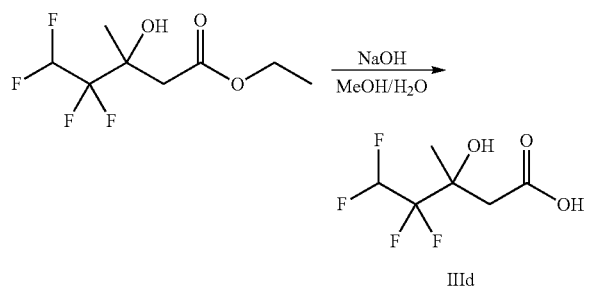

To a solution of ethyl 4,4,5,5-tetrafluoro-3-hydroxy-3-methyl-pentanoate (2.5 g, 10.8 mmol) in MeOH (80 mL) and H$_2$O (25 mL), NaOH (1.1 g, 26.9 mmol) was added at 0° C. The mixture was stirred at 20° C. for 8 hours and concentrated. The aqueous layer was acidified with 1N HCl aq. to pH=1-2, and extracted with methyl-tert-butyl ether (30 mL×5). The combined organic extract was dried over Na$_2$SO$_4$, and concentrated. The title compound was obtained (2.10 g, crude) and used without further purification.

IIIe: 5,5,5-Trifluoro-3-hydroxy-3-methylpentanoic acid

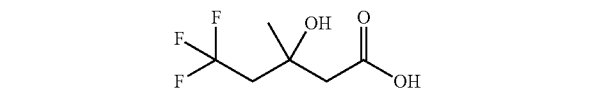

Step 1: Preparation of ethyl 5,5,5-trifluoro-3-hydroxy-3-methylpentanoate

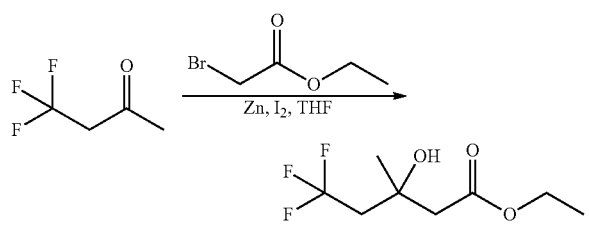

To a mixture of Zn (6.9 g, 104.7 mmol) and I$_2$ (89 mg, 0.35 mmol) in THF (80 mL) was added 4,4,4-trifluorobutan-2-one (4.4 g, 34.9 mmol) and ethyl 2-bromoacetate (6.4 g, 38.4 mmol) at 15° C. The mixture was stirred at 60° C. for 6 hours. The reaction mixture was cooled to 0° C. and quenched with H$_2$SO$_4$ (100 mL, 10% aq). The mixture was extracted with ethyl acetate (15 mL×3). The combined organic extract was washed with brine (15 mL) and dried over Na$_2$SO$_4$, filtered and concentrated. The product was obtained (11.00 g, crude) and was used directly without further purification.

Step 2: Preparation of 5,5,5-trifluoro-3-hydroxy-3-methylpentanoic acid

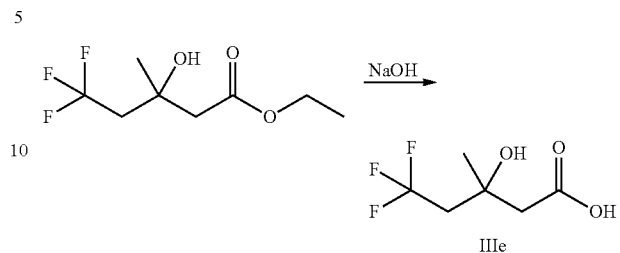

A mixture of ethyl 5,5,5-trifluoro-3-hydroxy-3-methyl-pentanoate (11 g, crude) and NaOH (4.1 g, 102.7 mmol) in H$_2$O (150 mL) was stirred at 15° C. for 16 hours. The pH was adjusted to ~2 with sat. KHSO$_4$ at 0° C., and the mixture extracted with ethyl acetate (200 mL×3). The combined organic extract was washed with brine (300 mL), dried over Na$_2$SO$_4$, filtered and concentrated to afford the product (10 g, crude)

IIIf: 3-(1-Fluorocyclopropyl)-3-hydroxybutanoic acid

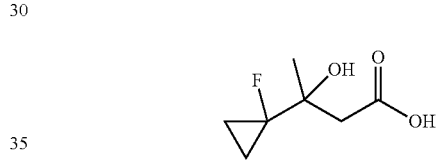

Step 1: Preparation of ethyl 3-(1-fluorocyclopropyl)-3-hydroxy butanoate

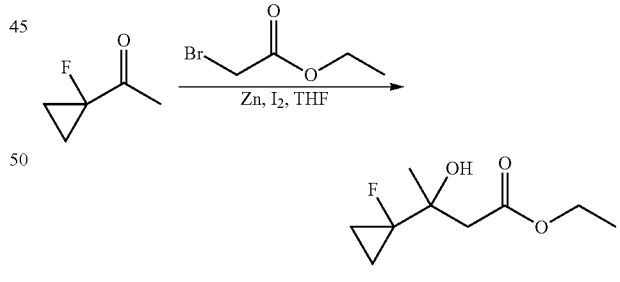

To a mixture of 1-(1-fluorocyclopropyl)ethanone (0.8 g, 7.8 mmol), Zn (1.5 g, 23.5 mmol) and I$_2$ (20 mg, 0.8 mmol) in THF (15 mL) was added ethyl 2-bromoacetate (1.4 g, 8.6 mmol) dropwise at 15° C. The mixture was stirred at 65° C. for 6 hours. The reaction mixture was cooled to 0° C., and H$_2$SO$_4$ (10% aq, 10 mL) was added dropwise. The mixture was added water (30 mL) and was extracted with ethyl acetate (20 mL×3). The combined organic extract was washed with brine (30 mL), dried over Na$_2$SO$_4$, filtered and concentrated. The obtained product was used without further purification. Yield: 1.6 g, crude.

Step 2: Preparation of 3-(1-fluorocyclopropyl)-3-hydroxy butanoic acid

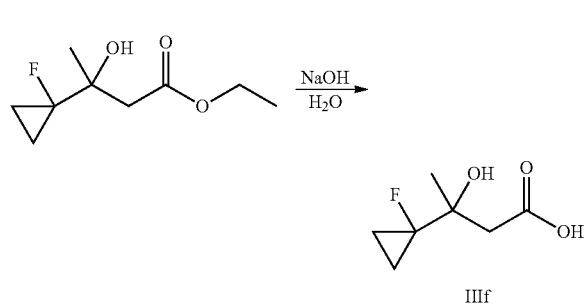

IIIf

A mixture of ethyl 3-(1-fluorocyclopropyl)-3-hydroxybutanoate (1.6 g, crude) and NaOH (670 mg, 16.8 mmol) in H$_2$O (30 mL) was stirred at 15° C. for 16 hours. The pH was adjusted with 10% HCl (aq) to ~2. The mixture was extracted with ethyl acetate (20 mL×4), and the combined organic extract was washed with brine (40 mL), dried over Na$_2$SO$_4$, filtered and concentrated to yield the crude product, which was used directly without further purification. (1.50 g, crude.

IIIg: 3-Cyclopropyl-3-hydroxybutanoic acid

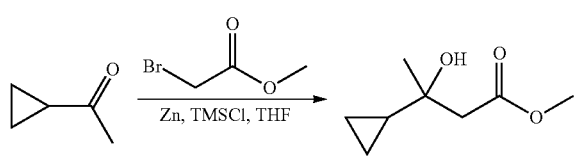

Step 1: Preparation of yl 3-cyclopropyl-3-hydroxybutanoate

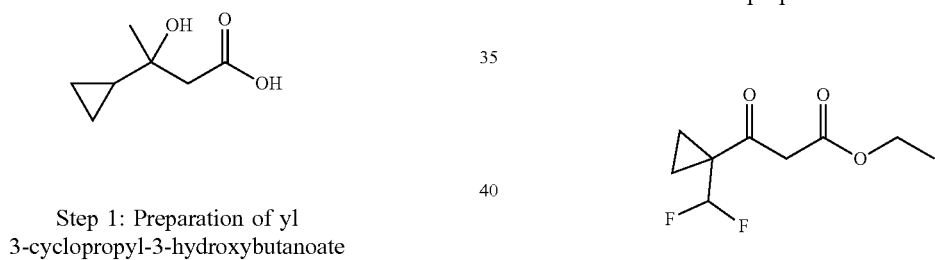

Zn (12.4 g, 190.2 mmol) in THF (150 mL) was added TMSCl (1.3 g, 11.9 mmol), and the resulting mixture was stirred at 20° C. for 15 minutes and then heated to 70° C. The heating was stopped, and methyl 2-bromoacetate (21.8 g, 142.7 mmol) was added in dropwise at such a rate that the ether boiled gently. The resulting mixture was stirred at 70° C. for 1 hour and 20° C. for 1 hour, and then a solution of 1-cyclopropylethanone (10 g, 118.9 mmol) in THF (50 mL) was added. The reaction was stirred at 20° C. for 16 hours. The mixture was poured onto NH$_3$—H$_2$O on ice (100 mL, 28%), and extracted with ethyl acetate (150 mL×2). The organic extract was washed with water (150 mL) and brine (150 mL), dried over Na$_2$SO$_4$ and concentrated to give the desired product (8.9 g, crude).

Step 2: Preparation of 3-cyclopropyl-3-hydroxybutanoic acid

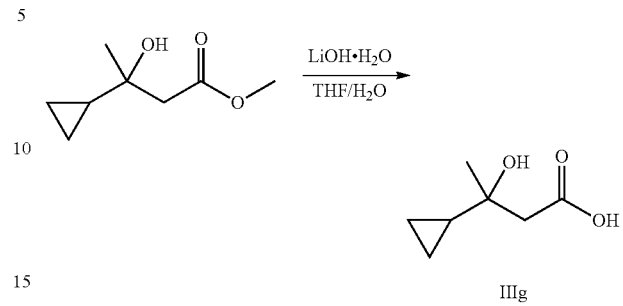

IIIg

A mixture of crude methyl 3-cyclopropyl-3-hydroxybutanoate (8.9 g, 56.3 mmol) and LiOH—H$_2$O (11.8 g, 281.3 mmol) in THF (100 mL) and H$_2$O (50 mL) was stirred at 20° C. for 16 hours. H$_2$O (50 ml) was added and extracted with ethyl acetate (100 mL×2). The organic extracts were discarded. The pH of the aqueous layer was adjusted to ~5 with 2N HCl, extracted with ethyl acetate (100 mL×3) and the combined organic fractions were washed with brine (100 mL×10), dried over Na$_2$SO$_4$, filtered and concentrated to give the desired product in 30% overall yield (5.1 g)

$^1$H NMR (400 MHz, CDCl$_3$) δ 2.67-2.51 (m, 2H), 1.25 (s, 3H), 0.90-1.00 (m, 1H), 0.33-0.50 (m, 4H).

IVa: Ethyl 3-[1-(difluoromethyl)cyclopropyl]-3-oxo-propanoate

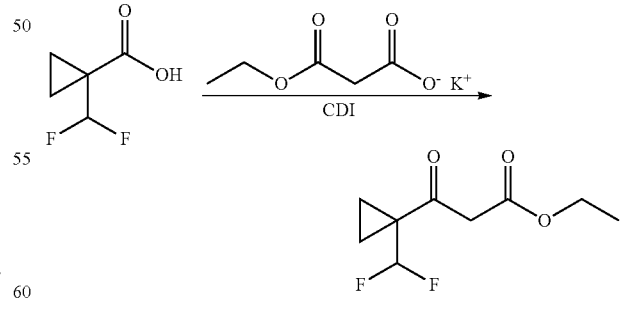

Step 1: Preparation of ethyl 3-[1-(difluoromethyl)cyclopropyl]-3-oxo-propanoate Et$_3$N (2.34 g, 23.5 mmol) and MgCl$_2$ (1.8 g, 18.4 mmol) was added to a suspension of (3-ethoxy-3-oxo-propanoyl) oxy potassium salt (2.6 g, 15.4 mmol) in MeCN (30 mL) and stirred at 20° C. for 2 hours. A pre-stirred mixture of CDI (carbonyl-diimidazole) (1.4 g, 8.8 mmol) and 1-(difluoromethyl) cyclopropane carboxylic acid (1 g, 7.4 mmol) in MeCN (20 mL) was added at 0° C. and stirred at 20° C. for 14 hours. The reaction mixture was diluted with H₂O (30 mL) and extracted with ethyl acetate (80 mL×2). The combined organic extracts were washed with brine (30 mL), dried over Na₂SO₄, filtered and concentrated. The residue was purified by flash chromatography on silica gel (Eluent of 0~10% Ethyl acetate/petroleum ether gradient). The product was obtained in 0.98 g (65%) yield.

IVb: Ethyl 3-oxo-3-[1-(trifluoromethyl) cyclopropyl]propanoate

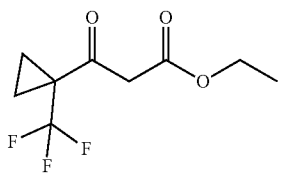

Step 1: Preparation of ethyl 3-oxo-3-[1-(trifluoromethyl) cyclopropyl]propanoate

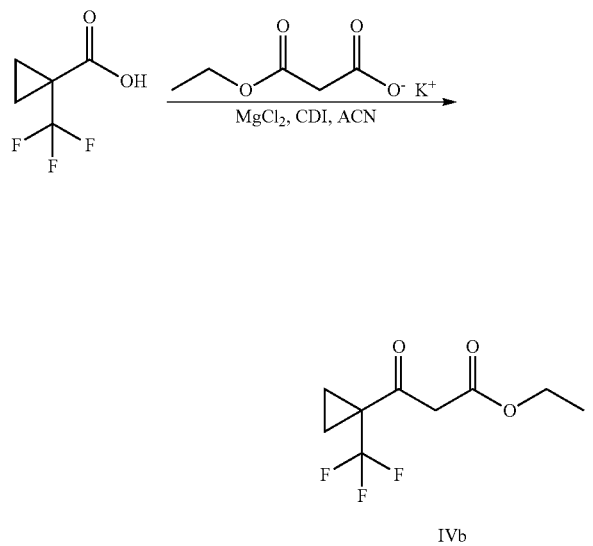

IVb

Et₃N (6.3 g, 62.3 mmol) and MgCl₂ (4.6 g, 48.7 mmol) was added to a suspension of potassium 3-ethoxy-3-oxo-propanoate (6.9 g, 40.5 mmol) in CH₃CN (25 mL) and stirred at 20° C. for 2 hours. A pre-stirred mixture of carbonyl diimidazole (CDI) (3.8 g, 23.3 mmol) and 1-(trifluoromethyl)cyclopropane carboxylic acid (3 g, 19.5 mmol) in CH₃CN (25 mL) was added at 0° C. and stirred at 20° C. for 14 hours. The mixture was poured into water (20 mL). The aqueous phase was extracted with ethyl acetate (30 mL×3). The combined organic phase was washed with brine (40 mL×2), dried with anhydrous Na₂SO₄, filtered and concentrated. The residue was purified by column chromatography on silica gel (petroleum ether/Ethyl acetate=30:1-10:1) to afford the product in 3.5 g (80%) yield.

Va: 4,4-dimethyl-3-oxo-N-[(1S)-1-[3-(trifluoromethoxy)phenyl]ethyl]pentane amide

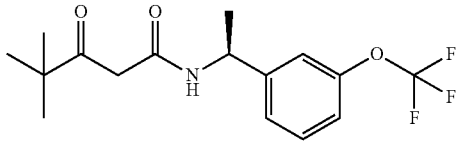 [SMILES: C[C@H](NC(=O)CC(=O)C(C)(C)C)c1cccc(OC(F)(F)F)c1]

A solution of (1S)-1-[3-(trifluoromethoxy)phenyl]ethan amine hydrochloride (IIa) (5 g, 20.69 mmol), 4,4-dimethyl-3-oxo-pentanoic acid (3.28 g, 22.76 mmol), HATU (9.44 g, 24.83 mmol) and DIPEA (8 g, 62.1 mmol) in DCM (250 mL) was stirred at 25° C. for 16 hours. The resulting mixture was washed with water (500 mL) and extracted with DCM (500 mL×2). The organic layer was washed with brine (350 mL×2), dried over Na₂SO₄ and concentrated. The residue was purified by chromatography (SiO₂, petroleum ether/ Ethyl acetate=1:0 to 3:1) to afford 4,4-dimethyl-3-oxo-N-[(1S)-1-[3-(trifluoromethoxy)phenyl]ethyl]pentanamide (11.2 g, crude).

The following intermediates were prepared by similar methodology as Va, using the relevant intermediates Vb: 4,4-Dimethyl-3-oxo-N-[(1S)-1-[3-(2,2,2-trifluoroethoxy)phenyl]ethyl]pentanamide

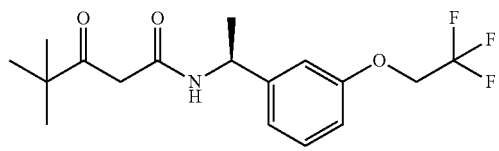 [SMILES: C[C@H](NC(=O)CC(=O)C(C)(C)C)c1cccc(OCC(F)(F)F)c1]

Prepared from IIb (2.6 g, 10.1 mmol) and 4,4-dimethyl-3-oxo-pentanoic acid (1.6 g, 11.1 mmol).

Yield: 2.6 g (75%).

Vc: (S)—N-(1-(3-(Difluoromethoxy)phenyl)ethyl)-4,4-dimethyl-3-oxopentan amide

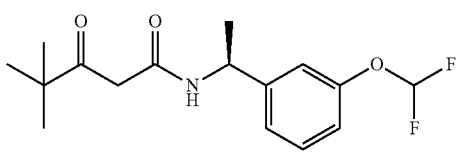 [SMILES: C[C@H](NC(=O)CC(=O)C(C)(C)C)c1cccc(OC(F)F)c1]

Prepared from IIc (0.8 g, 4.3 mmol) and 4,4-dimethyl-3-oxo-pentanoic acid (616 mg, 4.3 mmol)

Yield: 1.3 g crude

Vd: (S)-4,4-Dimethyl-3-oxo-N-(1-(3-(trifluoromethyl)phenyl)ethyl) pentanamide

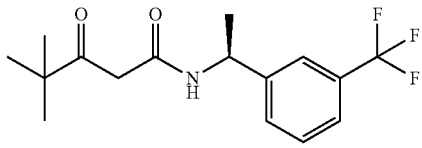 [SMILES: C[C@H](NC(=O)CC(=O)C(C)(C)C)c1cccc(C(F)(F)F)c1]

Prepared from IId (850 mg, 3.77 mmol) and 4,4-dimethyl-3-oxo-pentanoic acid (597 mg, 4.14 mmol).

Yield: 1.12 g (94%)

Ve: (S)-4,4-Dimethyl-3-oxo-N-(1-(3-(trifluoromethoxy)phenyl) propyl)pentanamide

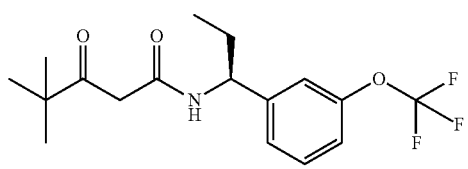

Prepared from IIe (1.04 g, 4.07 mmol) and 4,4-dimethyl-3-oxo-pentanoic acid (645 mg, 4.47 mmol).

Yield: 1.28 g (91%).

Vf: (S)-4-methyl-3-oxo-N-(1-(3-(2,2,2-trifluoroethoxy)phenyl)ethyl) pentanamide

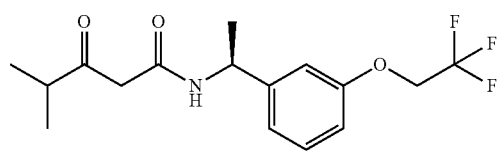 [SMILES: CC(C)C(=O)CC(=O)N[C@@H](C)c1cccc(OCC(F)(F)F)c1]

Prepared from IIb (2.89 g, 11.32 mmol) and 4-methyl-3-oxo-pentanoic acid (1.62 g).

Yield: 2.6 g (69%).

Vi: (S)-4-Methyl-3-oxo-N-(1-(3-(trifluoromethoxy)phenyl)ethyl) pentanamide

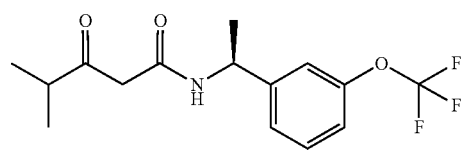 [SMILES: CC(C)C(=O)CC(=O)N[C@@H](C)c1cccc(OC(F)(F)F)c1]

Prepared from IIa (2.7 g, 13.16 mmol) and 4-methyl-3-oxo-pentanoic acid (1.60 g)

Yield: 2.00 g (47%).

Vj: N-[(1R)-2-(Difluoromethoxy)-1-[3-(trifluoromethoxy)phenyl]ethyl]-4,4-dimethyl-3-oxo-pentanamide

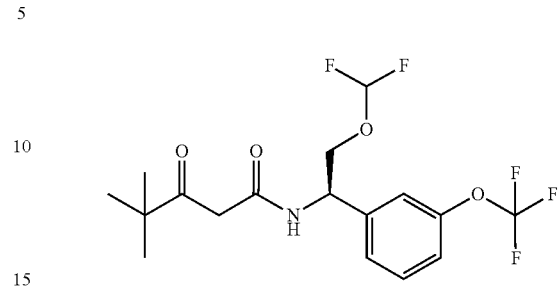

Prepared from IIg (600 mg, 2.21 mmol) and 4,4-dimethyl-3-oxo-pentanoic acid (382 mg, 2.66 mmol)

Yield: 520 mg (51%).

Vk: N-[(1R)-2-Methoxy-1-[3-(trifluoromethoxy)phenyl]ethyl]-4,4-dimethyl-3-oxo-pentanamide

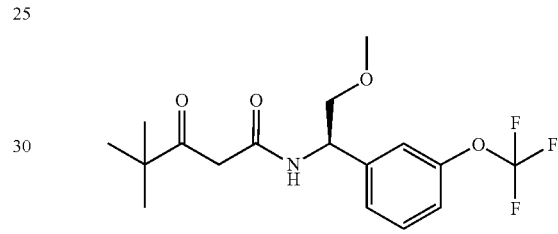

Prepared from IIf (40 mg, 0.15 mmol) and 4,4-dimethyl-3-oxo-pentanoic acid (25 mg, 0.17 mmol)

Yield: 100 mg, (94%).

Vg: 3-[1-(Difluoromethyl)cyclopropyl]-3-oxo-N-[(1S)-1-[3-(trifluoromethoxy)phenyl]ethyl] propanamide

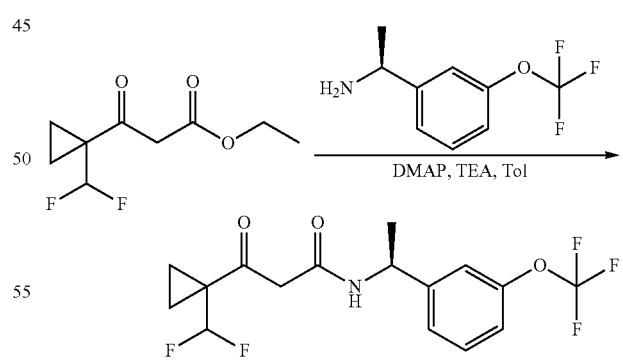

A mixture of IIa (557 mg, 2.30 mmol), IVa (0.95 g, 4.61 mmol), DMAP (57 mg, 0.46 mmol) and Et₃N (2.33 g, 23.04 mmol) in toluene (30 mL) was degassed and purged with N₂ for 3 times, then the mixture was stirred at 110° C. for 12 hours under N₂. The mixture was concentrated, and the residue was purified by flash chromatography on silica gel (Eluent of 0~35% Ethyl acetate/petroleum ether gradient) to yield the desired product (0.61 g, 72% yield).

The following were prepared by similar methodology as described for Vg, using the relevant intermediates Vh: 3-Oxo-N-[(1S)-1-[3-(trifluoromethoxy)phenyl] ethyl]-3-[1-(trifluoromethyl) cyclopropyl] propanamide

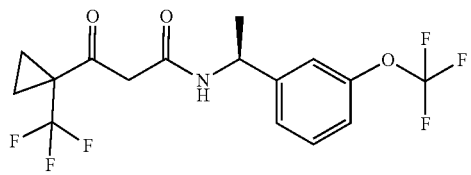 [SMILES: C[C@H](NC(=O)CC(=O)C1(C(F)(F)F)CC1)c1cccc(OC(F)(F)F)c1]

Prepared from IVb (2 g, 8.9 mmol) and IIa (915.3 mg, 4.5 mmol) Yield: 1.7 g (97%).

Vl: (S)-3-(3,3-Difluorocyclobutyl)-3-oxo-N-(1-(3-(trifluoromethoxy)phenyl)ethyl)propan amide

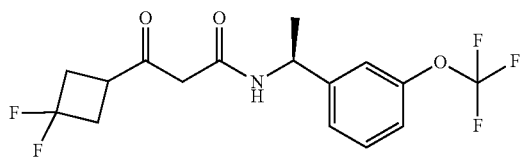 [SMILES: C[C@H](NC(=O)CC(=O)C1CC(F)(F)C1)c1cccc(OC(F)(F)F)c1]

Prepared from methyl 3-(3,3-difluorocyclobutyl)-3-oxo-propanoate (600 mg, 3.12 mmol) and IIa (377 mg, 1.56 mmol).

Yield: 470 mg, (82%).

$^1$H NMR (CDCl$_3$, 400 MHz) δ 7.39-7.35 (m, 1H), 7.26-7.23 (m, 1H), 7.15-7.11 (m, 2H), 5.16-5.08 (m, 1H), 3.44 (d, J=2.4 Hz, 2H), 2.86-2.71 (m, 5H), 1.51 (d, J=7.2 Hz, 3H).

EXAMPLES

Example 1a (S)-3-Hydroxy-4,4-dimethyl-N—((S)-1-(3-(trifluoromethoxy)phenyl)ethyl)pentanamide

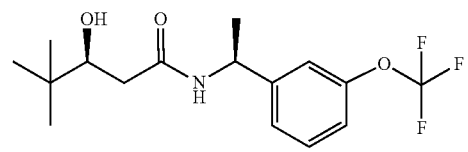 [SMILES: C[C@H](NC(=O)C[C@H](O)C(C)(C)C)c1cccc(OC(F)(F)F)c1]

and Example 1b (R)-3-Hydroxy-4,4-dimethyl-N-[(1S)-1-[3-(trifluoromethoxy)phenyl]ethyl]pentanamide

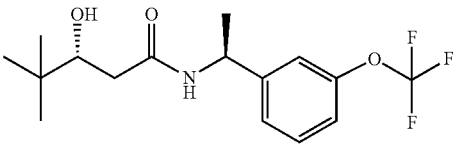 [SMILES: C[C@H](NC(=O)C[C@@H](O)C(C)(C)C)c1cccc(OC(F)(F)F)c1]

Step 1: Preparation of 3-hydroxy-4,4-dimethyl-N-[(1S)-1-[3-(trifluoromethoxy)phenyl]ethyl]pentanamide

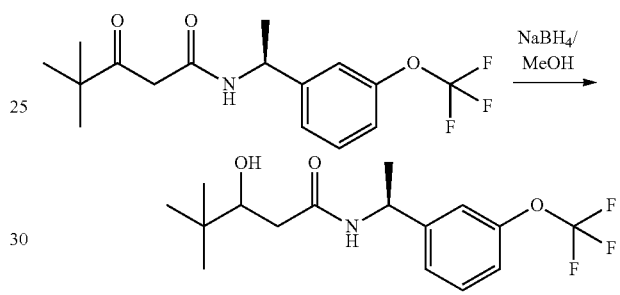

To a mixture of 4,4-dimethyl-3-oxo-N-[(1S)-1-[3-(trifluoro methoxy)phenyl]ethyl]pentanamide (Va) (5.6 g, 16.90 mmol) in MeOH (50 mL) was added NaBH$_4$ (1.28 g, 33.8 mmol) in portions at 0° C. The mixture was stirred at 0° C. for 1 hour. Water (50 mL) was added portionwise at 0° C. This reaction was repeated on the same scale twice, and the crude products from the three separate reactions were combined and worked up as follows: The mixture was concentrated to remove MeOH, and then extracted with ethyl acetate (100 mL×4). The combined organic extracts were washed with brine (50 mL×3), dried over Na$_2$SO$_4$, filtered and concentrated to afford 3-hydroxy-4,4-dimethyl-N-[(1S)-1-[3-(trifluoromethoxy)phenyl]ethyl] pentanamide (16.5 g, crude).

Step 2: Separation of (S)-3-hydroxy-4,4-dimethyl-N-[(1S)-1-[3-(trifluoromethoxy)phenyl]ethyl] pentanamide and (R)-3-hydroxy-4,4-dimethyl-N-[(1S)-1-[3-(trifluoromethoxy)phenyl]ethyl]pentanamide

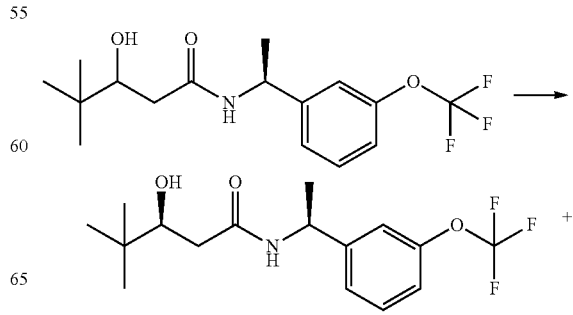

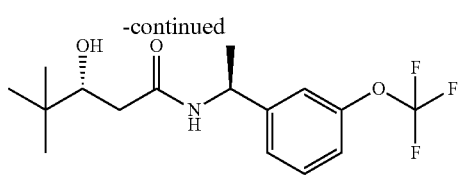

3-Hydroxy-4,4-dimethyl-N-[(1S)-1-[3-(trifluoromethoxy)phenyl]ethyl]pentanamide (27 g, 83 mmol) was separated by chromatography.

Example 1a

Yield: 10.5 g
$^1$H NMR (CDCl$_3$ 400 MHz): δ 7.33 (t, J=8.0 Hz, 1H), 7.22 (d, J=8.0 Hz, 1H), 7.05-7.20 (2H), 6.40 (br, 1H), 5.15 (m, 1H), 3.64 (dd, J=2.0 Hz, 8.4 Hz, 1H), 3.05 (br, 1H), 2.15-2.40 (m, 2H), 1.45 (d, J=7.2 Hz, 3H), 0.88 (s, 9H).
LC-MS: $t_R$=2.548 min (LCMS Method 1), m/z=334.0 [M+H]$^+$.
SFC: $t_R$=1.89 min (SFC Method 4), de=95%, $[α]_D^{20}$=−71.7 (c=0.72 g/100 mL, MeOH).

Example 1b

Yield: 10.5 g
$^1$H NMR (CDCl$_3$ 400 MHz): δ 7.32 (t, J=8.0 Hz, 1H), 7.22 (d, J=7.6 Hz, 1H), 7.13 (s, 1H), 7.10-7.07 (m, 1H), 6.52 (d, J=7.6 Hz, 1H), 5.13-5.06 (m, 1H), 3.62 (dd, J=2.0 Hz, 8.4 Hz, 1H), 3.45-3.33 (m, 1H), 2.38-2.33 (m, 1H), 2.23-2.17 (m, 1H), 1.44 (d, J=7.2 Hz, 3H), 0.88 (s, 9H). LC-MS: $t_R$=2.553 min (LCMS Method 1), m/z=334.0 [M+H]$^+$.
SFC: $t_R$=1.87 min (SFC Method 5), de=100%, $[α]_D^{20}$=42.3 (c=0.61 g/100 mL, MeOH).

The following examples were prepared by similar methodology as described for 1a and 1b, using the relevant intermediates:

Example 2a

3-Hydroxy-4,4-dimethyl-N—((S)-1-(3-(2,2,2-trifluoroethoxy)phenyl)ethyl)pentanamide

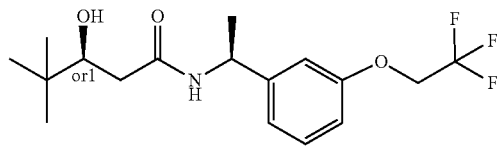 [SMILES: C[C@H](NC(=O)C[C@H](O)C(C)(C)C)c1cccc(OCC(F)(F)F)c1]

and Example 2b

3-Hydroxy-4,4-dimethyl-N—((S)-1-(3-(2,2,2-trifluoroethoxy)phenyl)ethyl)pentanamide

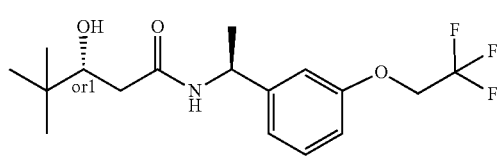 [SMILES: C[C@H](NC(=O)C[C@@H](O)C(C)(C)C)c1cccc(OCC(F)(F)F)c1]

Step 1: Preparation of 3-hydroxy-4,4-dimethyl-N—((S)-1-(3-(2,2,2-trifluoroethoxy)phenyl)ethyl)pentanamide

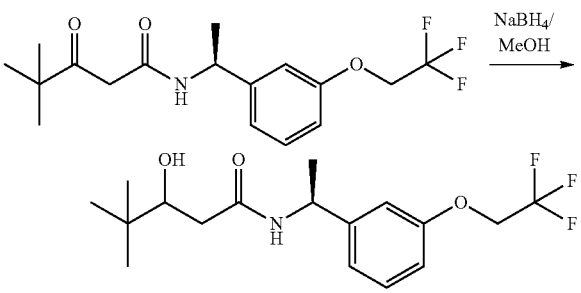

3-Hydroxy-4,4-dimethyl-N—((S)-1-(3-(2,2,2-trifluoroethoxy)phenyl)ethyl)pentanamide was prepared from Vb, in 84% yield.

Step 2: Separation of (S)-3-hydroxy-4,4-dimethyl-N—((S)-1-(3-(2,2,2-trifluoroethoxy)phenyl)ethyl)pentanamide and (R)-3-hydroxy-4,4-dimethyl-N—((S)-1-(3-(2,2,2-trifluoroethoxy)phenyl)ethyl)pentanamide

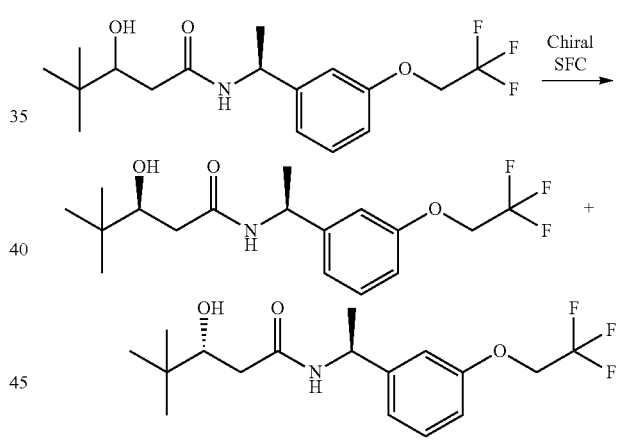

3-Hydroxy-4,4-dimethyl-N-[(1S)-1-[3-(2,2,2-trifluoroethoxy) phenyl]ethyl]pentanamide (0.84 g, 2.52 mmol) was separated by chiral SFC.

Example 2a

Yield: 0.25 g
$^1$H NMR (CDCl$_3$, 400 MHz) δ 7.30 (t, J=7.6 Hz, 1H), 7.01 (d, J=7.6 Hz, 1H), 6.93 (s, 1H), 6.85 (dd, J=8.4 Hz, 2.8 Hz, 1H), 6.08 (br d, J=5.2 Hz, 1H), 5.13 (m, 1H), 4.36 (q, J=16.0 Hz, 8.0 Hz, 2H), 3.68 (dd, J=10.4 Hz, 3.0 Hz, 1H), 3.24 (d, J=3.2 Hz, 1H), 2.39-2.23 (m, 2H), 1.49 (d, J=6.8 Hz, 3H), 0.93 (s, 9H)
LC-MS: $t_R$=2.68 min (LCMS Method 2), m/z=348.0 [M+H]$^+$.
SFC: $t_R$=1.78 min (SFC Method 1), de=98.3%, $[α]_D^{20}$=−68.0 (c=0.25, MeOH).

Example 2b

Yield: 0.37 g

¹H NMR (CDCl₃, 400 MHz) δ7.29 (t, J=8.0 Hz, 1H), 7.01 (d, J=8.0 Hz, 1H), 6.94 (s, 1H), 6.84 (dd, J=8.0, 2.4 Hz, 1H), 6.04 (m, 1H), 5.13 (m, 1H), 4.36 (q, J=16.0 Hz, 8.0 Hz, 2H), 3.70-3.67 (m, 1H), 3.15 (d, J=2.8 Hz, 1H), 2.40-1.96 (m, 2H), 1.50 (d, J=7.2 Hz, 3H), 0.93 (s, 9H) LC-MS: $t_R$=2.543 min (LCMS Method 2), m/z=348.0 [M+H]⁺.

SFC: $t_R$=1.87 min (SFC Method 1), de=92.0%, $[\alpha]_D^{20}$=−53.3 (c=0.21, MeOH).

Example 3a: N—((S)-1-(3-(Difluoromethoxy)phenyl)ethyl)-3-hydroxy-4,4-dimethylpentanamide

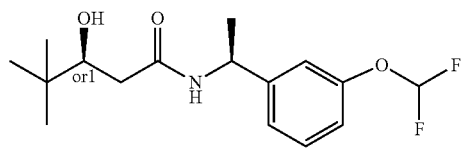 [SMILES: C[C@H](NC(=O)C[C@H](O)C(C)(C)C)c1cccc(OC(F)F)c1]

and

Example 3b: N—((S)-1-(3-(Difluoromethoxy)phenyl)ethyl)-3-hydroxy-4,4-dimethylpentanamide

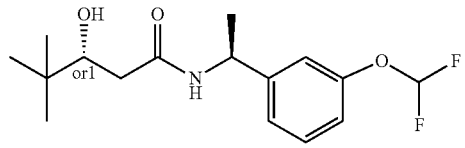 [SMILES: C[C@H](NC(=O)C[C@@H](O)C(C)(C)C)c1cccc(OC(F)F)c1]

Step1: Preparation of N—((S)-1-(3-(difluoromethoxy)phenyl)ethyl)-3-hydroxy-4,4-dimethylpentanamide

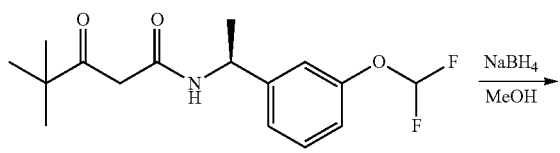

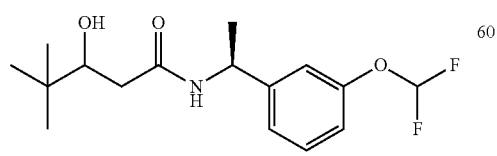

Prepared from Vc, 84% yield.

Step 2: Separation of (S)—N—((S)-1-(3-(difluoromethoxy)phenyl)ethyl)-3-hydroxy-4,4-dimethylpentanamide and (R)—N—((S)-1-(3-(difluoromethoxy)phenyl)ethyl)-3-hydroxy-4,4-dimethylpentan-amide

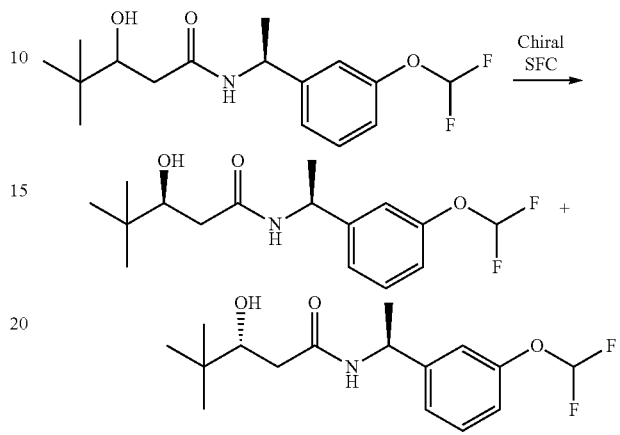

N—((S)-1-(3-(Difluoromethoxy)phenyl)ethyl)-3-hydroxy-4,4-dimethylpentanamide (450 mg) was separated by chiral SFC.

Example 3a

Yield: 168 mg

¹H NMR (CDCl₃ 400 MHz): δ 7.31-7.29 (m, 1H), 7.26-7.24 (m, 1H), 7.16-7.14 (m, 1H), 7.10-6.98 (m, 1H), 6.49 (t, J=76 Hz, 1H), 6.14 (brs, 1H), 5.14-5.07 (m, 1H), 3.66 (d, J=10.4 Hz, 1H), 3.17 (s, 1H), 2.38-2.34 (m, 1H), 2.28-2.18 (m, 1H), 1.47-1.40 (m, 3H), 0.98 (s, 9H).

LC-MS: $t_R$=2.161 min (LCMS Method 3), m/z=316.1 [M+H]⁺.

SFC: $t_R$=2.15 min (SFC Method 2), de=96.6%, $[\alpha]_D^{20}$=−16 (c=0.25, MeOH).

Example 3b

Yield: 126 mg

¹H NMR (CDCl₃ 400 MHz): δ 7.34-7.30 (m, 1H), 7.16-7.12 (m, 1H), 7.04-6.97 (m, 2H), 6.31 (t, J=76 Hz, 1H), 6.14 (brs, 1H), 5.12-5.06 (m, 1H), 3.67-3.62 (m, 1H), 3.29 (s, 1H), 2.37-2.31 (m, 1H), 2.26-2.19 (m, 1H), 1.47-1.43 (m, 3H), 0.98 (s, 9H).

LC-MS: $t_R$=2.16 min (LCMS Method 3), m/z=316.1 [M+H]⁺.

SFC: $t_R$=2.42 min (SFC Method 2), de=100%, $[\alpha]_D^{20}$=−57.6 (c=0.5, MeOH).

Example 4a: 3-Hydroxy-4,4-dimethyl-N—((S)-1-(3-(trifluoro-methyl) phenyl)ethyl) pentanamide

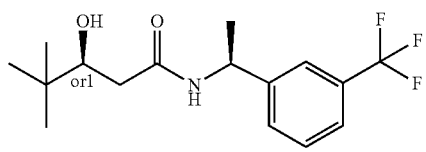 [SMILES: C[C@H](NC(=O)C[C@H](O)C(C)(C)C)c1cccc(C(F)(F)F)c1]

and

Example 4b: 3-Hydroxy-4,4-dimethyl-N—((S)-1-(3-(trifluoro-methyl) phenyl)ethyl) pentanamide

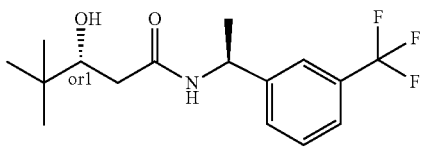 [SMILES: C[C@H](NC(=O)C[C@@H](O)C(C)(C)C)c1cccc(C(F)(F)F)c1]

Step 1: Preparation of 3-hydroxy-4,4-dimethyl-N—((S)-1-(3-(trifluoromethyl)phenyl)ethyl)pentanamide

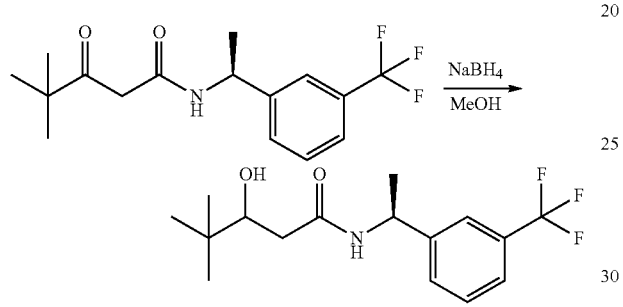

Prepared from Vd (980 mg, 87% yield).

Step 2: Separation of (S)-3-hydroxy-4,4-dimethyl-N—((S)-1-(3-(trifluoromethyl)phenyl)ethyl)pentanamide and (R)-3-hydroxy-4,4-dimethyl-N—((S)-1-(3-(trifluoromethyl)phenyl)ethyl) pentanamide

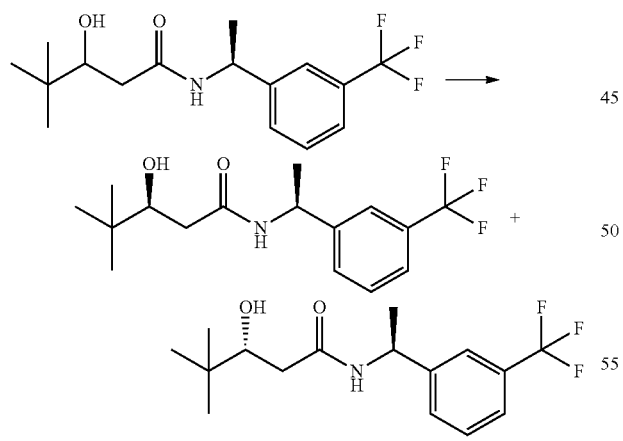

3-Hydroxy-4,4-dimethyl-N—((S)-1-(3-(trifluoromethyl) phenyl)ethyl)pentan amide was separated by chromatography on silica, (petroleum ether:Ethyl acetate=3:1).

Example 4a: Yield: 220 mg $^1$H NMR (CDCl$_3$ 400 MHz): δ 7.56 (s, 1H), 7.52-7.43 (m, 3H), 6.22-6.21 (m, 1H), 5.21-5.14 (m, 1H), 3.68-3.64 (m, 1H), 3.14 (d, J=3.2 Hz, 1H), 2.40-2.36 (m, 1H), 2.26-2.20 (m, 1H), 1.50 (d, J=7.2 Hz, 3H), 0.91 (s, 9H).

LC-MS: $t_R$=2.48 min (LCMS Method 1), m/z=318.0 [M+H]$^+$.

SFC: $t_R$=1.56 min (SFC Method 3), de=100%, $[α]_D^{20}$=−25.5 (c=0.19 g/100 mL, MeOH).

Example 4b: Yield: 270 mg $^1$H NMR (CDCl$_3$ 400 MHz): δ 7.54-7.45 (m, 4H), 6.25-6.23 (m, 1H), 5.20-5.13 (m, 1H), 3.69-3.65 (m, 1H), 3.24 (d, J=3.2 Hz, 1H), 2.39-2.35 (m, 1H), 2.27-2.21 (m, 1H), 1.49 (d, J=6.8 Hz, 3H), 0.91 (s, 9H).

LC-MS: $t_R$=2.48 min (LCMS Method 1), m/z=318.0 [M+H]$^+$.

SFC: $t_R$=1.93 min (SFC Method 3), de=100%, $[α]_D^{20}$=−61.4 (c=0.57 g/100 mL, MeOH).

Example 8a: 3-Hydroxy-4,4-dimethyl-N—((S)-1-(3-(trifluoro-methoxy) phenyl) propyl) pentanamide

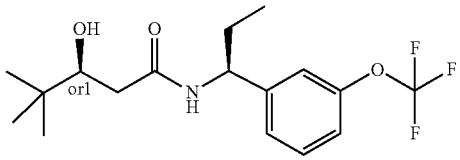 [SMILES: CC[C@H](NC(=O)C[C@H](O)C(C)(C)C)c1cccc(OC(F)(F)F)c1]

and

Example 8b: 3-Hydroxy-4,4-dimethyl-N—((S)-1-(3-(trifluoro-methoxy) phenyl) propyl) pentanamide

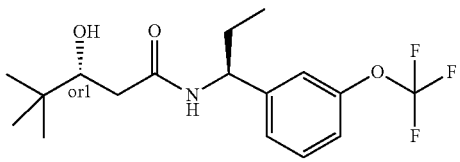 [SMILES: CC[C@H](NC(=O)C[C@@H](O)C(C)(C)C)c1cccc(OC(F)(F)F)c1]

Step 1: Preparation of 3-hydroxy-4,4-dimethyl-N—((S)-1-(3-(trifluoromethoxy)phenyl)propyl)pentanamide

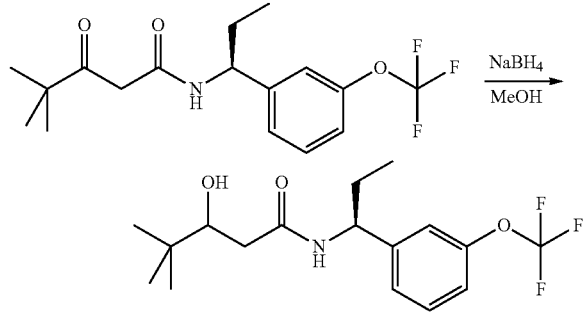

Prepared from Ve, Yield: 1.22 g

Step 2: Separation of (S)-3-hydroxy-4,4-dimethyl-N—((S)-1-(3-(trifluoromethoxy)phenyl)propyl)pentanamide and (R)-3-hydroxy-4,4-dimethyl-N—((S)-1-(3-(trifluoromethoxy)phenyl)propyl) pentanamide

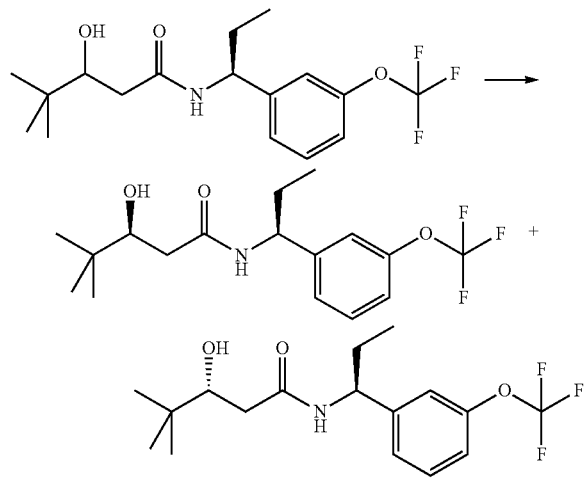

3-Hydroxy-4,4-dimethyl-N—((S)-1-(3-(trifluoromethoxy)phenyl) propyl)pentanamide was separated by flash chromatography on silica gel (Eluent of 0~30% Ethyl acetate/petroleum ether gradient).

Example 8a: Yield: 0.51 g $^1$H NMR (CDCl$_3$ 400 MHz): δ 7.40-7.34 (m, 1H), 7.25-7.21 (m, 1H), 7.14-7.10 (m, 2H), 6.22-6.15 (m, 1H), 4.92 (q, J=7.6 Hz, 1H), 3.71-3.65 (m, 1H), 3.21 (d, J=2.8 Hz, 1H), 2.40-2.23 (m, 2H), 1.82 (q, J=7.2 Hz, 2H), 0.94-0.90 (m, 12H).

LC-MS: $t_R$=2.486 min (LCMS Method 5), m/z=348.0 [M+H]$^+$.

SFC: $t_R$=1.775 min. (SFC Method 3), de=98.7%, $[α]_D^{20}$=−80.0 (c=0.31 g/100 mL, MeOH).

Example 8b: Yield: 0.59 g $^1$H NMR (CDCl$_3$ 400 MHz): δ 7.39-7.33 (m, 1H), 7.25-7.20 (m, 1H), 7.14-7.09 (m, 2H), 6.24 (br d, J=8.0 Hz, 1H), 4.92 (q, J=7.6 Hz, 1H), 3.69-3.63 (m, 1H), 3.15 (d, J=3.2 Hz, 1H), 2.40-2.25 (m, 2H), 1.81 (q, J=7.6 Hz, 2H), 0.94-0.90 (m, 12H).

LC-MS: $t_R$=2.506 min (LCMS Method 5), m/z=348.0 [M+H]$^+$.

SFC: $t_R$=1.609 min. (SFC Method 3) de=98.7%, $[α]_D^{20}$=−40.0 (c=0.27 g/100 mL, MeOH).

Example 11a: 3-(3,3-Difluorocyclobutyl)-3-hydroxy-N—((S)-1-(3-(trifluoromethoxy)phenyl)ethyl) propanamide

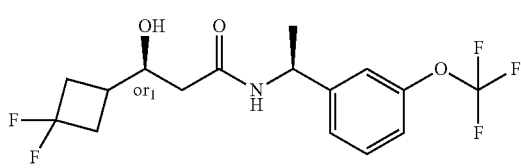 [SMILES: C[C@H](NC(=O)C[C@H](O)C1CC(F)(F)C1)c1cccc(OC(F)(F)F)c1]

and

Example 11b: 3-(3,3-Difluorocyclobutyl)-3-hydroxy-N—((S)-1-(3-(trifluoromethoxy)phenyl)ethyl) propanamide

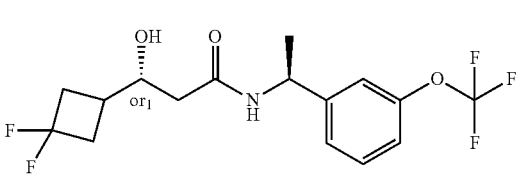 [SMILES: C[C@H](NC(=O)C[C@@H](O)C1CC(F)(F)C1)c1cccc(OC(F)(F)F)c1]

Step 1: Preparation of 3-(3,3-difluorocyclobutyl)-3-hydroxy-N—((S)-1-(3-(trifluoromethoxy)phenyl) ethyl)propanamide

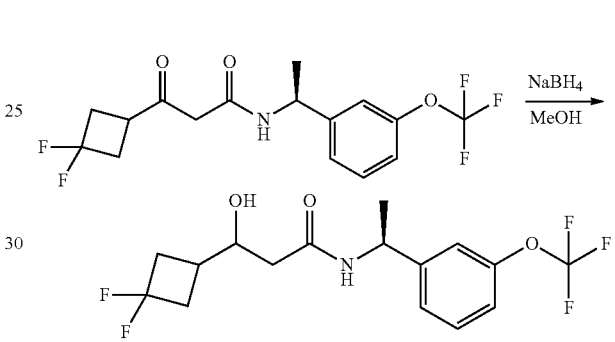

Prepared from V1. Yield: 300 mg, (60.7%).

Step 2: Separation of (S)-3-(3,3-difluorocyclobutyl)-3-hydroxy-N—((S)-1-(3-(trifluoromethoxy)phenyl)ethyl)propan-amide and (R)-3-(3,3-difluorocyclobutyl)-3-hydroxy-N—((S)-1-(3-(trifluoromethoxy)phenyl)ethyl)propanamide

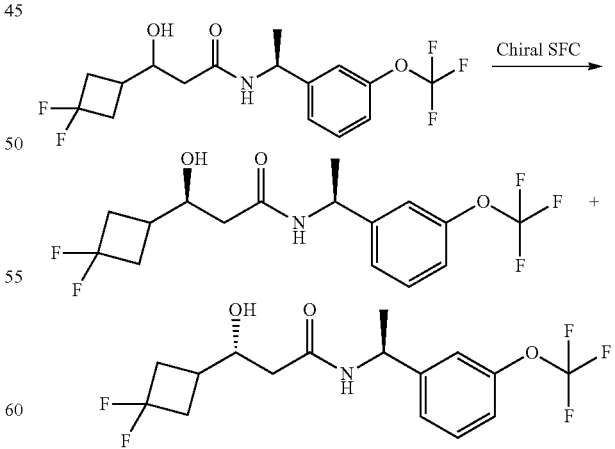

Separated by chiral SFC.

Example 11a: Yield 90 mg $^1$H NMR (400 MHz, CDCl$_3$) δ 7.42-7.35 (m, 1H), 7.25 (d, J=7.6 Hz, 1H), 7.17-7.11 (m, 2H), 5.93 (d, J=7.2 Hz, 1H), 5.19-5.09 (m, 1H), 4.01-3.93 (m, 1H), 3.86 (d, J=3.6 Hz, 1H), 2.62-2.48 (m, 3H), 2.46-2.13 (m, 4H), 1.50 (d, J=6.8 Hz, 3H).

LC-MS: $t_R$=2.513 min (LCMS Method 2), m/z=368.0 [M+H]$^+$.

SFC: $t_R$=2.169 min. (SFC method 3), de=97.4%, $[\alpha]_D^{20}$=−42.0 (c=2.0 mg/mL, MeOH).

Example 11b: Yield 90 mg $^1$H NMR (400 MHz, CDCl$_3$) δ 7.40-7.36 (m, 1H), 7.25 (d, J=7.6 Hz, 1H), 7.16-7.11 (m, 2H), 5.99 (d, J=7.2 Hz, 1H), 5.18-5.09 (m, 1H), 3.98 (t, J=7.2 Hz, 1H), 3.83 (br s, 1H), 2.61-2.49 (m, 3H), 2.45-2.12 (m, 4H), 1.50 (d, J=6.8 Hz, 3H).

LC-MS: $t_R$=2.235 min (LCMS Method 3), m/z=368.0 [M+H]$^+$.

SFC: $t_R$=2.013 min. (SFC Method 3), de=99.6%, $[\alpha]_D^{20}$=−17.0 (c=2.0 mg/mL, MeOH).

Example 12a: 3-Hydroxy-4-methyl-N—((S)-1-(3-(2,2,2-trifluoro-ethoxy) phenyl)ethyl) pentanamide

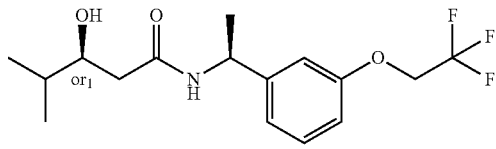 [SMILES: CC(C)[C@@H](O)CC(=O)N[C@@H](C)c1cccc(OCC(F)(F)F)c1]

and

Example 12b: 3-Hydroxy-4-methyl-N—((S)-1-(3-(2,2,2-trifluoro-ethoxy) phenyl)ethyl) pentanamide

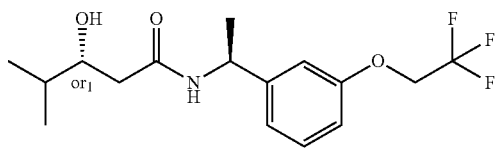 [SMILES: CC(C)[C@H](O)CC(=O)N[C@@H](C)c1cccc(OCC(F)(F)F)c1]

Step 1: Preparation of 3-Hydroxy-4-methyl-N—((S)-1-(3-(2,2,2-trifluoroethoxy)phenyl)ethyl)pentanamide

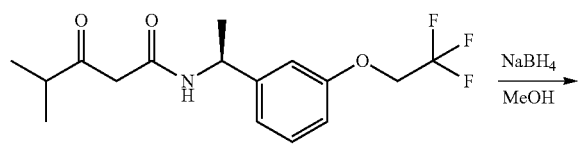

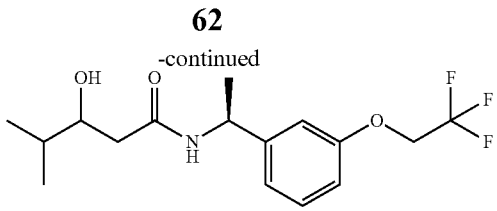

Prepared from Vf.

Yield: 0.88 g (87%)

Step 2: Separation of (S)-3-hydroxy-4-methyl-N—((S)-1-(3-(2,2,2-trifluoroethoxy)phenyl)ethyl)pentanamide and (R)-3-hydroxy-4-methyl-N—((S)-1-(3-(2,2,2-trifluoroethoxy)phenyl)ethyl)pentanamide

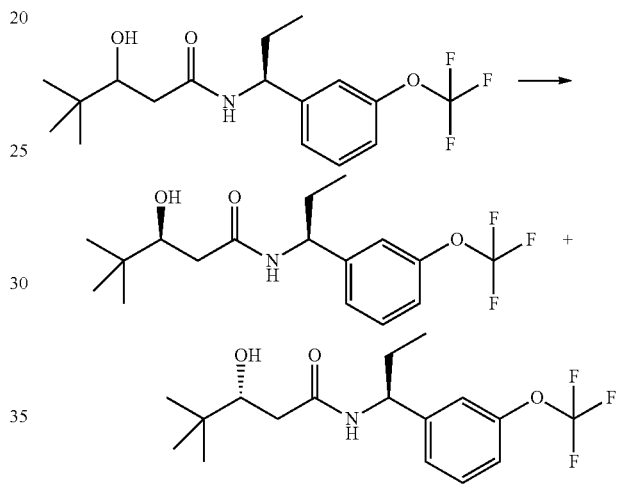

3-Hydroxy-4-methyl-N—((S)-1-(3-(2,2,2-trifluoroethoxy)phenyl) ethyl)pentanamide was separated by chiral SFC.

Example 12a: Yield: 0.362 g $^1$H NMR (CDCl$_3$, 400 MHz) δ 7.31 (t, J=8.0 Hz, 1H), 7.01 (d, J=7.2 Hz, 1H), 6.92 (t, J=2.0 Hz, 1H), 6.83 (dd, J=8.0, 2.4 Hz, 1H), 6.08 (br d, J=7.2 Hz, 1H), 5.12 (m, 1H), 4.36 (q, J=8.0 Hz, 2H), 3.80-3.74 (m, 1H), 3.36 (d, J=3.2 Hz, 1H), 2.37-2.27 (m, 2H), 1.73-1.70 (m, 1H), 1.49 (d, J=6.8 Hz, 3H), 0.94 (dd, J=10.4, 6.8 Hz, 6H);

LC-MS: $t_R$=2.531 min (LCMS Method 2), m/z=334.0 [M+H]$^+$.

SFC: $t_R$=2.864 min (SFC Method 3), de=99.2%, $[\alpha]_D^{20}$=−74.0 (c=0.20, MeOH).

Example 12b: Yield: 0.245 g $^1$H NMR (CDCl$_3$, 400 MHz) δ 7.30 (t, J=8.0 Hz, 1H), 7.00 (d, J=8.0 Hz, 1H), 6.92 (t, J=2.0 Hz, 1H), 6.83 (dd, J=8.0, 2.4 Hz, 1H), 6.14 (br d, J=6.8 Hz, 1H), 5.11 (m, 1H), 4.36 (q, J=16.4, 8.0 Hz, 2H), 3.79-3.75 (m, 1H), 3.34 (d, J=3.2 Hz, 1H), 2.38-2.25 (m, 2H), 1.73-1.62 (m, 1H), 1.49 (d, J=7.2 Hz, 3H), 0.94 (dd, J=10.0, 6.8 Hz, 6H);

LC-MS: $t_R$=2.543 min (LCMS Method 2), m/z=334.0 [M+H]$^+$.

SFC: $t_R$=3.071 min (SFC Method 3), de=99.7%, $[\alpha]_D^{20}$=−47.0 (c=0.20, MeOH).

Example 14a: 3-(1-(Difluoromethyl) cyclopropyl)-3-hydroxy-N—((S)-1-(3-(trifluoromethoxy)phenyl)ethyl)propanamide

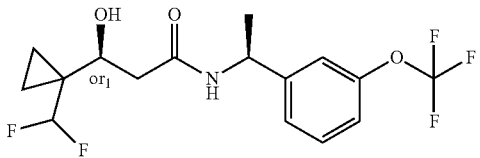 [SMILES: C[C@H](NC(=O)C[C@H](O)C1(C(F)F)CC1)c1cccc(OC(F)(F)F)c1]

and

Example 14b: 3-(1-(Difluoromethyl) cyclopropyl)-3-hydroxy-N—((S)-1-(3-(trifluoromethoxy)phenyl)ethyl)propanamide

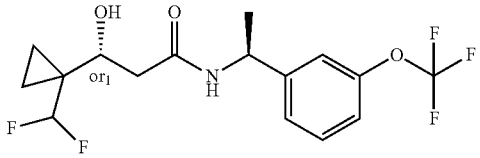 [SMILES: C[C@H](NC(=O)C[C@@H](O)C1(C(F)F)CC1)c1cccc(OC(F)(F)F)c1]

Step 1: Preparation of 3-(1-(difluoromethyl)cyclopropyl)-3-hydroxy-N—((S)-1-(3-(trifluoromethoxy)phenyl)ethyl)propanamide

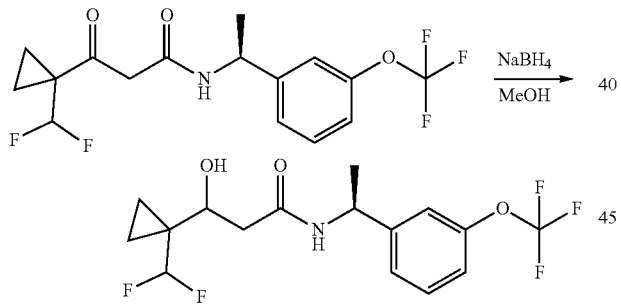

Prepared from Vg.
Yield: 0.58 g

Step 2: Separation of (S)-3-(1-(difluoromethyl)cyclopropyl)-3-hydroxy-N—((S)-1-(3-(trifluoromethoxy)phenyl)ethyl)propanamide and (R)-3-(1-(difluoromethyl)cyclopropyl)-3-hydroxy-N—((S)-1-(3-(trifluoromethoxy)phenyl)ethyl)propanamide

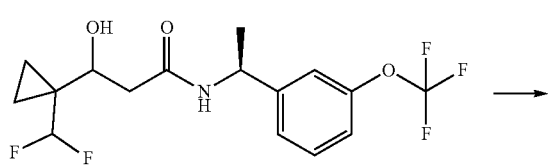

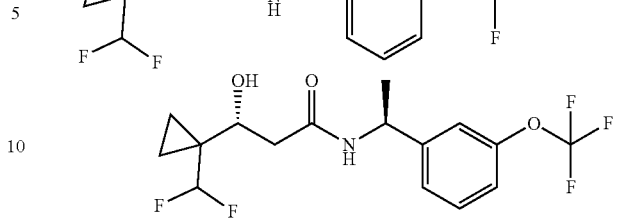

3-(1-(difluoromethyl) cyclopropyl)-3-hydroxy-N—((S)-1-(3-(trifluoromethoxy)phenyl)ethyl)propanamide was separated by flash silica gel chromatography (Eluent of 0~41% Ethyl acetate/petroleum ether gradient).

Example 14a: 0.2 g
$^1$H NMR (CDCl$_3$ 400 MHz): δ 7.40-7.34 (m, 1H), 7.26-7.22 (m, 1H), 7.16-7.11 (m, 2H), 6.11 (br d, J=7.2 Hz, 1H), 5.88 (t, J=58.4 Hz, 1H), 5.12 (quin, J=7.2 Hz, 1H), 3.91 (d, J=3.2 Hz, 1H), 3.81-3.75 (m, 1H), 2.62-2.48 (m, 2H), 1.49 (d, J=7.2 Hz, 3H), 0.87-0.76 (m, 2H), 0.76-0.62 (m, 2H).
LC-MS: $t_R$=2.448 min (LCMS Method 1), m/z=368.0 [M+H]$^+$.
SFC: $t_R$=2.282 min. (SFC Method 3), de=97.9%, $[α]_D^{20}$=−62.0 (c=0.27 g/100 mL, MeOH).

Example 14b: Yield: 0.18 g
$^1$H NMR (CDCl$_3$ 400 MHz): δ 7.40-7.34 (m, 1H), 7.24 (d, J=7.6 Hz, 1H), 7.17-7.10 (m, 2H), 6.06 (br d, J=7.6 Hz, 1H), 5.84 (t, J=58.4 Hz, 1H), 5.12 (quin, J=7.2 Hz, 1H), 3.86-3.79 (m, 2H), 2.55 (d, J=5.6 Hz, 2H), 1.50 (d, J=6.8 Hz, 3H), 0.83-0.75 (m, 2H), 0.74-0.66 (m, 2H). LC-MS: $t_R$=2.467 min (LCMS Method 1), m/z=368.0 [M+H]$^+$.
SFC $t_R$=1.960 min. (SFC Method 3), de=96.3%, $[α]_D^{20}$=−54.4 (c=0.25 g/100 mL, MeOH).

Example 16a: 3-Hydroxy-N—((S)-1-(3-(trifluoromethoxy)phenyl)ethyl)-3-(1-(trifluoro methyl)cyclopropyl)propanamide

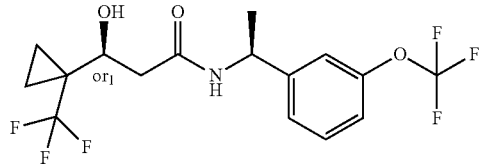 [SMILES: C[C@H](NC(=O)C[C@H](O)C1(C(F)(F)F)CC1)c1cccc(OC(F)(F)F)c1]

and

Example 16b: 3-Hydroxy-N—((S)-1-(3-(trifluoromethoxy)phenyl)ethyl)-3-(1-(trifluoro methyl)cyclopropyl)propanamide

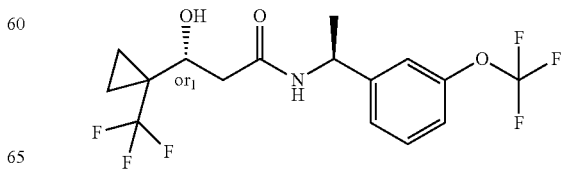

Step 1: Preparation of 3-hydroxy-N—((S)-1-(3-(trifluoro-methoxy)phenyl)ethyl)-3-(1-(trifluoromethyl)cyclopropyl) propanamide

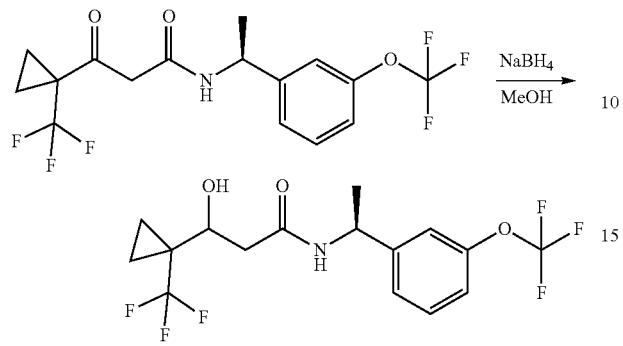

Prepared from Vh and used directly in the next step.

Step 2: Separation of (R)-3-hydroxy-N—((S)-1-(3-(trifluoro-methoxy)phenyl)ethyl)-3-(1-(trifluoromethyl)cyclopropyl) propanamide and (S)-3-hydroxy-N—((S)-1-(3-(trifluoromethoxy)phenyl)ethyl)-3-(1-(trifluoromethyl)cyclopropyl)propanamide

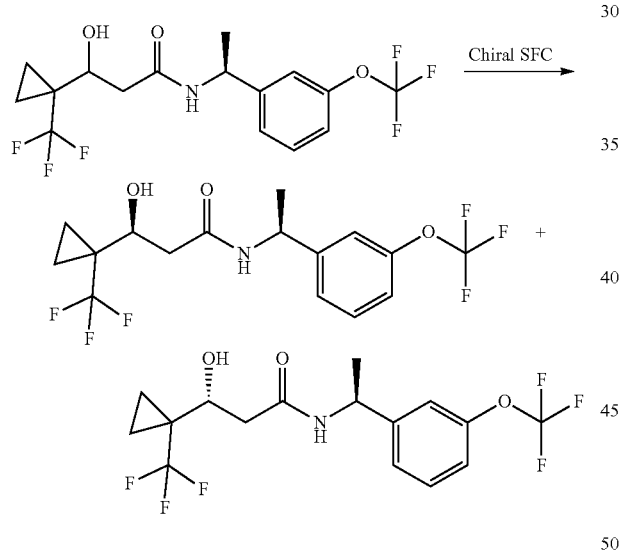

The crude product from step 1 was separated by chiral SFC to yield the desired products.

Example 16a: Yield: 556 mg $^1$H NMR (DMSO-d$^6$ 400 MHz): δ 8.37 (d, J=7.6 Hz, 1H), 7.43-7.39 (m, 1H), 7.31-7.29 (m, 1H), 7.23 (s, 1H), 7.18-7.16 (m, 1H), 5.21 (d, J=5.2 Hz, 1H), 4.96-4.88 (m, 1H), 3.85-3.75 (m, 1H), 2.35-2.25 (m, 2H), 1.30 (d, J=7.2 Hz, 3H), 0.85-0.77 (m, 4H).

LC-MS: t$_R$=2.626 min (LCMS Method 2), m/z=386.0 [M+H]$^+$.

SFC: t$_R$=2.010 min. (SFC Method 3), de=99.9%, [α]$_D^{20}$=−56.0 (c=0.01 g/100 mL, MeOH).

Example 16b: Yield: 692 mg $^1$H NMR (DMSO-d$^6$ 400 MHz): δ 8.36 (d, J=8.0 Hz, 1H), 7.42-7.38 (m, 1H), 7.32 (d, J=8.0 Hz, 1H), 7.25 (s, 1H), 7.17-7.15 (m, 1H), 5.20 (d, J=5.2 Hz, 1H), 4.95-4.91 (m, 1H), 3.75-3.85 (m, 1H), 2.25-2.35 (m, 2H), 1.30 (d, J=6.8 Hz, 3H), 0.80-0.79 (m, 4H).

LC-MS: t$_R$=2.649 min (LCMS Method 2), m/z=386.0 [M+H]$^+$.

SFC: t$_R$=1.615 min. (SFC Method 3), de=95.7%, [α]$_D^{20}$=−46.0 (c=0.01 g/100 mL, MeOH).

Example 20a: 3-Hydroxy-4-methyl-N—((S)-1-(3-(trifluoromethoxy)phenyl)ethyl) pentanamide

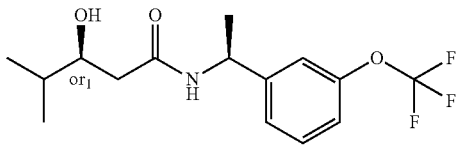 [SMILES: CC(C)[C@@H](O)CC(=O)N[C@@H](C)c1cccc(OC(F)(F)F)c1]

and

Example 20b: 3-Hydroxy-4-methyl-N—((S)-1-(3-(trifluoromethoxy)phenyl)ethyl) pentanamide

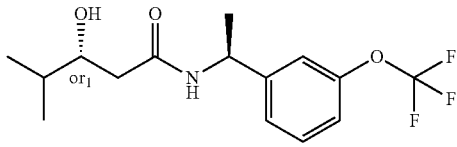 [SMILES: CC(C)[C@H](O)CC(=O)N[C@@H](C)c1cccc(OC(F)(F)F)c1]

Step 1: Preparation of 3-hydroxy-4-methyl-N—((S)-1-(3-(trifluoromethoxy)phenyl)ethyl)pentanamide

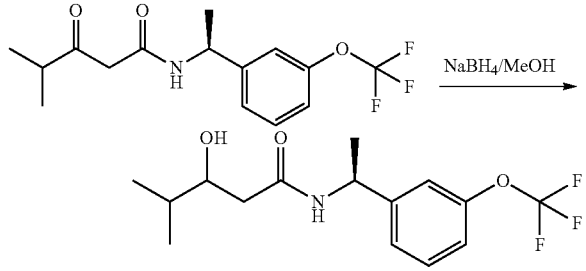

Prepared from Vi. Yield: 1.80 g (72%)

Step 2: Separation of (S)-3-hydroxy-4-methyl-N—((S)-1-(3-(trifluoromethoxy)phenyl)ethyl)pentanamide and (R)-3-hydroxy-4-methyl-N—((S)-1-(3-(trifluoromethoxy)phenyl)ethyl)pentan amide

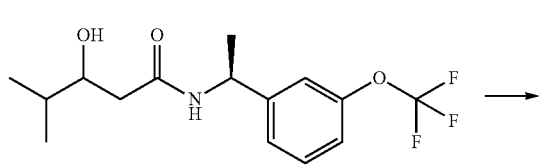

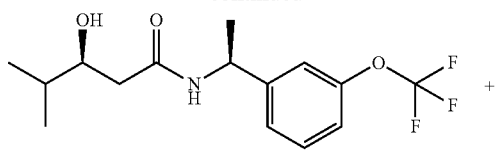

+

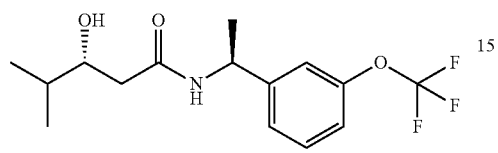

3-Hydroxy-4-methyl-N—((S)-1-(3-(trifluoromethoxy)phenyl)ethyl) pentan amide was separated by chromatography (SiO$_2$, petroleum ether/ethyl acetate=0:1 to 1:1)

Example 20a: 250 mg $^1$H NMR (CDCl$_3$, 400 MHz) δ 7.37 (t, J=8.0 Hz, 1H), 7.27-7.21 (m, 1H), 7.16-7.11 (m, 2H), 6.15 (d, J=6.8 Hz, 1H), 5.16 (quin, J=6.8 Hz, 1H), 3.83-3.74 (m, 1H), 3.26 (d, J=3.2 Hz, 1H), 2.37 (dd, J=15.2, 3.2 Hz, 1H), 2.31 (dd, J=15.2, 8.8 Hz, 1H), 1.74-1.68 (m, 1H), 1.50 (d, J=6.8 Hz, 3H), 0.95 (d, J=6.8 Hz, 3H), 0.93 (d, J=6.8 Hz, 3H).

LC-MS: $t_R$=2.629 min (LCMS Method 2), m/z=320.0 [M+H]$^+$.

SFC: $t_R$=2.404 min (SFC Method 13), de=98.6%, $[α]_D^{20}$=−80.0 (c=0.475 g/100 mL, MeOH).

Example 20b: Yield 470 mg $^1$H NMR (CDCl$_3$, 400 MHz) δ 7.37 (t, J=7.6 Hz, 1H), 7.28-7.23 (m, 1H), 7.16 (s, 1H), 7.14-7.11 (m, 1H), 6.19 (d, J=6.8 Hz, 1H), 5.15 (quin, J=7.2 Hz, 1H), 3.80-3.74 (m, 1H), 3.20 (d, J=3.6 Hz, 1H), 2.38 (dd, J=14.8, 2.4 Hz, 1H), 2.30 (dd, J=14.8, 9.2 Hz, 1H), 1.73-1.66 (m, 1H), 1.49 (d, J=6.8 Hz, 3H), 0.95 (d, J=6.8 Hz, 3H), 0.93 (d, J=6.8 Hz, 3H).

LC-MS: $t_R$=2.654 min (LCMS Method 2), m/z=320.0 [M+H]$^+$.

SFC: $t_R$=1.979 min (SFC Method 13), de=100%, $[α]_D^{20}$=−52.0 (c=0.53 g/100 mL, MeOH).

Example 21a: N—((R)-2-(difluoromethoxy)-1-(3-(trifluoro-methoxy) phenyl)ethyl)-3-hydroxy-4,4-dimethylpentanamide

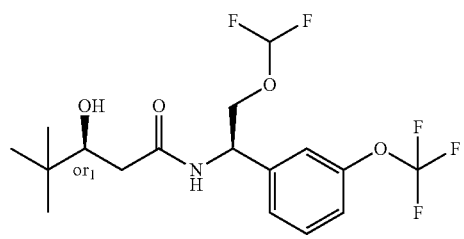 [SMILES: CC(C)(C)[C@@H](O)CC(=O)N[C@@H](COC(F)F)c1cccc(OC(F)(F)F)c1]

and

Example 21b: N—((R)-2-(difluoromethoxy)-1-(3-(trifluoro-methoxy) phenyl)ethyl)-3-hydroxy-4,4-dimethylpentanamide

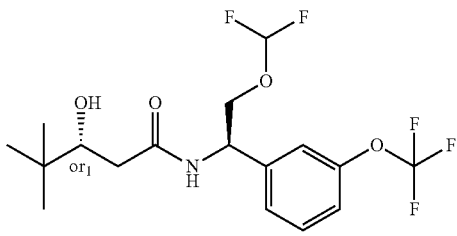 [SMILES: CC(C)(C)[C@H](O)CC(=O)N[C@@H](COC(F)F)c1cccc(OC(F)(F)F)c1]

Step 1: Preparation of N—((R)-2-(difluoromethoxy)-1-(3-(trifluoromethoxy)phenyl)ethyl)-3-hydroxy-4,4-dimethylpentan amide

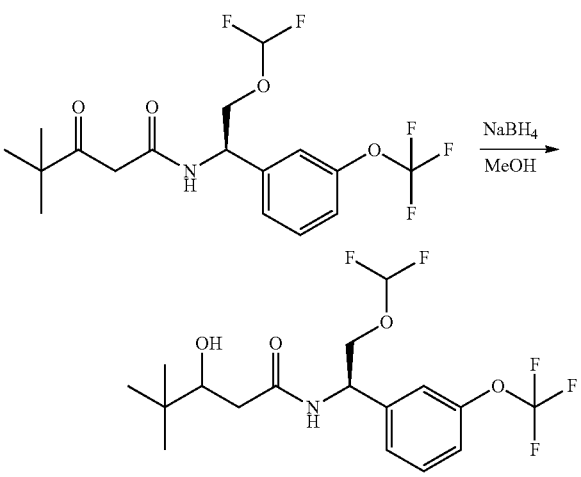

Prepared from Vj. Yield=350 mg, (96%)

Step 2: Separation of N—((R)-2-(difluoromethoxy)-1-(3-(trifluoromethoxy)phenyl)ethyl)-3-(R)-hydroxy-4,4-dimethyl-pentanamide and N—((R)-2-(difluoromethoxy)-1-(3-(trifluoro-methoxy)phenyl)ethyl)-3-(S)-hydroxy-4,4-dimethylpentanamide

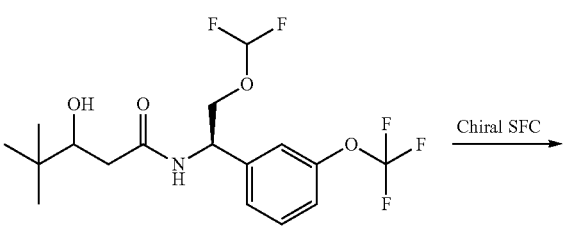

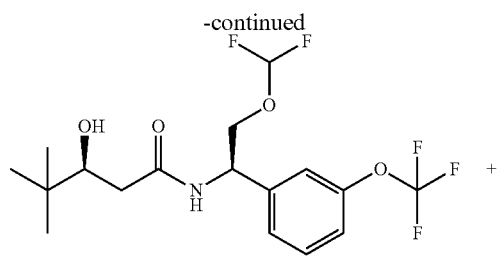

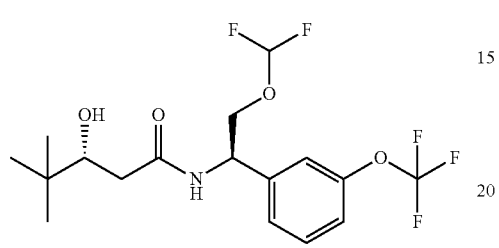

N—((R)-2-(Difluoromethoxy)-1-(3-(trifluoromethoxy) phenyl)ethyl)-3-hydroxy-4,4-dimethyl pentanamide was separated by chiral SFC.

Example 21a: Yield: 98 mg

¹H NMR (CDCl₃ 400 MHz): δ 7.39 (t, J=8.0 Hz, 1H), 7.29-7.26 (m, 1H), 7.20 (s, 1H), 7.16 (d, J=8.0 Hz, 1H), 6.65 (d, J=7.6 Hz, 1H), 6.22 (t, J=74.0 Hz, 1H), 5.34-5.30 (m, 1H), 4.18-4.09 (m, 2H), 3.69 (d, J=10.8 Hz, 1H), 2.91 (s, 1H), 2.45-2.43 (m, 1H), 2.34-2.27 (m, 1H), 0.93 (s, 9H).

LC-MS: $t_R$=2.471 min (LCMS Method 5), m/z=400.0 [M+H]⁺.

SFC: $t_R$=1.935 min (SFC Method 14), de=98.2%, $[\alpha]_D^{20}$=−2.4 (c=1.0 g/100 mL, MeCN).

Example 21b: 160 mg

¹H NMR (DMSO-d⁶ 400 MHz): δ 8.54 (d, J=8.4 Hz, 1H), 7.49 (d, J=8.0 Hz, 1H), 7.41 (d, J=8.0 Hz, 1H), 7.39 (s, 1H), 7.28 (d, J=8.0 Hz, 1H), 6.67 (t, J=76.0 Hz, 1H), 5.21-5.18 (m, 1H), 4.67 (s, 1H), 4.04-3.98 (m, 2H), 3.53 (d, J=10.2 Hz, 1H), 2.31-2.26 (m, 1H), 2.19-2.12 (m, 1H), 0.82 (s, 9H).

LC-MS: $t_R$=2.496 min (LCMS Method 5), m/z=400.0 [M+H]⁺.

SFC: $t_R$=2.461 min (SFC Method 14), de=97.1%, $[\alpha]_D^{20}$=−11.2 (c=1.0 g/100 mL, MeCN).

Example 22a: 3-Hydroxy-N-[(1R)-2-methoxy-1-[3-(trifluoro-methoxy) phenyl]ethyl]-4,4-dimethyl-pentanamide

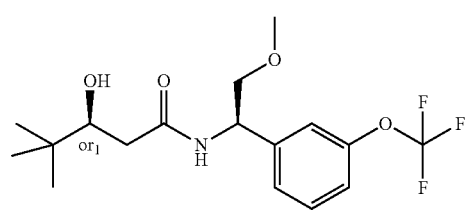 [SMILES: COC[C@H](NC(=O)C[C@H](O)C(C)(C)C)c1cccc(OC(F)(F)F)c1]

Example 22b: 3-Hydroxy-N-[(1R)-2-methoxy-1-[3-(trifluoro-methoxy) phenyl]ethyl]-4,4-dimethyl-pentanamide

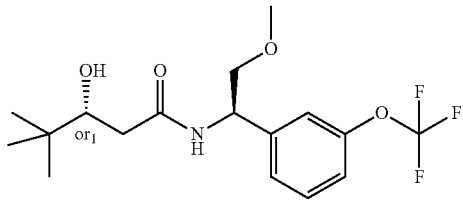 [SMILES: COC[C@H](NC(=O)C[C@@H](O)C(C)(C)C)c1cccc(OC(F)(F)F)c1]

Step 1: Preparation of 3-hydroxy-N-[(1R)-2-methoxy-1-[3-(trifluoromethoxy)phenyl]ethyl]-4,4-dimethyl-pentanamide

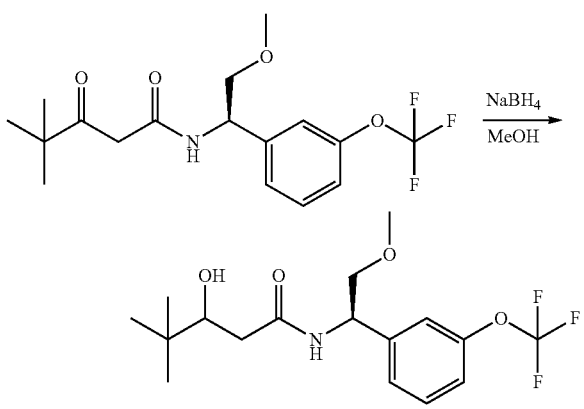

Prepared from Vk. Yield: 84 mg, (60%).

Step 2: Separation of (S)-3-hydroxy-N—((R)-2-methoxy-1-(3-(trifluoromethoxy)phenyl)ethyl)-4,4-dimethylpentanamide and (R)-3-hydroxy-N—((R)-2-methoxy-1-(3-(trifluoromethoxy)phenyl)ethyl)-4,4-dimethylpentanamide

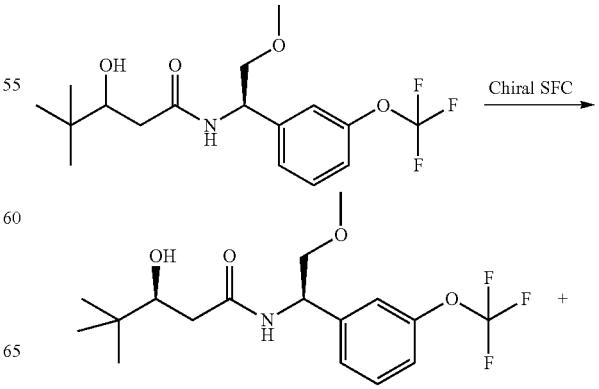

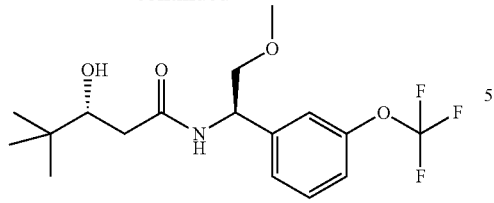

3-Hydroxy-N-[(1R)-2-methoxy-1-[3-(trifluoromethoxy)phenyl]ethyl]-4,4-dimethyl-pentanamide was separated by chiral SFC.

Example 22a: Yield: 40 mg

¹H NMR (CDCl₃ 400 MHz): δ 7.35 (t, J=8.0 Hz, 1H), 7.27-7.26 (m, 1H), 7.20 (s, 1H), 7.12 (d, J=7.6 Hz, 1H), 6.66 (d, J=7.2 Hz, 1H), 5.18-5.14 (m, 1H), 3.70-3.60 (m, 3H), 3.36 (s, 3H), 2.44 (d, J=14.8 Hz, 1H), 2.25-2.33 (m, 1H), 0.93 (s, 9H)

LC-MS: $t_R$=2.410 min (LCMS Method 3), m/z=364.0 [M+H]⁺.

SFC: $t_R$=1.889 min (SFC Method 16), de=100%, $[\alpha]_D^{20}$=−0.4 (c=1.0 g/100 mL, MeCN).

Example 22b: Yield: 38 mg

¹H NMR (CDCl₃ 400 MHz): δ 7.36 (t, J=8.0 Hz, 1H), 7.27-7.25 (m, 1H), 7.18 (s, 1H), 7.12 (d, J=7.6 Hz, 1H), 6.56 (d, J=7.2 Hz, 1H), 5.20-5.15 (m, 1H), 3.69-3.60 (m, 3H), 3.40 (s, 1H), 3.36 (s, 3H), 2.44 (d, J=14.8 Hz, 1H), 2.25-2.33 (m, 1H), 0.93 (s, 9H).

LC-MS: $t_R$=2.523 min (LCMS Method 1), m/z=364.0 [M+H]⁺.

SFC: $t_R$=2.106 min (SFC Method 16), de=98.2%, $[\alpha]_D^{20}$=−2.7 (c=1.0 g/100 mL, MeCN).

Example 5: (S)-2-(3,3-difluoro-1-hydroxycyclobutyl)-N-(1-(3-(trifluoromethoxy)phenyl)ethyl)acetamide

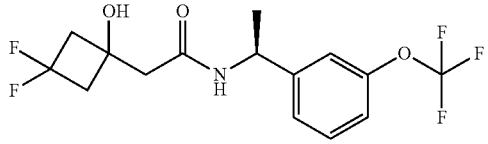 [SMILES: C[C@H](NC(=O)CC1(O)CC(F)(F)C1)c1cccc(OC(F)(F)F)c1]

Step 1

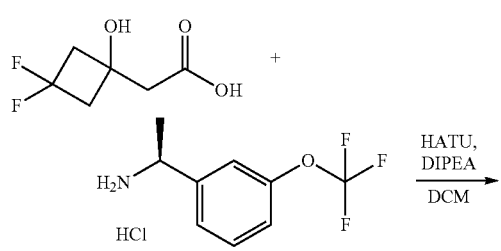

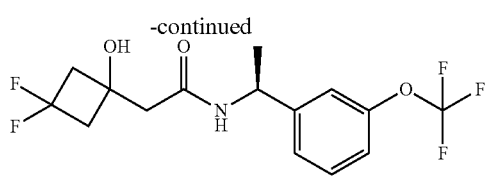

A mixture of (1S)-1-[3-(trifluoromethoxy)phenyl]ethanamine hydrochloride (IIa) (291 mg, 1.20 mmol), 2-(3,3-difluoro-1-hydroxy-cyclobutyl)acetic acid (IIIb) (0.22 g, 1.32 mmol), HATU (549 mg, 1.44 mmol) and DIPEA (467 mg, 3.6 mmol) in DCM (15 mL) was stirred at 20° C. for 16 hours. The mixture was washed with water (40 mL×2) and extracted with DCM (40 mL). The organic layer was washed with brine (10 mL×2), dried over Na₂SO₄ and concentrated. The residue was purified by flash chromatography on silica gel (Eluent of 0~35% Ethyl acetate/petroleum ether gradient) to give the product (0.2 g, 47% yield).

¹H NMR (CDCl₃, 400 MHz): δ 7.41-7.37 (m, 1H), 7.26-7.23 (m, 1H), 7.18-7.13 (m, 2H), 5.93 (br d, J=6.8 Hz, 1H), 5.15 (quin, J=7.2 Hz, 1H), 5.01 (br s, 1H), 2.84-2.42 (m, 6H), 1.53 (d, J=6.8 Hz, 3H).

LC-MS: $t_R$=2.53 min (LCMS Method 2), m/z=354.0 [M+H]⁺.

HPLC: $t_R$=13.3 min. (Chiral HPLC Method 1), de=100%. $[\alpha]_D^{20}$=−51.1 (c=0.23 g/100 mL, MeOH).

The following examples were prepared by similar methodology to Example 5, using the relevant staring materials:

Example 6: (S)-2-(1-Hydroxycyclobutyl)-N-(1-(3-(2,2,2-trifluoroethoxy)phenyl)ethyl) acetamide

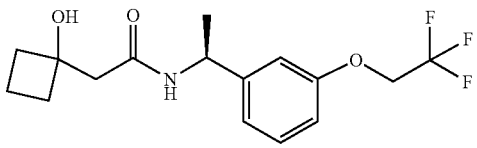 [SMILES: C[C@H](NC(=O)CC1(O)CCC1)c1cccc(OCC(F)(F)F)c1]

Step 1: Preparation of (S)-2-(1-hydroxycyclobutyl)-N-(1-(3-(2,2,2-trifluoroethoxy)phenyl)ethyl)acetamide

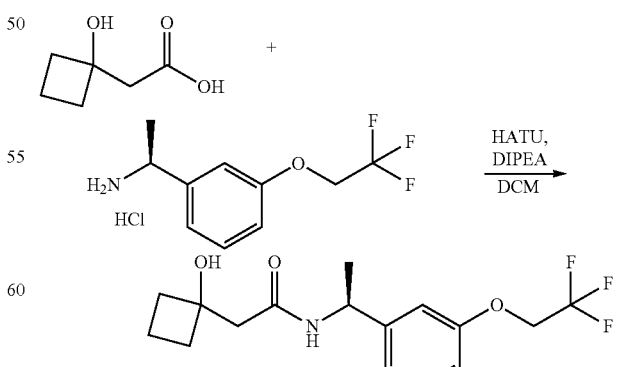

Prepared from IIb (5.0 g, 22.81 mmol), and IIIa (3.3 g, 25.09 mmol).

Yield: 5.2 g, (45%).

¹H NMR (CDCl₃, 400 MHz): δ 7.29 (t, J=8.0 Hz, 1H), 6.99 (d, J=7.6 Hz, 1H), 6.90 (s, 1H), 6.83 (dd, J=8.4 Hz, J=2.4 Hz, 1H), 6.25 (d, J=6.8 Hz, 1H), 5.14-5.07 (m, 1H), 4.35 (q, J=8.0 Hz, 2H), 4.14 (s, 2H), 2.53 (s, 2H), 2.15-1.99 (m, 4H), 1.76 (m, 1H), 1.55 (m, 1H), 1.48 (d, J=6.8 Hz, 3H).

LC-MS: $t_R$=2.49 min (LCMS Method 2), m/z=332.0 [M+H]⁺.

SFC: $t_R$=2.67 min (SFC Method 3), de=96.9%, $[\alpha]_D^{20}$=−69.0 (c=0.1, MeOH).

Example 7a: 3-Hydroxy-4-methyl-N—((S)-1-(3-(2,2,2-trifluoro-ethoxy)phenyl)ethyl)-3-(trifluoromethyl) pentanamide

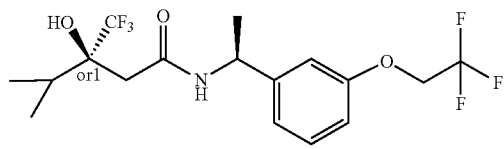 [SMILES: CC(C)[C@@](O)(CC(=O)N[C@@H](C)c1cccc(OCC(F)(F)F)c1)C(F)(F)F]

and

Example 7b: 3-Hydroxy-4-methyl-N—((S)-1-(3-(2,2,2-trifluoro-ethoxy)phenyl)ethyl)-3-(trifluoromethyl) pentanamide

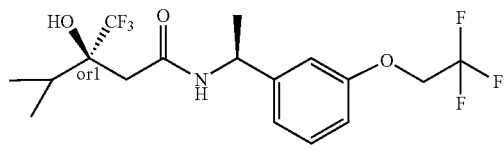 [SMILES: CC(C)[C@@](O)(CC(=O)N[C@@H](C)c1cccc(OCC(F)(F)F)c1)C(F)(F)F]

Step 1: Preparation of 3-Hydroxy-4-methyl-N—((S)-1-(3-(2,2,2-trifluoroethoxy)phenyl)ethyl)-3-(trifluoromethyl)pentanamide

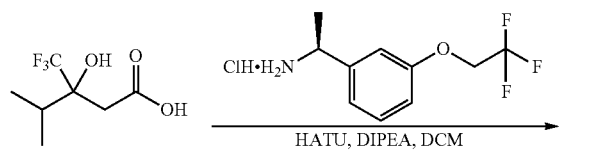

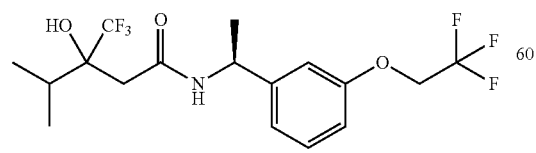

Prepared from IIb and IIIc. Yield: 0.65 g, (crude). The crude was used directly without purification.

Step 2: Separation of (3R)-3-hydroxy-4-methyl-N-[(1S)-1-[3-(2,2,2-trifluoroethoxy)phenyl]ethyl]-3-(trifluoromethyl) pentanamide and (3S)-3-hydroxy-4-methyl-N-[(1S)-1-[3-(2,2,2-trifluoroethoxy)phenyl]ethyl]-3-(trifluoromethyl)pentanamide

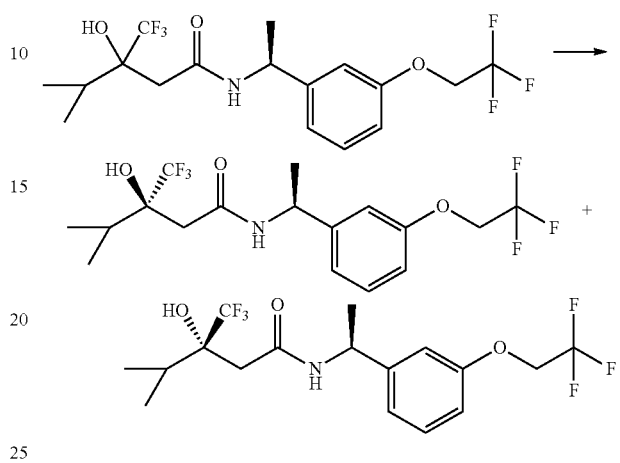

Separated by by flash silica gel chromatography (Eluent of 0~15% Ethyl acetate/petroleum ether gradient).

Example 7a: Yield: 0.29 g

¹H NMR (CDCl₃, 400 MHz): δ 7.32 (t, J=8.0 Hz, 1H), 7.00 (d, J=7.6 Hz, 1H), 6.91 (d, J=2.0 Hz, 1H), 6.85 (dd, J=8.0, 2.4 Hz, 1H), 6.32 (s, 1H), 5.99 (d, J=7.6 Hz, 1H). 5.15-5.07 (m, 1H), 4.36 (q, J=8.0 Hz, 2H), 2.45 (d, J=15.2 Hz, 1H), 2.34 (d, J=15.2 Hz, 1H), 2.13-2.06 (m, 1H), 1.50 (d, J=6.8 Hz, 3H), 1.03 (d, J=6.8 Hz, 3H), 0.97 (d, J=6.8 Hz, 3H).

LC-MS: $t_R$=2.883 min (LCMS Method 4), m/z=402.0 [M+H]⁺.

SFC: $t_R$=2.454 min. (SFC Method 6), de=100%, $[\alpha]_D^{20}$=−43.5 (c=0.0058 g/mL, MeOH).

Example 7b: Yield: 0.23 g

¹H NMR (CDCl₃, 400 MHz): δ 7.32 (t, J=8.0 Hz, 1H), 7.00 (d, J=7.6 Hz, 1H), 6.91-6.84 (m, 2H), 6.33 (s, 1H), 5.90 (d, J=7.6 Hz, 1H), 5.19-5.10 (m, 1H), 4.35 (q, J=8.4 Hz, 2H), 2.51 (d, J=14.8 Hz, 1H), 2.35 (d, J=14.8 Hz, 1H), 2.15-2.06 (m, 1H), 1.52 (d, J=7.2 Hz, 3H), 1.05 (d, J=6.8 Hz, 3H), 0.98 (d, J=6.8 Hz, 3H).

LC-MS: $t_R$=2.834 min (LCMS Method 6), m/z=402.0 [M+H]⁺.

SFC: $t_R$=2.262 min. (SFC Method 7) de=99.8%, $[\alpha]_D^{20}$=−37.1 (c=0.0034 g/mL, MeOH).

Example 9: 4,4,4-Trifluoro-3-hydroxy-N-[(1S)-1-[3-(trifluoro-methoxy)phenyl]ethyl]-3-(trifluoromethyl) butanamide

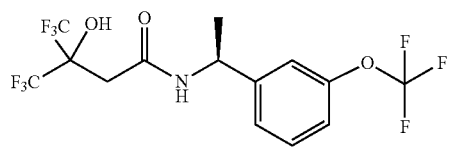 [SMILES: C[C@H](NC(=O)CC(O)(C(F)(F)F)C(F)(F)F)c1cccc(OC(F)(F)F)c1]

Step 1

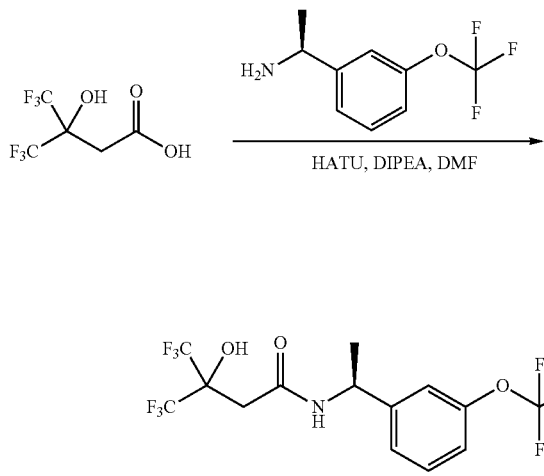

Prepared from IIa and 4,4,4-trifluoro-3-hydroxy-3-(trifluoromethyl)butanoic acid. Yield: 650 mg, (63%)

$^1$H NMR (DMSO-d$^6$ 400 MHz): δ 9.14 (d, J=7.2 Hz, 1H), 8.45 (s, 1H), 7.44 (t, J=8.0 Hz, 1H), 7.32 (d, J=7.6 Hz, 1H), 7.24 (s, 1H), 7.21 (d, J=8.4 Hz, 1H), 5.01-4.93 (m, 1H), 2.89 (s, 2H), 1.34 (d, J=6.8 Hz, 3H).

LC-MS: $t_R$=2.850 min (LCMS Method 4), m/z=413.9 [M+H]$^+$.

Chiral HPLC: $t_R$=15.61 min, (HPLC Method 2), de=98.4%, $[α]_D^{20}$=−41.1 (c=0.185 g/100 mL, MeOH)

Example 10a: 4,4,5,5-Tetrafluoro-3-hydroxy-3-methyl-N—((S)-1-(3-(trifluoromethoxy)phenyl)ethyl) pentanamide

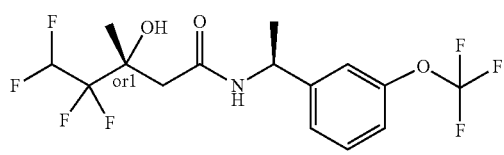 [SMILES: C[C@H](NC(=O)C[C@@](C)(O)C(F)(F)C(F)F)c1cccc(OC(F)(F)F)c1]

and

Example 10b: 4,4,5,5-Tetrafluoro-3-hydroxy-3-methyl-N—((S)-1-(3-(trifluoromethoxy)phenyl)ethyl) pentanamide

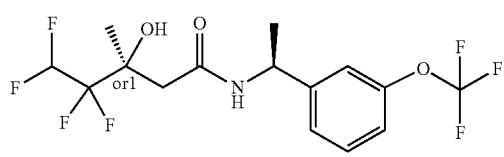 [SMILES: C[C@H](NC(=O)C[C@](C)(O)C(F)(F)C(F)F)c1cccc(OC(F)(F)F)c1]

Step1: Preparation of 4,4,5,5-tetrafluoro-3-hydroxy-3-methyl-N—((S)-1-(3-(trifluoromethoxy)phenyl)ethyl)pentanamide

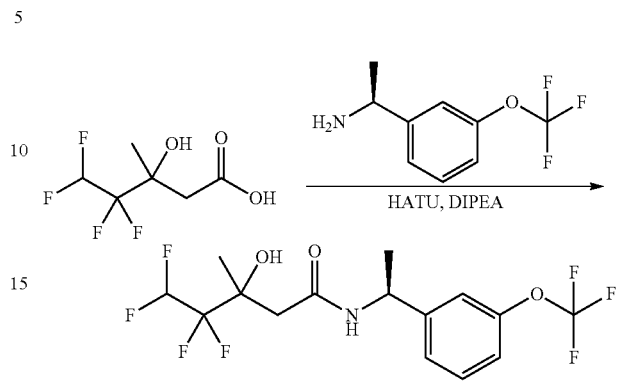

Prepared from IIa and IIId. Yield: 1 g (53%)

Step 2: Separation of (R)-4,4,5,5-tetrafluoro-3-hydroxy-3-methyl-N—((S)-1-(3-(trifluoromethoxy)phenyl)ethyl)pentanamide and (S)-4,4,5,5-tetrafluoro-3-hydroxy-3-methyl-N—((S)-1-(3-(trifluoromethoxy)phenyl)ethyl)pentanamide

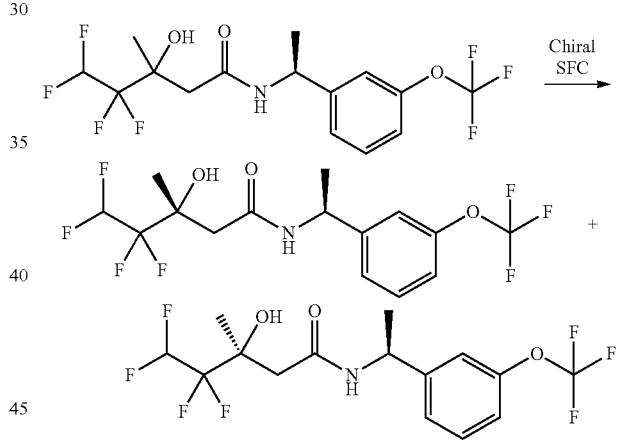

The diastereomers were separated by chiral SFC.

Example 10a: Yield=0.268 g $^1$H NMR (CDCl$_3$ 400 MHz): δ 7.42-7.36 (m, 1H), 7.24 (d, J=7.6 Hz, 1H), 7.17-7.12 (m, 2H), 6.28-5.97 (m, 2H), 5.93 (br d, J=6.0 Hz, 1H), 5.16 (quin, J=6.8 Hz, 1H), 2.69 (d, J=15.2 Hz, 1H), 2.37 (d, J=15.2 Hz, 1H), 1.53 (d, J=6.8 Hz, 3H), 1.40 (s, 3H).

LC-MS: $t_R$=2.759 min (LCMS Method 2), m/z=392.0 [M+H]$^+$.

SFC: $t_R$=1.550 min. (SFC Method 15), de=100%, $[α]_D^{20}$=−50.5 (c=0.19 g/100 mL, MeOH).

Example 10b: Yield=0.148 g $^1$H NMR (CDCl$_3$ 400 MHz): δ 7.44-7.36 (m, 1H), 7.26 (d, J=8.0 Hz, 1H), 7.19-7.12 (m, 2H), 6.33-6.01 (m, 2H), 5.91 (br d, J=6.8 Hz, 1H), 5.16 (quin, J=6.8 Hz, 1H), 2.70 (d, J=15.2 Hz, 1H), 2.35 (d, J=15.2 Hz, 1H), 1.52 (d, J=6.8 Hz, 3H), 1.35 (s, 3H).

LC-MS: $t_R$=2.782 min (LCMS Method 2), m/z=392.0 [M+H]$^+$.

SFC: $t_R$=1.329 min. (SFC Method 15), de=100%, $[\alpha]_D^{20}$=−48.6 (c=0.21 g/100 mL, MeOH).

Example 13a: 5,5,5-Trifluoro-3-hydroxy-3-methyl-N—((S)-1-(3-(trifluoromethoxyphenyl)ethyl) pentanamide

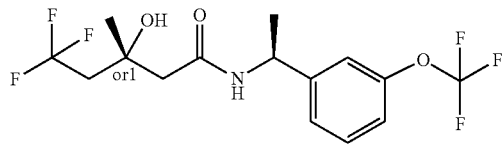 [SMILES: C[C@H](NC(=O)C[C@@](C)(O)CC(F)(F)F)c1cccc(OC(F)(F)F)c1]

and

Example 13b: 5,5,5-Trifluoro-3-hydroxy-3-methyl-N—((S)-1-(3-(trifluoromethoxy)phenyl)ethyl)pentanamide

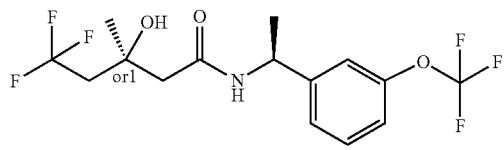 [SMILES: C[C@H](NC(=O)C[C@](C)(O)CC(F)(F)F)c1cccc(OC(F)(F)F)c1]

Step 1: Preparation of 5,5,5-trifluoro-3-hydroxy-3-methyl-N—((S)-1-(3-(trifluoromethoxy)phenyl)ethyl)pentanamide

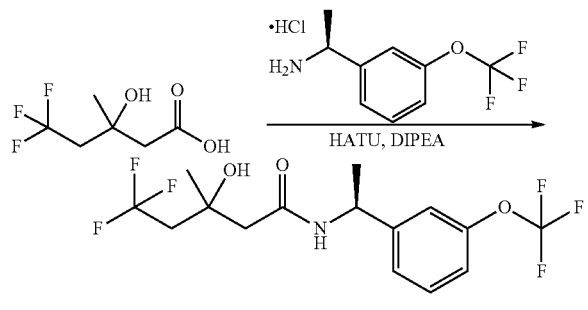

Prepared from IIa and IIIe. Yield: 1 g, (43%)

Step 2: Separation of (R)-5,5,5-trifluoro-3-hydroxy-3-methyl-N—((S)-1-(3-(trifluoromethoxy)phenyl)pentanamide and (S)-5,5,5-trifluoro-3-hydroxy-3-methyl-N—((S)-1-(3-(trifluoro methoxy)phenyl)ethyl)pentanamide

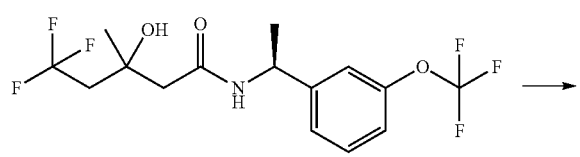

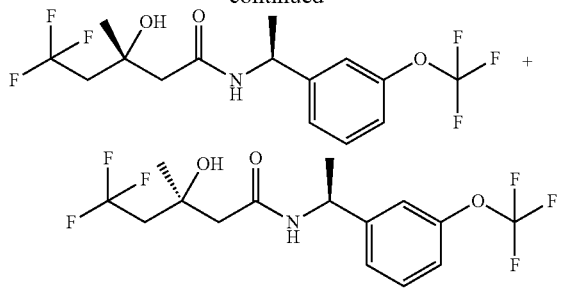

Separated by by flash chromatography on silica gel (Eluent of 0~31% Ethyl acetate/petroleum ether gradient).

Example 13a: Yield=0.421 g $^1$H NMR (CDCl$_3$ 400 MHz): δ 7.42-7.36 (m, 1H), 7.24 (d, J=8.0 Hz, 1H), 7.17-7.12 (m, 2H), 5.98 (br d, J=6.8 Hz, 1H), 5.15 (quin, J=6.8 Hz, 1H), 5.00 (s, 1H), 2.54-2.44 (m, 2H), 2.44-2.31 (m, 2H), 1.51 (d, J=7.2 Hz, 3H), 1.38 (s, 3H), LC-MS: $t_R$=2.666 min (LCMS Method 2), m/z=374.0 [M+H]$^+$.

SFC: $t_R$=1.277 min. (SFC Method 8), de=100%, $[\alpha]_D^{20}$=−51.3 (c=0.23 g/100 mL, MeOH).

Example 13b: 0.261 g $^1$H NMR (CDCl$_3$ 400 MHz): δ 7.42-7.36 (m, 1H), 7.25 (d, J=8.0 Hz, 1H), 7.17-7.12 (m, 2H), 5.96 (br d, J=7.2 Hz, 1H), 5.16 (quin, J=6.8 Hz, 1H), 4.98 (s, 1H), 2.57-2.36 (m, 4H), 1.52 (d, J=6.8 Hz, 3H), 1.36 (s, 3H), LC-MS: $t_R$=2.674 min (LCMS Method 2), m/z=374.0 [M+H]$^+$.

SFC: $t_R$=1.197 min. (SFC Method 8), de=93.4%, $[\alpha]_D^{20}$=−43.2 (c=0.19 g/100 mL, MeOH).

Example 15a: 3-(1-Fluorocyclopropyl)-3-hydroxy-N—((S)-1-(3-(trifluoromethoxy)phenyl)ethyl) butanamide

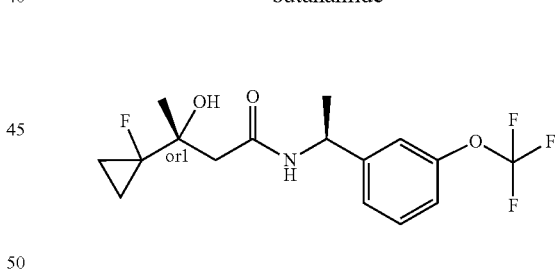

and

Example 15b: 3-(1-Fluorocyclopropyl)-3-hydroxy-N—((S)-1-(3-(trifluoromethoxy)phenyl)ethyl) butanamide

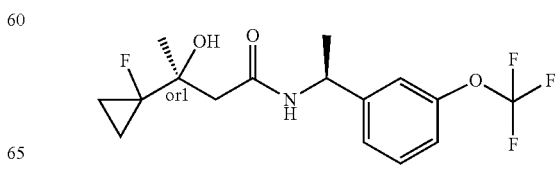

Step 1: Preparation of 3-(1-fluorocyclopropyl)-3-hydroxy-N—((S)-1-(3-(trifluoromethoxy)phenyl)ethyl)butanamide

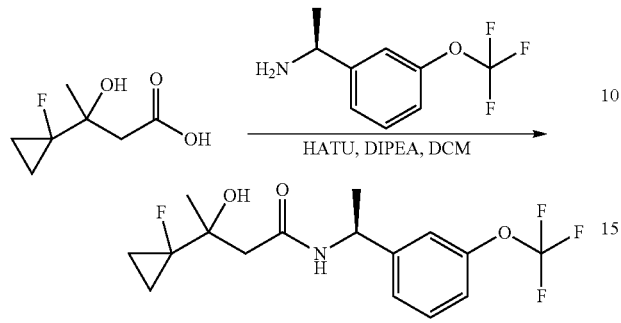

Prepared from IIa and IIIf. The crude was used directly in the next step

Step 2: Separation of (R)-3-(1-fluorocyclopropyl)-3-hydroxy-N—((S)-1-(3-(trifluoromethoxy)phenyl)ethyl)butanamide and (S)-3-(1-fluorocyclopropyl)-3-hydroxy-N—((S)-1-(3-(trifluoro-methoxy)phenyl)ethyl)butanamide

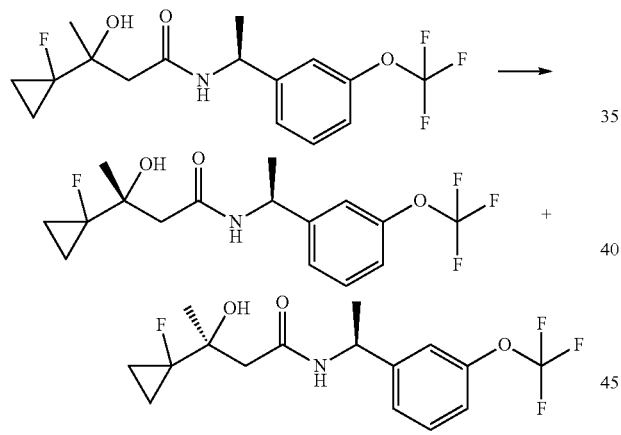

Separated by flash chromatography on silica gel (Eluent of 0~30% Ethyl acetate/petroleum ether gradient).

Example 15a: Yield=1.05 g $^1$H NMR (CDCl$_3$ 400 MHz): δ 7.37 (t, J=8.0 Hz, 1H), 7.27-7.24 (m, 1H), 7.17-7.12 (m, 2H), 6.11 (br s, 1H), 5.18-5.10 (m, 1H), 5.02 (s, 1H), 2.61 (dd, J=14.4, 2.4 Hz, 1H), 2.46 (dd, J=14.4, 1.6 Hz, 1H), 1.51 (d, J=7.2 Hz, 3H), 1.33 (s, 3H), 0.78-0.68 (m, 3H), 0.52-0.50 (m, 1H).

LC-MS: $t_R$=2.359 min (LCMS Method 3), m/z=350.0 [M+H]$^+$.

SFC: $t_R$=2.027 min. (SFC Method 9), de=93.9%, $[α]_D^{20}$=−48.3 (c=0.24 g/100 mL, MeOH).

Example 15b: Yield: 0.80 g $^1$H NMR (CDCl$_3$ 400 MHz): δ 7.38 (t, J=8.0 Hz, 1H), 7.27-7.23 (m, 1H), 7.15-7.12 (m, 2H), 6.06 (d, J=7.2 Hz, 1H), 5.19-5.11 (m, 1H), 4.99 (s, 1H), 2.62 (dd, J=14.4, 2.0 Hz, 1H), 2.47 (d, J=1.6 Hz, 1H), 2.43 (d, J=1.6 Hz, 1H), 1.51 (d, J=7.2 Hz, 3H), 1.33 (s, 3H), 0.97-0.87 (m, 1H), 0.85-0.81 (m, 3H).

LC-MS: $t_R$=2.655 min (LCMS Method 2), m/z=350.0 [M+H]$^+$.

SFC: $t_R$=1.937 min. (SFC Method 9), de=98.7%, $[α]_D^{20}$=−64.4 (c=0.27 g/100 mL, MeOH).

Example 17: (R)-2-(1-Hydroxycyclopentyl)-N-(2-methoxy-1-(3-(trifluoromethoxy)phenyl)ethyl) acetamide

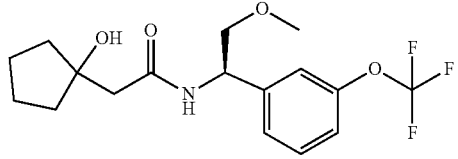 [SMILES: COC[C@H](NC(=O)CC1(O)CCCC1)c1cccc(OC(F)(F)F)c1]

Prepared from IIa and 2-(1-hydroxycyclopentyl)acetic acid.

Yield: 30 mg, (12.8%).

$^1$H NMR (400 MHz, CDCl$_3$) δ 7.37 (t, J=8.0 Hz, 1H), 7.26-7.25 (m, 1H), 7.19 (s, 1H), 7.16-7.11 (m, 1H), 6.66 (br d, J=7.2 Hz, 1H), 5.21-5.15 (m, 1H), 3.82 (s, 1H), 3.70-3.60 (m, 2H), 3.37 (s, 3H), 2.59-2.49 (m, 2H), 1.86-1.81 (m, 4H), 1.59-1.56 (m, 4H).

LC-MS: $t_R$=2.481 min (LCMS Method 2), m/z=362.0 [M+H]$^+$,

SFC: $t_R$=2.33 min. (SFC Method 10), de=100%, $[α]_D^{20}$=−44.0, (c=1 mg/mL, MeOH).

Example 18a: 3-Cyclopropyl-3-hydroxy-N—((S)-1-(3-(2,2,2-trifluoroethoxy)phenyl)ethyl) butanamide

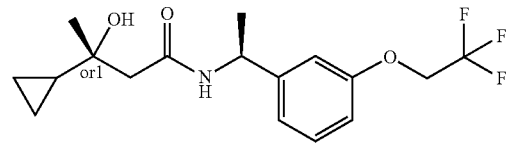 [SMILES: C[C@H](NC(=O)C[C@@](C)(O)C1CC1)c1cccc(OCC(F)(F)F)c1]

and

Example 18b: 3-Cyclopropyl-3-hydroxy-N—((S)-1-(3-(2,2,2-trifluoroethoxy)phenyl)ethyl) butanamide

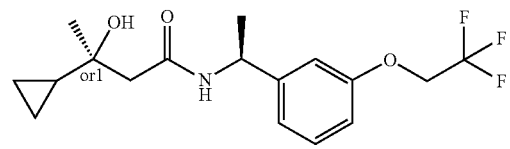 [SMILES: C[C@H](NC(=O)C[C@](C)(O)C1CC1)c1cccc(OCC(F)(F)F)c1]

Step 1: Preparation of 3-cyclopropyl-3-hydroxy-N—((S)-1-(3-(2,2,2-trifluoroethoxy)phenyl)ethyl)butanamide

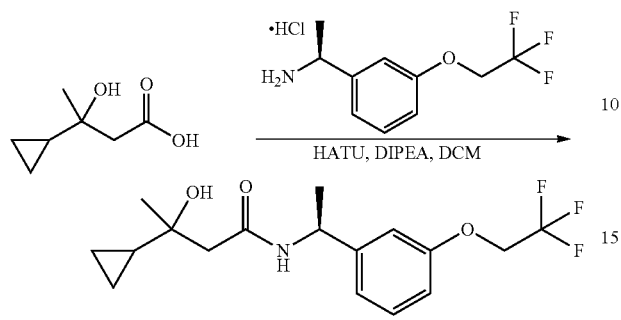

Prepared from IIb and IIIg. Yield: 3.7 g, (30.9%)

Step 2: Separation of (R)-3-cyclopropyl-3-hydroxy-N—((S)-1-(3-(2,2,2-trifluoroethoxy)phenyl)ethyl)butanamide and (S)-3-cyclopropyl-3-hydroxy-N—((S)-1-(3-(2,2,2-trifluoroethoxy)phenyl)ethyl)butanamide

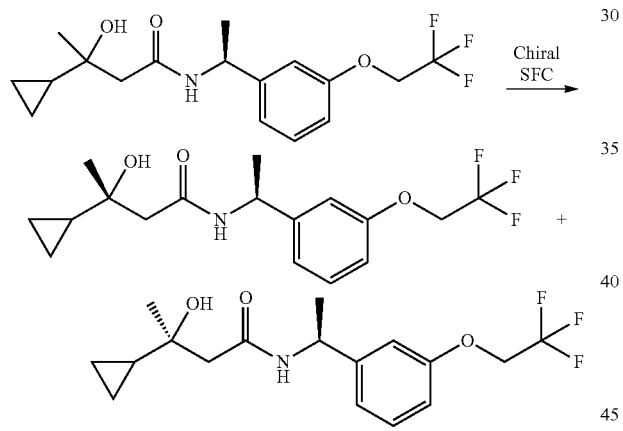

Separated by chiral SFC.

Example 18a: Yield: 1.59 g

¹H NMR (400 MHz, DMSO-d₆) δ 8.32 (d, J=8.0 Hz, 1H), 7.28 (t, J=8.0 Hz, 1H), 7.04-6.98 (m, 2H), 6.93-6.90 (m, 1H), 4.97-4.91 (m, 1H), 4.73 (q, J=8.8 Hz, 2H), 4.61 (s, 1H), 2.37-2.25 (m, 2H), 1.34 (d, J=7.2 Hz, 3H), 1.10 (s, 3H), 0.87-0.84 (m, 1H), 0.30-0.09 (m, 4H).

LC-MS: $t_R$=2.629 min (LCMS Method 2), m/z=328.0 [M+H−18]⁺.

SFC: $t_R$=3.154 min (SFC Method 11), de=99.7%, $[\alpha]_D^{20}$=−62.0 (c=2 mg/mL, MeOH)

Example 18b: Yield: 1.44 g

¹H NMR (400 MHz, DMSO-d₆) δ 8.19 (br d, J=8.0 Hz, 1H), 7.12 (t, J=8.0 Hz, 1H), 6.87-6.79 (m, 2H), 6.77-6.74 (m, 1H), 4.81-4.73 (m, 1H), 4.57 (q, J=8.8 Hz, 2H), 4.42 (s, 1H), 2.19-2.08 (m, 2H), 1.17 (d, J=6.8 Hz, 3H), 0.94 (s, 3H), 0.73-0.64 (m, 1H), 0.19-0.00 (m, 4H).

LC-MS: $t_R$=2.643 min (LCMS Method 2), m/z=328.0 [M+H−18]⁺.

SFC: $t_R$=2.570 min. (SFC Method 11), de=97.0%, $[\alpha]_D^{20}$=−58.0 (c=2 mg/mL, MeOH)

Example 19a: 4,4,4-Trifluoro-3-hydroxy-3-methyl-N—((S)-1-(3-(2,2,2-trifluoroethoxy)phenyl)ethyl)butanamide

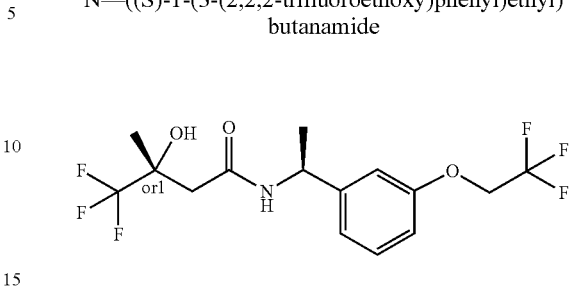

and

Example 19b: 4,4,4-Trifluoro-3-hydroxy-3-methyl-N—((S)-1-(3-(2,2,2-trifluoroethoxy)phenyl)ethyl)butanamide

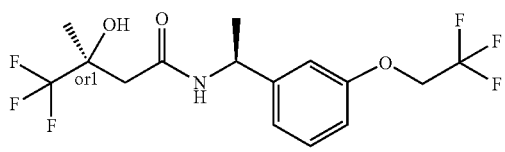 [SMILES: C[C@H](NC(=O)C[C@](C)(O)C(F)(F)F)c1cccc(OCC(F)(F)F)c1]

Step 1: Preparation of 4,4,4-trifluoro-3-hydroxy-3-methyl-N—((S)-1-(3-(2,2,2-trifluoroethoxy)phenyl)ethyl)butanamide

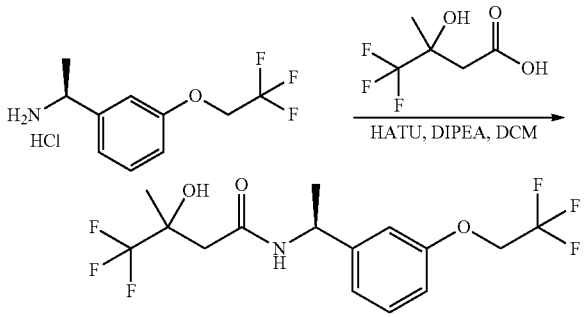

Prepared from IIb and 4,4,4-trifluoro-3-hydroxy-3-methyl-butanoic acid. Yield: 6.67 g, (73%)

Step 2: Separation of (R)-4,4,4-trifluoro-3-hydroxy-3-methyl-N—((S)-1-(3-(2,2,2-trifluoroethoxy))ethyl)butanamide and (S)-4,4,4-trifluoro-3-hydroxy-3-methyl-N—((S)-1-(3-(2,2,2-trifluoro ethoxy)phenyl)ethyl)butanamide

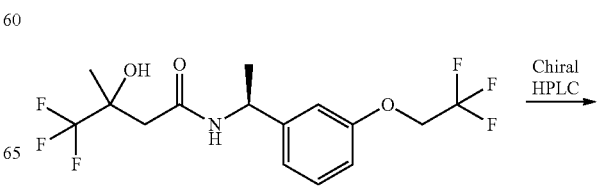

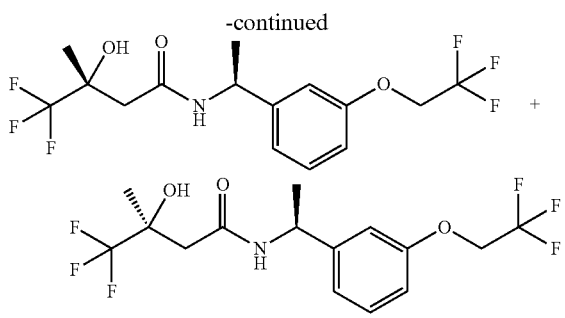

Example 19a: 2.3 g $^1$H NMR (CDCl$_3$, 400 MHz) δ 7.32 (t, J=8.0 Hz, 1H), 6.99 (d, J=7.8 Hz, 1H), 6.92-6.88 (m, 1H), 6.88-6.83 (m, 1H), 5.99 (br d, J=6.8 Hz, 1H), 5.84 (s, 1H), 5.12 (quin, J=7.2 Hz, 1H), 4.35 (q, J=8.0 Hz, 2H), 2.51 (dd, J=53.2, 15.2 Hz, 2H), 1.51 (d, J=7.2 Hz, 3H), 1.41 (s, 3H); LC-MS: $t_R$=2.732 min (LCMS Method 2), m/z=374.0 [M+H]$^+$.

SFC: $t_R$=1.721 min (SFC Method 12), de=99.6%, $[α]_D^{20}$=−51.0 (c=0.20, MeOH).

Example 19b: 0.86 g $^1$H NMR (CDCl$_3$, 400 MHz) δ7.33 (t, J=8.0 Hz, 1H), 7.00 (d, J=7.2 Hz, 1H), 6.93-6.90 (m, 1H), 6.88-6.83 (m, 1H), 5.98-5.91 (m, 1H), 5.91 (s, 1H), 5.12 (quin, J=7.2 Hz, 1H), 4.36 (q, J=8.0 Hz, 2H), 2.50 (dd, J=57.6, 14.8 Hz, 2H), 1.51 (d, J=6.8 Hz, 3H), 1.39 (s, 3H); LC-MS: $t_R$=2.737 min (LCMS Method 2), m/z=374.0 [M+H]$^+$.

SFC: $t_R$=1.904 min (SFC Method 12), de=100%, $[α]_D^{20}$=−57.1 (c=0.21, MeOH).

The invention claimed is:

1. A method of treating a patient in the need thereof suffering from mania, acute stress reactions, bipolar depression, major depression, anxiety, panic attacks, social phobia, chronic pain, neuropathy, autism spectrum disorders, Huntington's chorea, or sclerosis, comprising administering to the patient a therapeutically effective amount of a compound of Formula (I):

Formula I

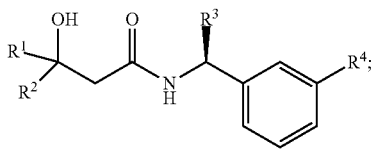

wherein

R1 is selected from the group consisting of C$_1$-C$_6$ alkyl, CF$_3$, CH$_2$CF$_3$, CF$_2$CHF$_2$, and C$_3$-C$_8$ cycloalkyl, wherein said C$_3$-C$_8$ cycloalkyl may be substituted with 1 or 2 F, CHF$_2$ or CF$_3$, and R2 is H, C$_1$-C$_6$ alkyl or CF$_3$;

or

R1 and R2 combine to form C$_3$-C$_5$ cycloalkyl optionally substituted with 1 or 2 F, CHF$_2$ or CF$_3$;

R3 is C$_1$-C$_3$ alkyl or CH$_2$O—C$_{1-3}$ alkyl, wherein said C$_1$-C$_3$ alkyl or CH$_2$O—C$_{1-3}$ alkyl may be optionally substituted with 1 or 2 F; and R4 is selected from the group consisting of CF$_3$, OCF$_3$, OCH$_2$CF$_3$ and OCHF$_2$.

2. The method of claim 1, wherein R4 is OCF$_3$ or OCHF$_2$.

3. The method of claim 1, wherein R2 is H or CH$_3$.

4. The method of claim 1, wherein R3 is CH$_2$O—C$_{1-3}$ alkyl.

5. The method of claim 1, wherein R1 is C$_3$-C$_4$ cycloalkyl optionally substituted with 1 or 2 F, CHF$_2$ or CF$_3$.

6. The method of claim 1, wherein R1 is t-butyl and R2 is H.

7. The method of claim 1, wherein R1 and R2 combine to form cyclobutyl optionally substituted with 1 or 2 F.

8. The method of claim 1, wherein the compound is selected from the group consisting of:

(S)-3-hydroxy-4,4-dimethyl-N-[(1S)-1-[3-(trifluoromethoxy) phenyl]ethyl]pentanamide, R)-3-hydroxy-4,4-dimethyl-N-[(1S)-1-[3-(trifluoromethoxy) phenyl]ethyl]pentanamide, (S)-3-hydroxy-4,4-dimethyl-N—((S)-1-(3-(2,2,2-trifluoroethoxy) phenyl) ethyl) pentanamide, (R)-3-hydroxy-4,4-dimethyl-N—((S)-1-(3-(2,2,2-trifluoroethoxy) phenyl) ethyl) pentanamide, (S)—N—((S)-1-(3-(difluoromethoxy) phenyl) ethyl)-3-hydroxy-4,4-dimethylpentanamide, (R)—N—((S)-1-(3-(difluoromethoxy) phenyl) ethyl)-3-hydroxy-4,4-dimethylpentanamide, (S)-3-hydroxy-4,4-dimethyl-N—((S)-1-(3-(trifluoromethyl) phenyl) ethyl) pentanamide, (R)-3-hydroxy-4,4-dimethyl-N—((S)-1-(3-(trifluoromethyl) phenyl) ethyl) pentanamide, (S)-3-hydroxy-4,4-dimethyl-N—((S)-1-(3-(trifluoromethoxy) phenyl) propyl) pentanamide, (R)-3-hydroxy-4,4-dimethyl-N—((S)-1-(3-(trifluoromethoxy) phenyl) propyl) pentanamide, (S)-3-(3,3-difluorocyclobutyl)-3-hydroxy-N—((S)-1-(3-(trifluoromethoxy) phenyl) ethyl) propanamide, (R)-3-(3,3-difluorocyclobutyl)-3-hydroxy-N—((S)-1-(3-(trifluoromethoxy) phenyl) ethyl) propanamide, (S)-3-hydroxy-4-methyl-N—((S)-1-(3-(2,2,2-trifluoroethoxy) phenyl) ethyl) pentanamide, (R)-3-hydroxy-4-methyl-N—((S)-1-(3-(2,2,2-trifluoroethoxy) phenyl) ethyl) pentanamide, (S)-3-(1-(difluoromethyl) cyclopropyl)-3-hydroxy-N—((S)-1-(3-(trifluoro-methoxy) phenyl) ethyl) propanamide, (R)-3-(1-(difluoromethyl) cyclopropyl)-3-hydroxy-N—((S)-1-(3-(trifluoromethoxy) phenyl) ethyl) propanamide, (R)-3-hydroxy-N—((S)-1-(3-(trifluoromethoxy) phenyl) ethyl)-3-(1-(trifluoromethyl) cyclopropyl) propanamide, (S)-3-hydroxy-N—((S)-1-(3-(trifluoromethoxy) phenyl) ethyl)-3-(1-(trifluoromethyl) cyclopropyl) propanamide, (S)-3-hydroxy-4-methyl-N—((S)-1-(3-(trifluoromethoxy) phenyl) ethyl) pentanamide, (R)-3-hydroxy-4-methyl-N—((S)-1-(3-(trifluoromethoxy) phenyl) ethyl) pentanamide, N—((R)-2-(difluoromethoxy)-1-(3-(trifluoromethoxy) phenyl) ethyl)-3-(R)-hydroxy-4,4-dimethylpentanamide, N—((R)-2-(difluoromethoxy)-1-(3-(trifluoromethoxy) phenyl) ethyl)-3-(S)-hydroxy-4,4-dimethylpentanamide, (S)-3-hydroxy-N—((R)-2-methoxy-1-(3-(trifluoromethoxy) phenyl) ethyl)-4,4-dimethylpentanamide, (R)-3-hydroxy-N—((R)-2-methoxy-1-(3-(trifluoromethoxy) phenyl) ethyl)-4,4-dimethylpentanamide, (S)-2-(3,3-difluoro-1-hydroxycyclobutyl)-N-(1-(3-(trifluoromethoxy) phenyl) ethyl) acetamide, (S)-2-(1-hydroxycyclobutyl)-N-(1-(3-(2,2,2-trifluoroethoxy) phenyl) ethyl) acetamide, (3R)-3-hydroxy-4-methyl-N-[(1S)-1-[3-(2,2,2-trifluoroethoxy) phenyl] ethyl]-3-(trifluoromethyl) pentanamide, (3S)-3-hydroxy-4-methyl-N-[(1S)-1-[3-(2,2,2-trifluoroethoxy) phenyl]ethyl]-3-(trifluoromethyl) pentanamide, 4,4,4-trifluoro-3-hydroxy-N-[(1S)-1-[3-(trifluoromethoxy) phenyl]ethyl]-3-(trifluoromethyl) butanamide, (R)-4,4,5,5-tetrafluoro-3-hydroxy-3-methyl-N—((S)-1-(3-(trifluoromethoxy) phenyl) ethyl) pentanamide, (S)-4,4,5,5-tetrafluoro-3-hydroxy-3-methyl-N—((S)-1-(3-(trifluoromethoxy) phenyl) ethyl) pentanamide, (R)-5,5,5-trifluoro-3-hydroxy-3-methyl-N—((S)-1-(3-(trifluoromethoxy) phenyl) ethyl) pentanamide, (S)-5,5,5-trifluoro-3-hydroxy-3-methyl-N—((S)-1-(3-(trifluoro methoxy) phenyl) ethyl) pentanamide, (R)-3-(1-fluorocyclopropyl)-3-hydroxy-N—((S)-1-(3-(trifluoromethoxy) phenyl) ethyl) butanamide, (S)-3-(1-fluorocyclopropyl)-3-hydroxy-N—((S)-1-(3-(trifluoro-methoxy) phenyl) ethyl) butanamide, (R)-2-(1-hydroxycyclopentyl)-N-(2-methoxy-1-(3-(trifluoromethoxy) phenyl) ethyl) acetamide, (R)-3-cyclopropyl-3-hydroxy-N—((S)-1-(3-(2,2,2-trifluoroethoxy) phenyl) ethyl) butanamide, (S)-3-cyclopropyl-3-hydroxy-N—((S)-1-(3-(2,2,2-trifluoroethoxy) phenyl) ethyl) butanamide, (R)-4,4,4-trifluoro-3-hydroxy-3-methyl-N—((S)-1-(3-(2,2,2-trifluoroethoxy) phenyl) ethyl) butanamide, and (S)-4,4,4-trifluoro-3-hydroxy-3-methyl-N—((S)-1-(3-(2,2,2-trifluoroethoxy) phenyl) ethyl) butanamide.

9. The method of claim 1, wherein the compound is(S)-3-hydroxy-4,4-dimethyl-N—((S)-1-(3-(trifluoromethoxy) phenyl) ethyl) pentanamide, (S)-2-(3,3-difluoro-1-hydroxycyclobutyl)-N-(1-(3-(trifluoromethoxy) phenyl) ethyl) acetamide, (S)-2-(1-hydroxycyclobutyl)-N-(1-(3-(2,2,2-trifluoroethoxy) phenyl) ethyl) acetamide, 4,4,4-trifluoro-3-hydroxy-N-[(1S)-1-[3-(trifluoro-methoxy) phenyl]ethyl]-3-(trifluoromethyl) butanamide, 3-hydroxy-4-methyl-N—((S)-1-(3-(trifluoromethoxy) phenyl) ethyl) pentanamide, or N—((R)-2-(difluoromethoxy)-1-(3-(trifluoro-methoxy) phenyl) ethyl)-3-hydroxy-4,4-dimethylpentanamide.

10. The method of claim 1, wherein the method is of treating a patient in the need thereof suffering from sclerosis.

11. The method of claim 1, wherein the method is of treating a patient in the need thereof suffering from chronic pain.

12. The method of claim 1, wherein the method is of treating a patient in the need thereof suffering from neuropathy.

13. The method of claim 1, wherein the method is of treating a patient in the need thereof suffering from bipolar depression or major depression.

14. The method of claim 1, wherein the neuropathy is neuropathic pain.

15. The method of claim 1, wherein the method is of treating a patient in the need thereof suffering from bipolar depression, major depression, anxiety, panic attacks, social phobia, chronic pain, neuropathy, or sclerosis.

16. The method of claim 1, wherein the patient is a human.

17. The method of claim 1, wherein the compound is administered by oral, rectal, nasal, buccal, sublingual, transdermal or parenteral administration.

18. The method of claim 1, wherein the compound is administered by oral administration.

19. The method of claim 1, wherein the compound is administered in an amount from about 0.001 mg/body weight per day to about 100 mg/kg body weight per day.

20. The method of claim 1, wherein the compound is administered in an amount from about 0.01 mg/body weight per day to about 50 mg/kg body weight per day.

* * * * *

UNITED STATES PATENT AND TRADEMARK OFFICE
CERTIFICATE OF CORRECTION

Page 1 of 2

PATENT NO. : 12,258,305 B2
APPLICATION NO. : 17/869116
DATED : March 25, 2025
INVENTOR(S) : Mario Rottlander et al.

It is certified that error appears in the above-identified patent and that said Letters Patent is hereby corrected as shown below:

In the Specification

At Columns 19 and 20, the formula:

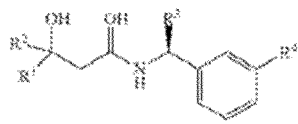

Should be replaced with the formula:

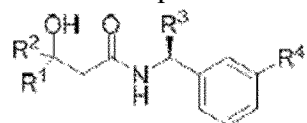

At Columns 19 and 20, the formula:

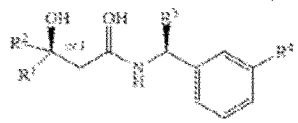

Should be replaced with the formula:

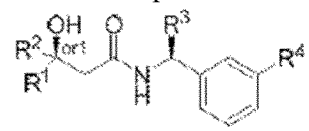

In the Claims

In Claim 8, at Column 84, Lines 13-14, the text:
R)-3-hydroxy-4,4-dimethyl-N-[(1S)-1-[3-(trifluoromethoxy) phenyl]ethyl]pentanamide
Should be replaced with:
(R)-3-hydroxy-4,4-dimethyl-N-[(1S)-1-[3-(trifluoromethoxy) phenyl]ethyl]pentanamide Signed and Sealed this
Twenty-seventh Day of May, 2025

Coke Morgan Stewart
*Acting Director of the United States Patent and Trademark Office*

In Claim 9, at Column 85, Lines 33-35, the text:
The method of claim 1, where in the compound is(S)-3-hydroxy-4,4-dimethyl-N—((S)-1-(3-(trifluoromethoxy)phenyl) ethyl)pentanamide
Should be replaced with:
The method of claim 1, where in the compound is (S)-3-hydroxy-4,4-dimethyl-N—((S)-1-(3-(trifluoromethoxy)phenyl) ethyl)pentanamide